United States Patent
Stevenson et al.

(10) Patent No.: US 7,038,900 B2
(45) Date of Patent: May 2, 2006

(54) EMI FILTER TERMINAL ASSEMBLY WITH WIRE BOND PADS FOR HUMAN IMPLANT APPLICATIONS

(75) Inventors: Robert A. Stevenson, Santa Clarita, CA (US); Richard L. Brendel, Carson City, NV (US); Christine Frysz, Marriottsville, MD (US); Haytham Hussein, Woodstock, MD (US); Scott Knappen, Annapolis, MD (US); Ryan A. Stevenson, Santa Clarita, CA (US)

(73) Assignee: Greatbatch-Sierra, Inc., Carson City, NV (US)

( * ) Notice: Subject to any disclaimer, the term of this patent is extended or adjusted under 35 U.S.C. 154(b) by 198 days.

(21) Appl. No.: 10/842,967

(22) Filed: May 10, 2004

(65) Prior Publication Data

US 2005/0007718 A1 Jan. 13, 2005

Related U.S. Application Data

(63) Continuation-in-part of application No. 10/825,900, filed on Apr. 15, 2004, and a continuation-in-part of application No. 10/377,272, filed on Feb. 27, 2003, now Pat. No. 6,765,780, and a continuation-in-part of application No. 10/377,086, filed on Feb. 27, 2003, now Pat. No. 6,765,779, and a continuation-in-part of application No. 10/377,018, filed on Feb. 27, 2003, now Pat. No. 6,888,715.

(60) Provisional application No. 60/548,770, filed on Feb. 27, 2004, and provisional application No. 60/508,426, filed on Oct. 2, 2003.

(51) Int. Cl.
*H01G 4/35* (2006.01)

(52) U.S. Cl. .................. 361/302; 361/303; 361/305; 361/306.1; 361/306.3; 361/308.1; 333/182; 333/185

(58) Field of Classification Search ................ 361/302, 361/305, 303, 301.2, 301.4, 306.1, 306.3, 361/307, 308, 309, 321.1, 321.5; 333/182, 333/185

See application file for complete search history.

(56) References Cited

U.S. PATENT DOCUMENTS

| | | | |
|---|---|---|---|
| 2,756,375 A | 7/1956 | Peck |
| 3,235,939 A | 2/1966 | Rodriguez et al. |
| 3,538,464 A | 11/1970 | Walsh |
| 3,920,888 A | 11/1975 | Barr |
| 4,083,022 A | 4/1978 | Nijman |
| 4,144,509 A | 3/1979 | Boutros |
| 4,148,003 A | 4/1979 | Colburn et al. |
| 4,152,540 A | 5/1979 | Duncan et al. |
| 4,220,813 A | 9/1980 | Kyle |
| 4,247,881 A | 1/1981 | Coleman |
| 4,314,213 A | 2/1982 | Wakino |
| 4,352,951 A | 10/1982 | Kyle |
| 4,362,792 A | 12/1982 | Bowsky et al. |
| 4,424,551 A | 1/1984 | Stevenson et al. |
| 4,456,786 A | 6/1984 | Kyle |
| 4,737,601 A | 4/1988 | Gartzke |

(Continued)

OTHER PUBLICATIONS

Dr. Gary Ewell, "A Capacitor's Inductance", Capacitor and Resistor Technology Symposium (CARTS–Europe), Lisbon, Portugal, Oct. 19–22, 1999.

*Primary Examiner*—Dean A. Reichard
*Assistant Examiner*—Nguyen T. Ha
(74) *Attorney, Agent, or Firm*—Kelly Lowry & Kelly, LLP

(57) ABSTRACT

An electro-magnetic interference filter terminal assembly for active implantable medical devices includes a structural pad in the form of a substrate or attached wire bond pad, for convenient attachment of wires from the circuitry inside the implantable medical device to the capacitor structure via thermal or ultrasonic bonding, soldering or the like while shielding the capacitor from forces applied to the assembly during attachment of the wires.

176 Claims, 39 Drawing Sheets

U.S. PATENT DOCUMENTS

| | | |
|---|---|---|
| 4,741,710 A | 5/1988 | Hogan et al. |
| 5,032,692 A | 7/1991 | DeVolder |
| 5,070,605 A | 12/1991 | Daglow et al. |
| 5,142,430 A | 8/1992 | Anthony |
| 5,333,095 A | 7/1994 | Stevenson et al. |
| 5,440,447 A | 8/1995 | Shipman et al. |
| 5,539,611 A | 7/1996 | Hegner et al. |
| 5,650,759 A | 7/1997 | Hittman et al. |
| 5,670,063 A | 9/1997 | Hegner et al. |
| 5,751,539 A | 5/1998 | Stevenson et al. |
| 5,759,197 A | 6/1998 | Sawchuk et al. |
| 5,825,608 A | 10/1998 | Duva et al. |
| 5,836,992 A | 11/1998 | Thompson et al. |
| 5,867,361 A | 2/1999 | Wolf et al. |
| 5,870,272 A | 2/1999 | Seifried et al. |
| 5,905,627 A | 5/1999 | Brendel et al. |
| 5,959,829 A | 9/1999 | Stevenson et al. |
| 5,973,906 A | 10/1999 | Stevenson et al. |
| 6,008,980 A | 12/1999 | Stevenson et al. |
| 6,031,710 A | 2/2000 | Wolf et al. |
| 6,414,835 B1 | 7/2002 | Wolf et al. |
| 6,459,935 B1 | 10/2002 | Piersma |
| 6,529,103 B1 * | 3/2003 | Brendel et al. ............. 333/182 |
| 6,545,854 B1 * | 4/2003 | Trinh et al. ................. 361/302 |
| 6,619,763 B1 * | 9/2003 | Trinh et al. ................. 361/302 |
| 2002/0166618 A1 | 11/2002 | Wolf et al. |

* cited by examiner

THERMOPLASTIC POLYIMIDE SUPPORTED TAPE ADHESIVE

ABLELOC (R) 5500
MECHANICAL PROPERTIES

| | TEST METHOD |
|---|---|
| 90° Peel Strength - 250 mil (6.3 mm) width<br>Alloy 42 substrate @ 25°C: 5.0 lb$_r$ (2.3 kg$_r$) peak<br>@ 230°C: 1.4 lb$_r$ (0.64 kg$_r$) peak<br><br>P I Coated Si Substrate @ 25°C: 5.5 lb$_r$ (2.5 kg$_r$) peak<br>@ 230°C: 1.2 lb$_r$ (0.55 kg$_r$) peak | MT-8 |
| Flatwise Tensile Strength - 250 mil² (6.3 mm²)<br>Alloy 42 substrate @ 25°C: 3300 psi (93 kg)<br>@ 230°C: 450 psi (13 kg) | MT-1 |

(1) TH exposure - 16 hours, 85°C/85% RH

FIG. 6

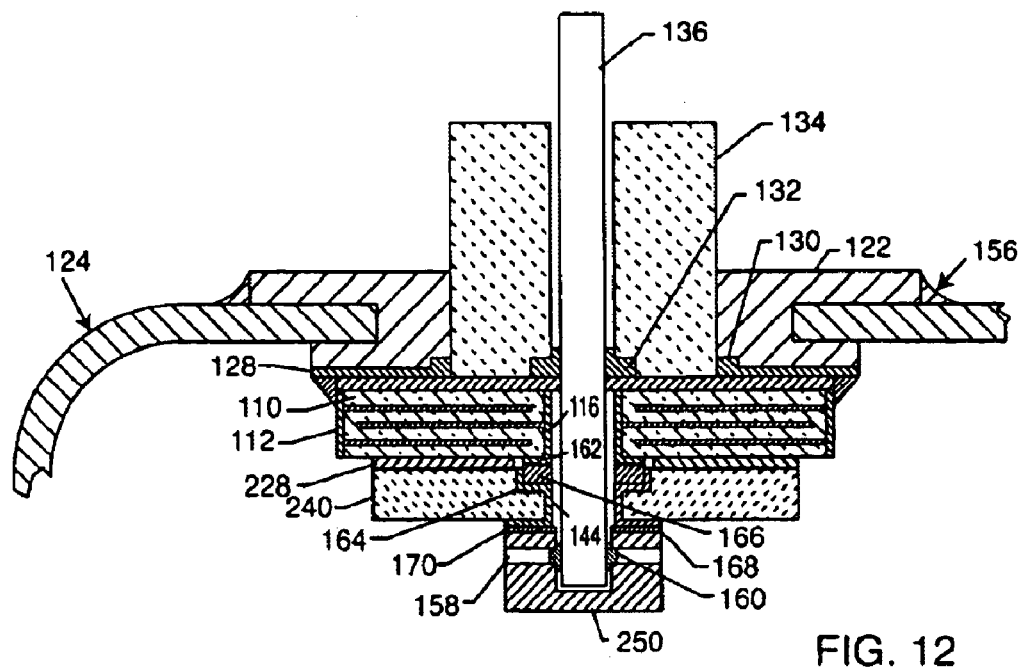
FIG. 12
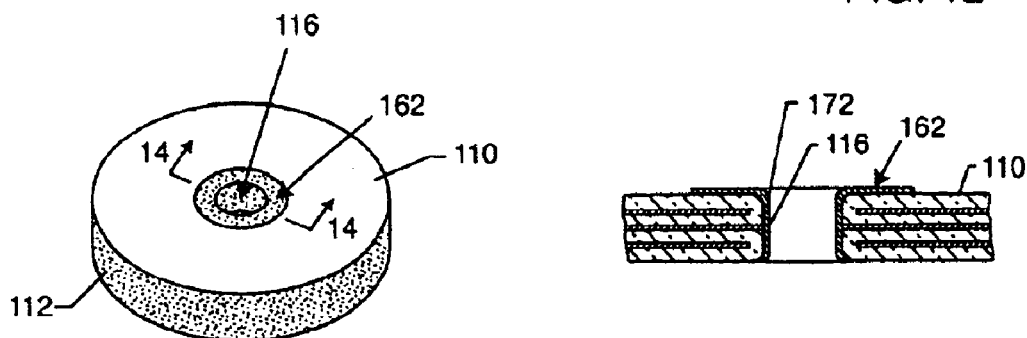
FIG. 13
FIG. 14
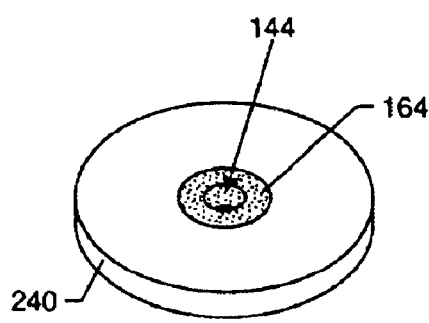
FIG. 15
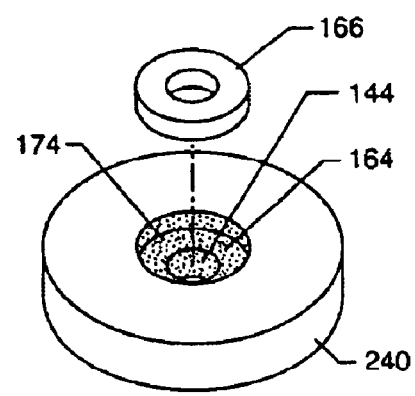
FIG. 16

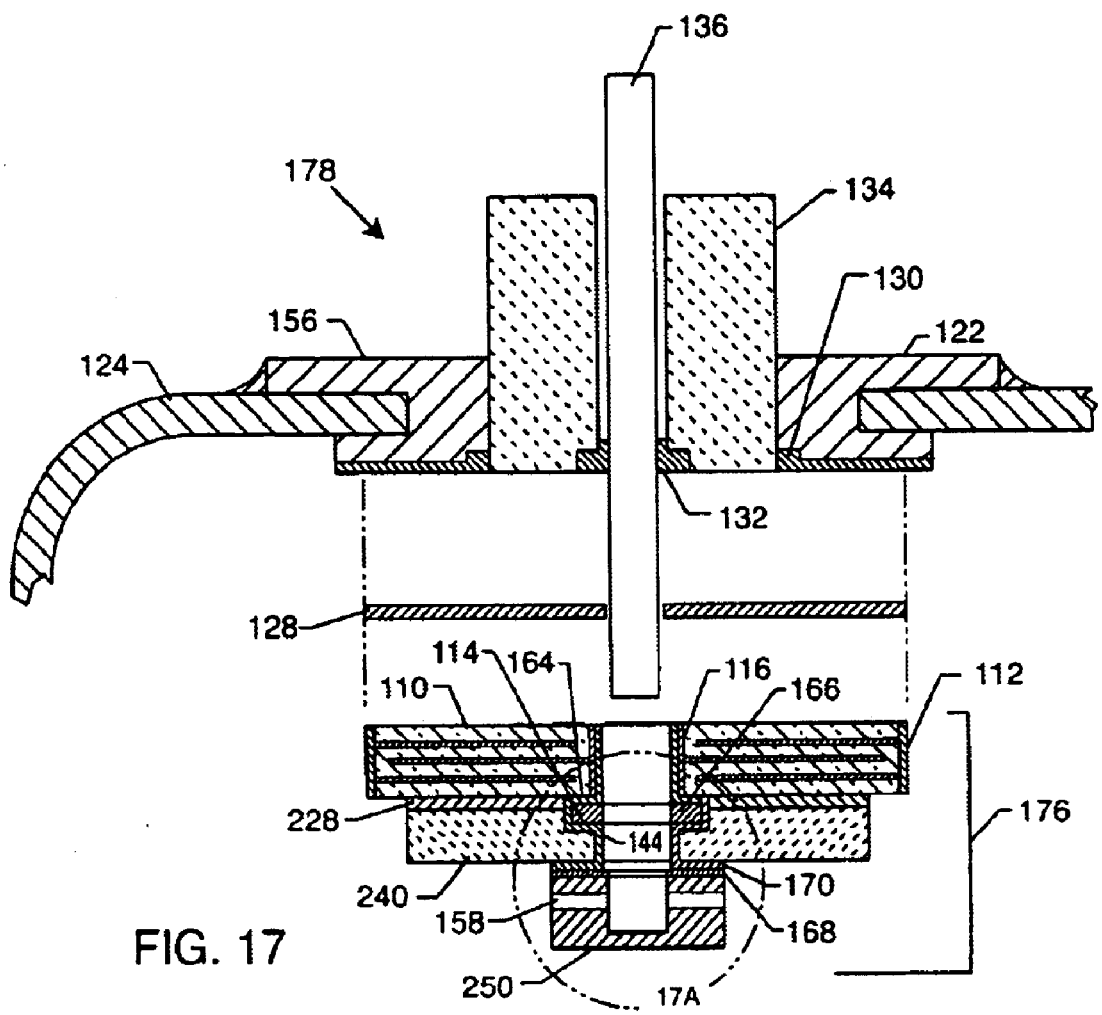
FIG. 17
FIG. 17A
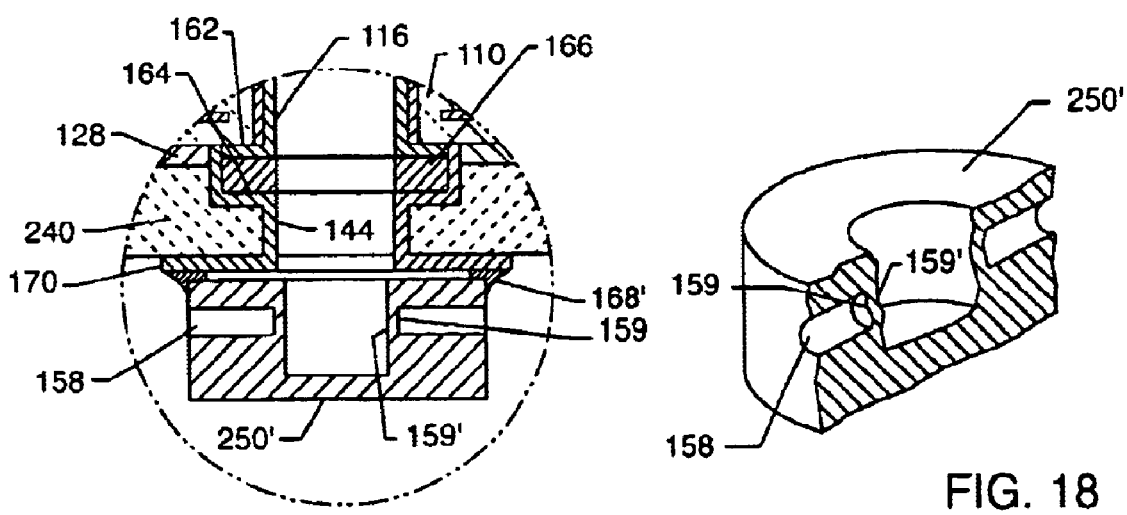
FIG. 18

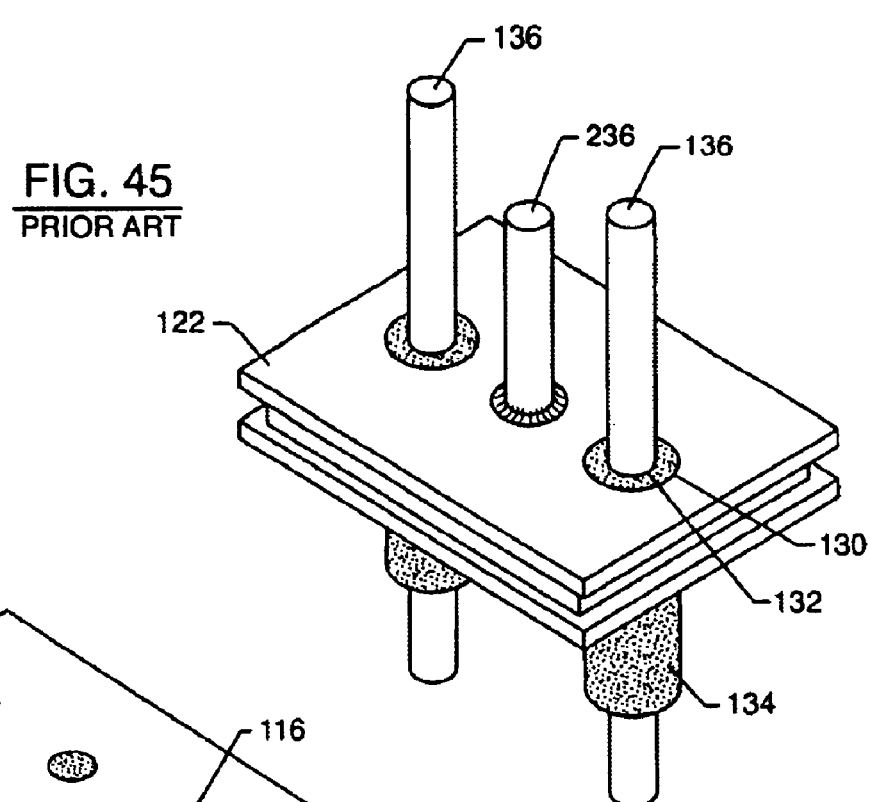
FIG. 45
PRIOR ART
FIG. 46
PRIOR ART
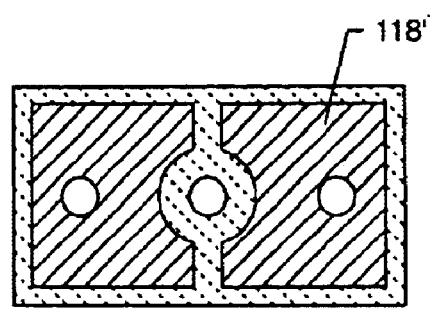
FIG. 47
PRIOR ART
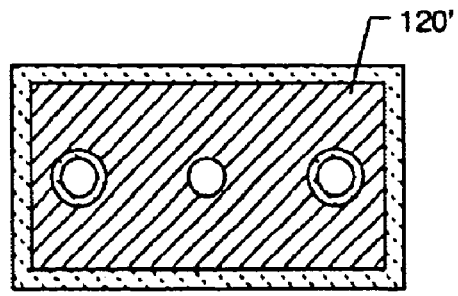
FIG. 48
PRIOR ART

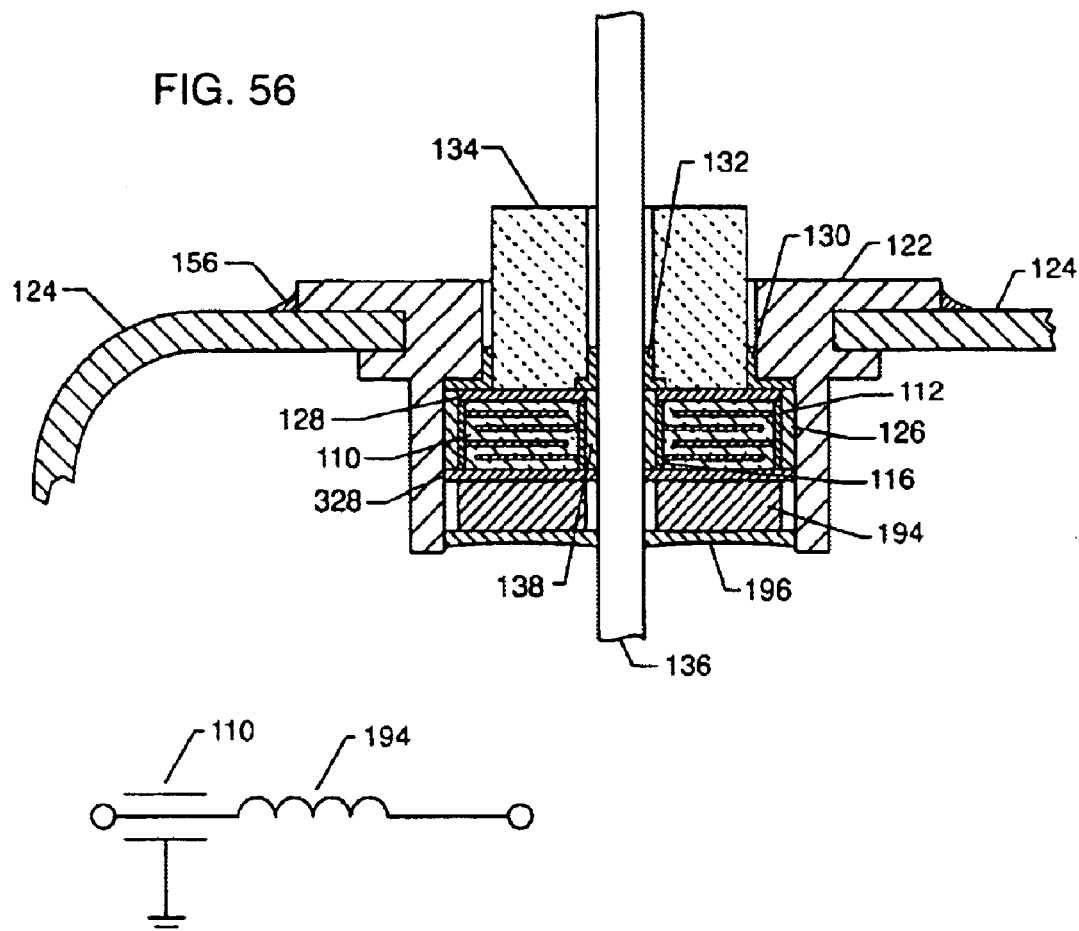
FIG. 56
FIG. 57
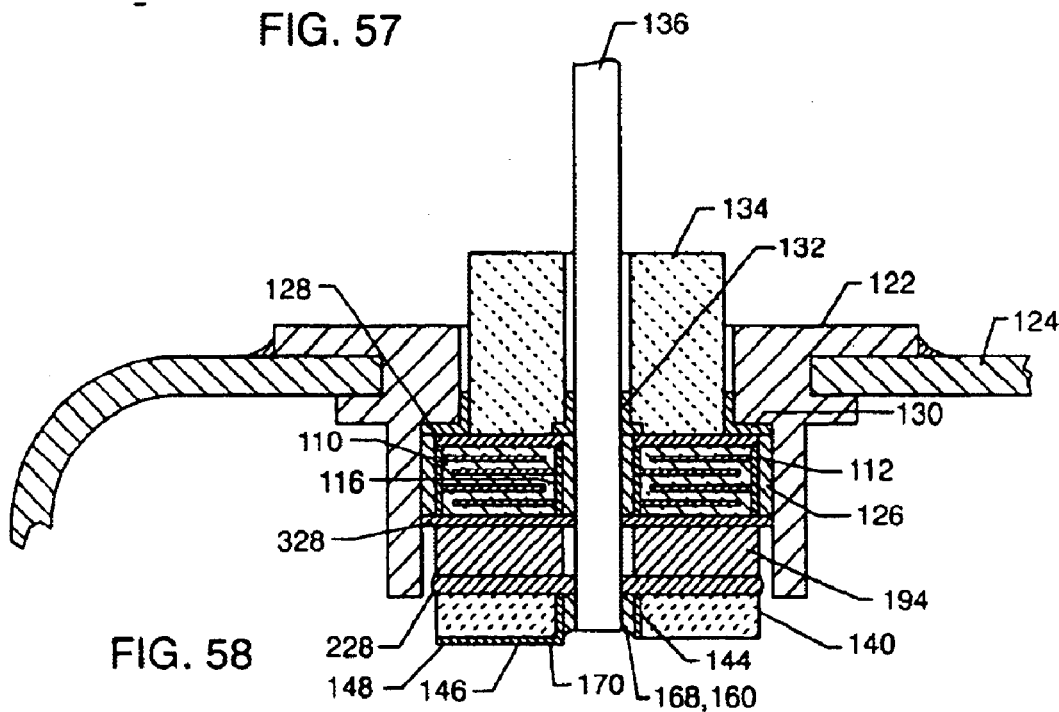
FIG. 58

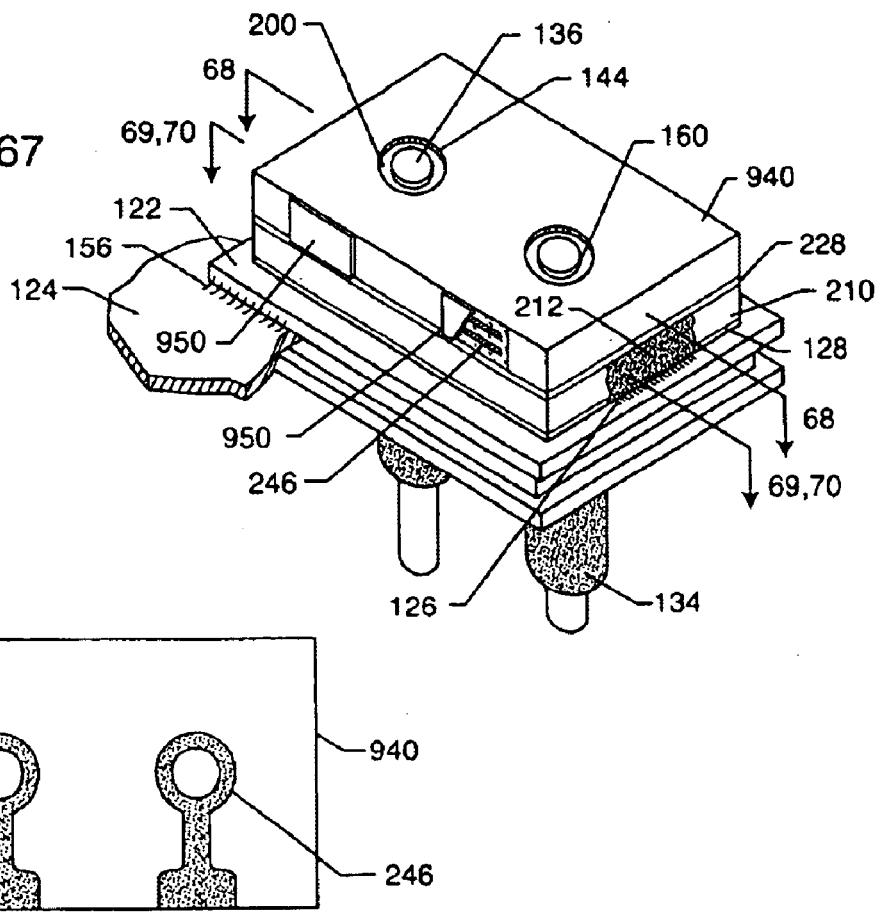
FIG. 67
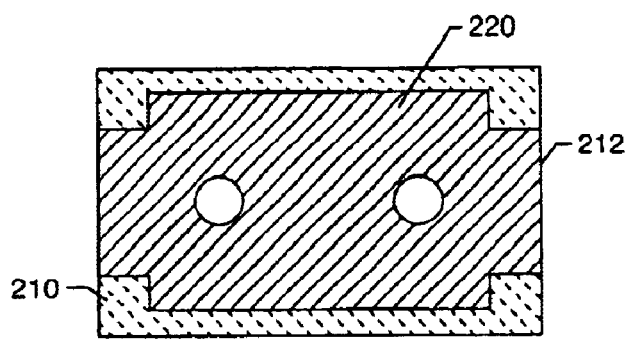
FIG. 68
FIG. 69
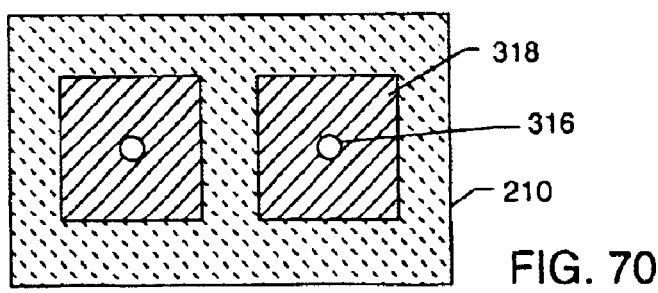
FIG. 70

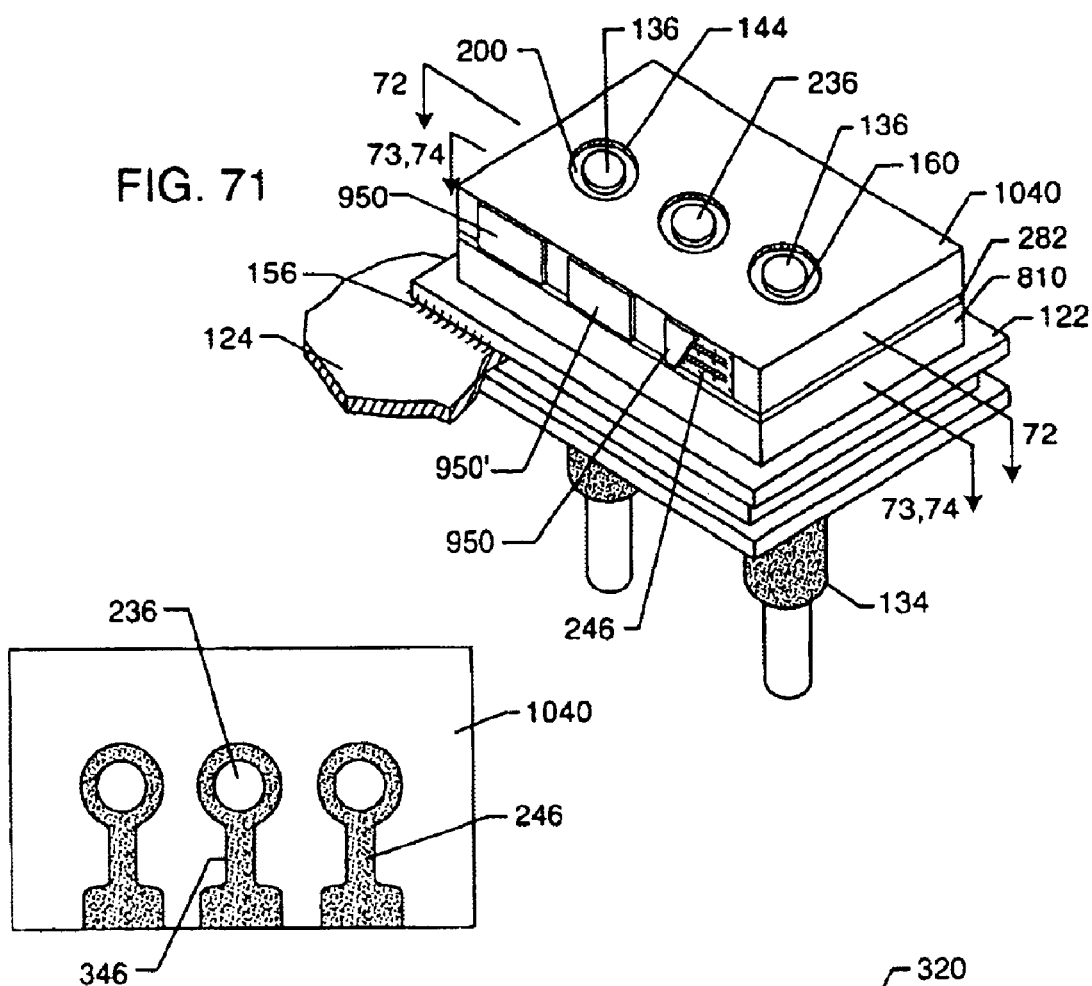
FIG. 71
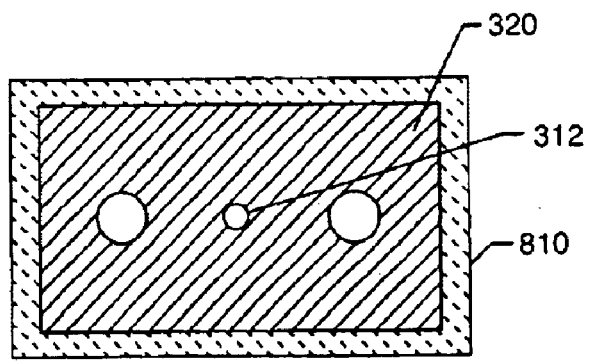
FIG. 72
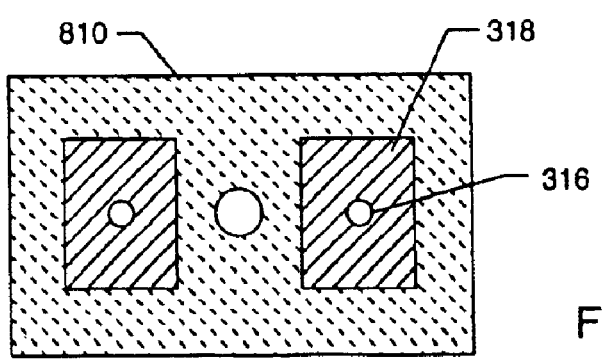
FIG. 73
FIG. 74

EMI FILTER TERMINAL ASSEMBLY WITH WIRE BOND PADS FOR HUMAN IMPLANT APPLICATIONS

RELATED APPLICATION

This application claims priority to U.S. Provisional Patent Application Ser. No. 60/508,426, filed Oct. 2, 2003; and Ser. No. 60/548,770, filed Feb. 27, 2004; and is a continuation-in-part of U.S. patent application Ser. No. 10/377,018 filed Feb. 27, 2003 now U.S. Pat. No. 6,888,715; Ser. No. 10/377,272 filed Feb. 27, 2003 now U.S. Pat. No. 6,765,780; Ser. No. 10/377,086 filed Feb. 27, 2003 now U.S. Pat. No. 6,765,779; and Ser. No. 10/825,900 filed Apr. 15, 2004.

BACKGROUND OF THE INVENTION

This invention relates generally to EMI filter terminal subassemblies and related methods of construction, particularly of the type used in active implantable medical devices such as cardiac pacemakers, implantable defibrillators, cochlear implants, neurostimulators, active drug pumps, and the like and designed to decouple and shield undesirable electromagnetic interference (EMI) signals from an associated device. More particularly, the present invention relates to an improved EMI filter that includes bonding pads for convenient attachment of lead wires by way of thermal or ultrasonic bonding, soldering or the like. The bonding pads can be part of the capacitor structure or be incorporated with a substrate with via holes and/or circuit traces.

Feedthrough terminal assemblies are generally well known for connecting electrical signals through the housing or case of an electronic instrument. For example, in implantable medical devices, the terminal pin assembly comprises one or more conductive terminal pins supported by an insulator structure for feedthrough passage from the exterior to the interior of the medical device. Many different insulator structures and related mounting methods are known for use in medical devices wherein the insulator structure provides a hermetic seal to prevent entry of body fluids into the housing of the medical device. In a cardiac pacemaker, for example, the feedthrough terminal pins are typically connected to one or more lead wires within the case to conduct pacing pulses to cardiac tissue and/or detect or sense cardiac rhythms. However, the lead wires can also undesirably act as an antenna and thus tend to collect stray electromagnetic interference (EMI) signals for transmission into the interior of the medical device. Studies conducted by the United States Food and Drug Administration, Mt. Sinai Medical Center and other researchers have demonstrated that stray EMI, such as RF signals produced by cellular telephones, can seriously disrupt the proper operation of the pacemaker. It has been well documented that pacemaker inhibition, asynchronous pacing and missed beats can occur. All of these situations can be dangerous or life threatening for a pacemaker-dependant patient. In prior devices, such as those shown in U.S. Pat. Nos. 5,333,095 and 4,424,551 (the contents of which are incorporated herein), the hermetic terminal pin subassembly has been combined in various ways with a ceramic feedthrough capacitor filter to decouple electromagnetic interference (EMI) signals to the equipotential housing of the medical device.

In general, the ceramic feedthrough capacitor which has one or more passages or feedthrough holes is connected to the hermetic terminal of the implantable medical device in a variety of ways. In order for the EMI filter feedthrough capacitor to properly operate, a low impedance and low resistance electrical connection must be made between the capacitor ground electrode plate stack and the ferrule, which, in turn, mechanically and electrically connects to the overall conductive housing of the implantable medical device. For example, in a cardiac pacemaker, the hermetic terminal assembly consists of a conductive ferrule generally made of titanium which is laser-welded to the overall titanium housing of the implantable medical device. This not only provides a hermetic seal but also makes the ferrule of the hermetic terminal a continuous part of the overall electromagnetic shield that protects the electronics of the implantable medical device from electromagnetic interference. The ceramic feedthrough capacitor is, in turn, electrically and mechanically bonded to the ferrule of said hermetic terminal. In the past, and, in particular, as described in U.S. Pat. Nos. 5,333,095 and 4,424,551, the connection is typically performed using a thermal setting conductive adhesive. One such material is a silver flake loaded conductive polyimide.

It has been found that the type of conductive particles that are used in the liquid conductive polyimide (or a conductive epoxy) is quite important for proper high frequency performance. A conductive polyimide which is loaded with silver flakes tends to have much lower inductance and lower resistance at high frequency. This is because the silver flakes overlay each other which increases their flake-to-flake contact area. This has been shown to be superior over using silver spheres in that the spheres touch each other only at tangent points. Those tangent points make for a very small electrical contact area, thereby increasing the inductance and resistance of the overall material. This is not readily apparent at low frequency but becomes apparent as the impedance increases at high frequency. For example, in order for the ceramic feedthrough capacitor EMI filter to properly function as a bypass filter at cellular telephone frequencies from 450 megahertz to 3 gigahertz, it is extremely important that the connection material exhibit very low inductance, very low resistance and, therefore, very low impedance at these high frequencies. All of the same points are also applicable to the connection between the lead wires which pass in nonconductive relationship through the hermetic terminal. The inside diameter or feedthrough holes of the ceramic capacitor are electrically and mechanically connected to these feedthrough lead wires. In this way, the filter capacitor can properly decouple high frequency electromagnetic interference.

The amount of solids for silver flake loading tends to be approximately 20–45% of the overall volume of the conductive thermal setting adhesive. For example, in an ideal conductive polyimide, 38% of the constituents by volume would be silver flake, with the balance consisting of liquid polyimide and solvents.

SUMMARY OF THE INVENTION

EMI filter terminal assemblies constructed in accordance with the present invention comprise, generally, at least one conductive terminal pin, a filter capacitor, which in the case of a feedthrough filter capacitor has a passageway through which one or more terminal pins extend, and one or more wire bond pads. An optional ferrite bead or ferrite bead inductor, as described in U.S. Patent Application Ser. No. 60/508,426, can also be included. The feedthrough capacitor is mounted to a hermetic seal subassembly in accordance with one or more prior art methods as described in U.S. Pat. Nos. 4,424,551, and 5,333,095. The feedthrough capacitor has first and second sets of electrode plates also known as the ground electrode plate set and the active electrode plate set. The terminal pin(s) extend through the passageway(s) of the capacitor in conductive relation with the active set of electrode plates. In a typical implantable electronic device application like a cardiac pacemaker, there is a hermetic insulator supported by a conductive substrate (usually a titanium ferrule) in which the terminal pin passes through in nonconductive relation. The capacitor may be bonded onto or into this insulator or separated from the insulator thereby forming a small air gap depending on the assembly method used. The outside diameter of the capacitor is generally installed in conductive relation with the conductive substrate or ferrule so that the feedthrough capacitor is properly grounded. An alternative arrangement is shown in U.S. Pat. No. 5,905,627, entitled INTERNALLY GROUNDED FEEDTHROUGH FILTER CAPACITOR.

In a preferred embodiment, a substrate or circuit board having attached wire bond pads is co-bonded to the ceramic capacitor in such a way that they act as a monolithic structure. The co-bonded circuit board or substrate contains via holes, circuit traces and bonding pads or bonding areas such that it is convenient to attach wires from the circuitry inside the implantable medical device to the feedthrough capacitor structure via thermosonic bonding, ultrasonic bonding, thermal-setting conductive adhesives, soldering, welding, brazing, mechanical attachments or the like. In a preferred embodiment, a novel circuit board or substrate is co-bonded to the top surface of the ceramic feedthrough capacitor in accordance with the invention. The co-bonding is performed with a thin layer of high temperature thermal setting material such as a nonconductive polyimide. Ideal material for this application is a thermal plastic polyimide supported tape adhesive whose properties are described herein in FIG. 6. There are a number of alternate materials that can be used to co-bond the circuit board or substrate to the surface of the ceramic capacitor including various non-conductive thermal-setting polymers such as high temperature thermal setting epoxies, silicones, polyimides, adhesives, sealants and the like. Another method of co-bonding could include co-firing with low temperature glasses, ceramics or the like. The substrate or circuit board can be made of a number of materials that are common in the art. For the present application, an ideal ceramic substrate material would include, but are not limited to the group of: Aluminum-oxide, Fosterite, Alumina in various purities, Berrylia and Aluminum Nitride. These ceramic substrates are well known in the art, have good mechanical or laser scribe characteristics and do not greatly mismatch the thermal coefficient of expansion of the ceramic capacitor and therefore will prevent the formation of excessive mechanical stresses that could fracture the ceramic capacitor. For ceramic substrates, the scribe characteristics of the ceramic material is important so that the individual substrates of the present invention can be cut or snapped out of the larger production array of such substrates.

Non-ceramic printed circuit board materials can also be used as a circuit board substitute for the ceramic substrate of the present invention and are mostly constructed from a resin reinforced by a fabric cloth. Epoxy (FR-4), polyimide and cyanate ester are the more common resin systems in use today. Fiberglass is the most popular fabric.

It is important that the circuit board substrate be able to withstand the high temperatures caused by laser welding of the EMI filtered hermetic terminal assembly with wire bonds into the housing of an implantable medical device. Non-ceramic circuit board temperature range is most often expressed as the glass transition temperature (Tg) of the material. The material's Tg is the point above which the mechanical properties of the material begin to rapidly deteriorate. Printed circuit board materials change from hard, brittle substances to soft, rubber like substances after they reach their glass transition temperature. Typical Tg ratings for the more common material systems are as follows:

|  | Tg |
| --- | --- |
| Polyimides | 260° C.–270° C. |
| Modified Polyimides | 240° C.–260° C. |
| Cyanate Esters | 240° C.–250° C. |
| BT* Epoxies | 225° C.–240° C. |
| Composite Epoxies | 240° C.–260° C. |
| MultiFunctional Epoxies | 160° C.–190° C. |
| TetraFunctional Epoxies | 140° C.–160° C. |
| Modified FR*-4's | 120° C.–130° C. |
| Standard FR*-4's | 115° C.–125° C. |

*BT = Barium Titanate
FR = fiber reinforced

Accordingly, one can see from the above listing, that polyimides, followed by cyanate esters and BT epoxies would be a preferred choice after ceramic substrates as an alternative for the present invention. As used herein, the word substrate or alumina substrate can include any of the ceramic or non-ceramic materials listed above, in addition to many others that are not shown. It is desirable that the material that bonds the substrate of the circuit board to the ceramic capacitor be somewhat flexible and stress absorbing. This flexible layer will help prevent cracking of the ceramic capacitor due to any mismatches in the thermal coefficients of expansion. Accordingly, polyimide is an ideal material in that it forms a ring type of molecule after it goes through its glass transition temperature of approximately 260° C. Compared to epoxy, this material tends to absorb stresses and is quite resilient.

A novel aspect of the present invention is that both the ceramic feedthrough capacitor(s) and the circuit board or substrate can be made much thinner than conventional practice because they are co-bonded into a monolithic laminate structure. This co-bonded/laminated structure is analogous to a beam. By increasing the height of the beam one dramatically increases the moment of inertia of the beam. A beam with an increased moment of inertia is much more resistant to failure or cracking due to bending forces. For example, if there was a bending force which tended to deflect the composite structure in a downward fashion, the top of the capacitor would be in compression and the bottom would tend to be in tension. By raising the moment of inertia of this composite structure, the amount of deflection is minimized. Accordingly, a novel aspect of the present invention is that a circuit board or substrate can be added without greatly increasing the overall volume (height) of the EMI filter.

It is desirable that the circuit board or substrate be relatively thin. This means that materials having a high structural integrity must be used. This is another reason that the use of alumina, aluminum oxide, Fosterite, or polyimide as a substrate material is ideal. The construction of such substrates with circuit trace wire bond pads is well known in the art. Photo resist, chemical etching, automated screen printing, silk screening, selective plating, screen printing and thin or thick film deposition methods are typically used to lay down the conductive circuit trace patterns, the bond pads or "lands" and the location and metallization of via holes. Typical screen printing formulations are generally well known in the art and include, but are not limited to:

| | Screen Printing Ink Formulations |
|---|---|
| | The ink consists of four distinct groups of intermediates, which are thoroughly mixed and blended, yielding a homogeneous product: |
| Functional Phase | Consists of metal powders (Pt, Pd, Ag, Au, etc.) in conductive inks, metals and/or metal oxides ($RuO_2$, $Bi_2Ru_2O_7$, Pd, Ag) in resistors and ceramic/glass ($BaTiO_3$, glass) in dielectric temperature firing. |
| Binder Phase | To hold the ink to the ceramic substrate, and merges with the ceramic during high temperature firing. |
| Vehicle | Acts as the carrier for the powders and is composed of both volatile (solvents) and non-volatile (polymers) organics. These evaporate and burn off during the early stages of drying and firing, respectively. |
| Modifiers | Are small amounts of proprietary additives which control behavior of the inks before and after processing. |

1. Conductor Pastes - Single metal systems (such as, Pd, Ag, Au, Ni, etc.)
2. Conductor Pastes - Binary metal systems (such as, Ag/Pd, Ag/Pt, etc), Tungsten (W), Tungsten/Nickel and equivalent.
3. Conductor Pastes - Ternary metal systems (such as, 40Au/40Pd/20Pt, 60Ag/20Pt/20Pd, 35Ag/25Pd/20Au/20Pt, etc.)
4. High fire systems (such as, 30Ag/70Pd with $BaTiO_3$ or ZrO additives, 100Pd, etc.)
5. Base metal systems (such as, Ni with $BaTiO_3$ or ZrO additives, etc.)

Substrate via holes are typically formed by automated pattern recognition drilling machines. There are a number of methods of providing metallization on the circuit paths, the bonding pads and through the via holes, including screen printing selective plating, metallization vacuum pull through, screen printing, cladding followed by selective etching, physical vapor deposition (PVD), chemical vapor deposition (CVD), and the like. Since these techniques are well known in the art, they will not be completely described herein. In a preferred embodiment of the invention, it is desired to form one or more bond pads suitable for thermal or ultrasonic bonding. In such applications, a gold or gold plated bond pad is desirable. In the preferred embodiment, the bond pad is plated of ultrapure soft gold, such as 99.99% purity. Such gold is also known as yellow gold, is quite soft and to which forming a wire bond is easy. In a typical application, the wire bond pad is laid down directly on the substrate or it can be a Kovar or Alloy 42 attached metal pad with a nickel under-plate and then finished with a soft gold over-plate. Chemical or photo resist techniques, electroplating, electroless plating and the like can be used to prevent deposition of plating, such as the gold, in the wrong places. The bond pad itself is typically Kovar or Alloy 42 but can include many other metals, ceramics and other materials.

Kovar or other metal wire bond pads are preferably attached to the outside or perimeter of the capacitor or a bonded substrate. Another embodiment is to add Kovar wire bond pads surrounding the feedthrough lead wires where a convenient and highly reliable laser weld can be made. Another inventive concept is the addition of a multi-layer substrate with embedded circuit paths. For higher current applications, one or more embedded circuit paths can be added in parallel. In the cross-section of such multi-layer pads the internal circuits can be different on different planes. Another inventive concept is the idea of using the ceramic capacitor itself to directly attach metallized wire bond pads such as gold plated Kovar pads for wire bonding.

It should be noted that if lead-attachment is made by soldering or the like, the Kovar or Alloy 42 pad is generally not required. However, during ultrasonic or thermal wire bonding, considerable energy is imparted into the structure. Accordingly, in this case, a Kovar pad is desired to dissipate energy away from the underlying ceramic substrate or feedthrough capacitor structure. When wire bonding using thermosonic or ultrasonic energy, it is desirable to also use an alumina substrate which is co-bonded to the ceramic capacitor. This alumina substrate, when it is co-bonded, distributes the wire bonding shock and vibration forces across the entire surface of the ceramic capacitor. In general, ceramic materials, and capacitor dielectrics in particular, are strong in compression but very weak in tension. The relatively strong co-bonded alumina substrate helps protect the relatively weak barium titanate, strontium titanate or equivalent high K dielectric used in the ceramic capacitor from fracturing or forming micro-cracks during application of these wire bonding forces. As a general rule, as one raises the dielectric constant, K, of a ceramic material, the structurally weaker it becomes. A low K alumina or aluminum oxide substrate is generally much stronger than barium titanate or other high K ceramics and is able to withstand these wire bonding forces. In this way, tension, shear and impact forces do not build up or become excessive in the capacitor dielectric. Various substrates are well known in the art with wire bond pads and are typically used in combination with hybrid circuit electrical connections and the like.

For implantable medical devices, it is generally required that any of the electrical circuit connections that are in series with the input or output of the device should be of highly reliable connections. For example, in a cardiac pacemaker, the lead wires that are implanted in the heart sense both biologic electrical signals and also provide pacing pulses to correct cardiac arrhythmias. It is generally not acceptable to have an opening or break in this lead wire anywhere in the system that would then be reattached during initial manufacturing with solder, conductive thermal setting adhesives or the like. Accordingly, it is a desirable feature of the present invention to have a laser welded connection between a Kovar or Alloy 42 pad and the hermetic terminal lead wire, and/or a gold, gold alloy or CuSil (copper-silver alloy) braze between the Kovar pads and the perimeter or outside diameter of the substrate or capacitor. The connection from the feedthrough capacitor wire bond pad is generally accomplished by ultrasonic or thermosonic bonding of a pure gold wire directly to the pure gold plating of the pad. Attachment of lead wire(s) to wire bond pads can also be accomplished by soldering, conductive polymers, welding, brazing or a variety of mechanical attachment methods including machine screws and the like. In a typical pacemaker application, this pure gold wire is approximately 0.005 inch in diameter and would terminate on a similar wire bond pad on the pacemaker hybrid circuit substrate or circuit board on which microprocessor wire bonding and other implantable medical device electronics are mounted. Automated wire bonding equipment is readily available and well known in the art.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 6 is a table specifying the properties of a thermal plastic polyimide supported tape adhesive;

FIG. 12 is a sectional view similar to FIG. 9 illustrating another embodiment of the invention;

FIG. 13 is an inverted perspective view of the feedthrough capacitor illustrated in FIG. 12;

FIG. 14 is an enlarged sectional view taken generally along the line 14—14 of FIG. 13;

FIG. 15 shows the alumina substrate of FIG. 12;

FIG. 16 illustrates an alternative embodiment of the alumina substrate of FIG. 15, incorporating a circular boss into which a counterbore holds an electrical connection material;

FIG. 17 is an exploded sectional view of the structure shown in FIG. 12, illustrating assembly of the hermetic terminal;

FIG. 17A is an enlarged, fragmented cross-sectional view of the area illustrated by the line 17A in FIG. 17;

FIG. 18 is an enlarged, fragmented perspective and cross-sectional view of the wire bond pad of FIG. 17;

FIG. 45 is a perspective view of a prior art hermetic terminal with a grounded lead wire;

FIG. 46 is a perspective view of a prior art internally grounded bipolar feedthrough capacitor;

FIG. 47 is a cross-sectional view through the capacitor of FIG. 46, illustrating a configuration of active electrode plates therein;

FIG. 48 is a cross-sectional view through the feedthrough capacitor of FIG. 46, illustrating the configuration of ground electrode plates therein;

FIG. 56 is a fragmented perspective view of a two-element or L-section filter;

FIG. 57 is an electric schematic diagram of the filter shown in FIG. 56;

FIG. 58 illustrates the L-section filter of FIG. 56 modified in accordance with the present invention;

FIG. 67 illustrates yet another hermetic terminal embodying the invention, wherein a multi-layer substrate containing embedded circuit traces is utilized;

FIG. 68 is a cross-sectional view through the multi-layer substrate taken generally along the line 68—68 of FIG. 67;

FIG. 69 is a cross-sectional view taken generally along the line 69—69 of FIG. 67, illustrating the configuration ground electrode plates within the capacitor;

FIG. 70 is a cross-sectional view generally taken along the line 70—70 of FIG. 67, illustrating the configuration of active electrode plates within the capacitor;

FIG. 71 is a perspective view similar to that illustrated in FIG. 67, but utilizing an internally grounded feedthrough capacitor as shown and described in relation to FIGS. 45–49;

FIG. 72 is a sectional view generally along the line 72—72 of FIG. 71, illustrating the configuration of circuit traces through the co-bonded substrate;

FIG. 73 is a cross-sectional view taken generally along the line 73—73 of FIG. 71, illustrating the configuration of ground electrode plates within the capacitor;

FIG. 74 is a cross-sectional view taken generally along the line 74—74 of FIG. 71, illustrating the configuration of active electrode plates within the capacitor;

DETAILED DESCRIPTION OF THE PREFERRED EMBODIMENTS

Reference will now be made in detail to presently preferred embodiments of the invention, examples of which are represented in the accompanying drawings for purposes of illustration. Such examples are provided by way of an explanation of the invention, not a limitation thereof. In fact, it will be apparent to those skilled in the art that various modifications and variations can be made in the present invention, without departing from the spirit and scope thereof. For instance, figures illustrated or described as part of one embodiment can be used on another embodiment to yield a still further embodiment. Still further, variations and selection of materials and/or characteristics may be practiced, to satisfy particular desired user criteria. Thus, it is intended that the present invention cover such modifications and variations as come within the scope of the present features and their equivalents. In the following description, functionally equivalent components of the various embodiments will be assigned the same reference number, or, if similarly related, a similar reference number increased by 100, for example, for sake of clarity and ease of explanation.

Figure 1:
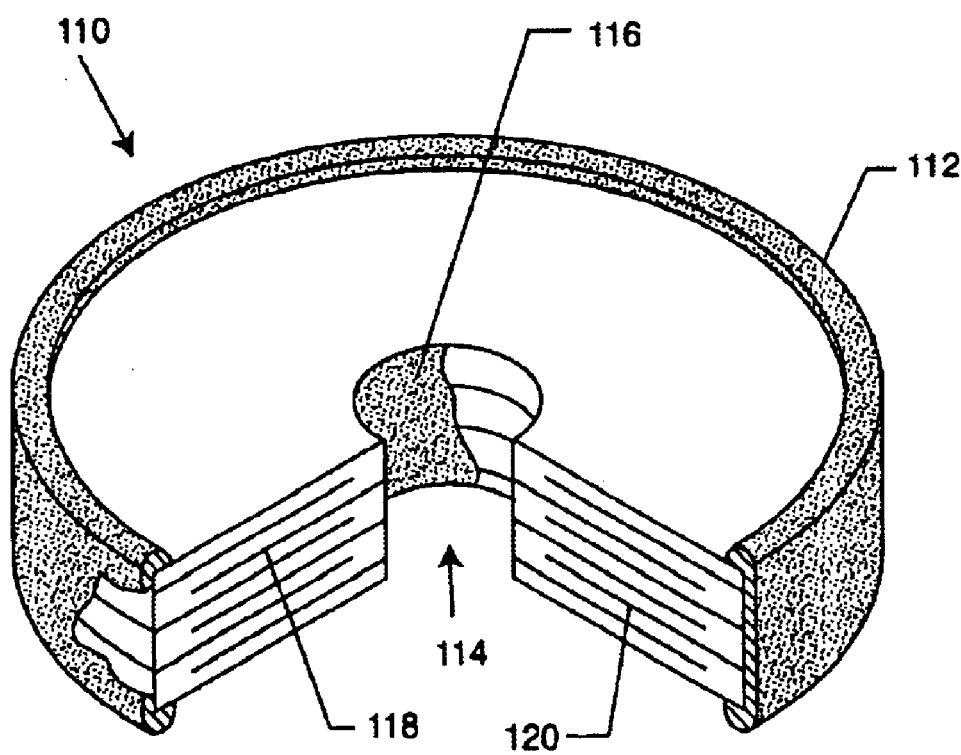
FIG. 1 is a cutaway perspective view of a prior art unipolar ceramic feedthrough capacitor.

FIG. 1 is a cut away perspective view of a prior art unipolar ceramic feedthrough capacitor 110. This capacitor 110 has a conventional external ground 112 formed by the conductive termination around its outside diameter. This is a conductive termination which would be electrically connected to the ferrule of the hermetic terminal of an implantable medical device. The inside diameter hole 114 is also metallized 116 for electrical connection to the lead wire that passes through the center passageway 114. One can see in the cut away the active 118 and ground 120 electrode plate sets. Feedthrough capacitor geometry is highly preferable for EMI filters in that it acts as a coaxial broadband transmission line filter. This means that a feedthrough capacitor offers effective attenuation over a very broad range of frequencies without the series resonance problem that plagues conventional rectangular monolithic ceramic chip capacitors.

Figure 2:
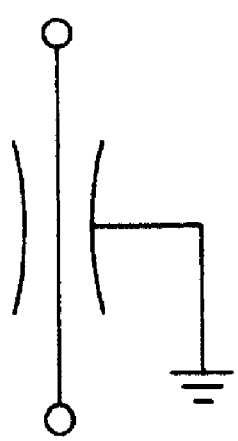
FIG. 2 is an electric schematic diagram of the feedthrough capacitor of FIG. 1.

FIG. 2 is the schematic diagram of the feedthrough capacitor of FIG. 1.

Figure 3:
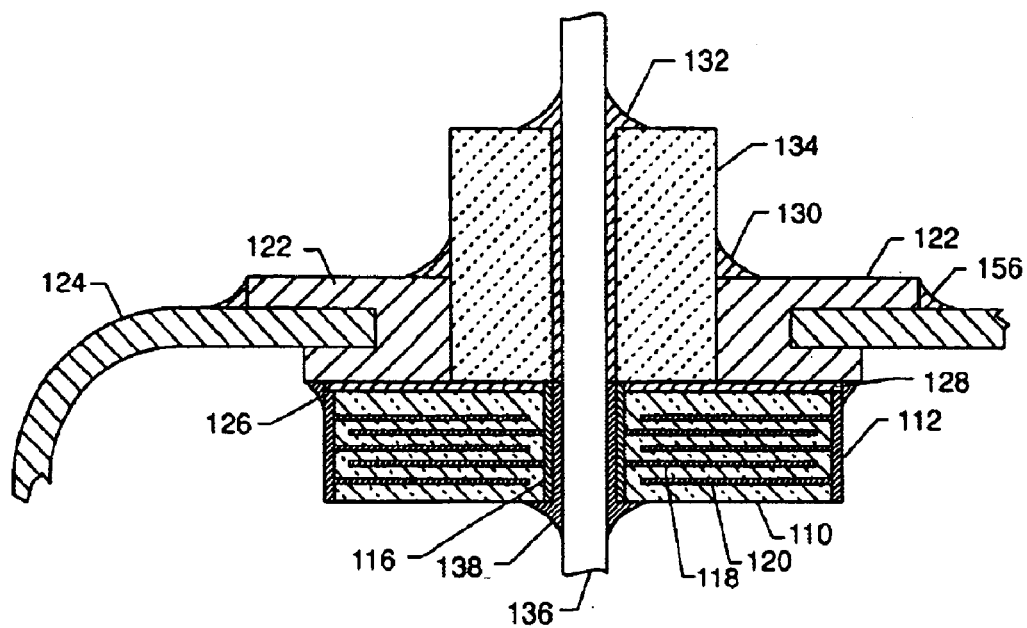
FIG. 3 is a fragmented cross-sectional view of the feedthrough capacitor of FIG. 1 installed to a hermetically sealed ferrule.
Figure 4:
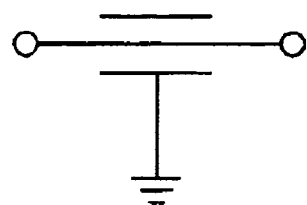
FIG. 4 is an electric schematic diagram for the filter shown in FIG. 3.

FIG. 3 is a cross-section drawing which illustrates the feedthrough capacitor 110 of FIG. 1 installed to the hermetically sealed ferrule 122 of a housing 124 of an implantable medical device in accordance with U.S. Pat. No. 5,333,095, entitled FEEDTHROUGH FILTERED CAPACITOR ASSEMBLY FOR HUMAN IMPLANT. This device is also referred to as a unipolar (one lead wire) EMI filtered hermetic terminal. It is also known as a one section single element EMI filter. The schematic diagram for the filter is shown in FIG. 4. It is possible to have multielement EMI filters (combinations of inductors and capacitors) with a single (unipolar) lead wire, or have multiple lead wires with a single element EMI filter (feedthrough capacitor only). The connection between the outside diameter metallization 112 of the feedthrough capacitor 110 and the ferrule 122 is accomplished with a thermal setting conductive adhesive 126. In the preferred embodiment, connection 126 is typically not a continuous connection 360 degrees around the entire outside diameter of the ceramic capacitor 110. The electrical connection material 126 is usually discontinuous to allow for helium leak detection and also to minimize thermal and mechanical stresses to the capacitor 110.

The capacitor 110 is surface mounted and bonded to the ferrule 122 of the hermetic terminal using an adhesive backed polyimide supported washer 128, which is further described in FIG. 6. The hermetic terminal of FIG. 3 is formed by gold brazes 130 and 132. Braze 130 makes a 360 degree mechanical and hermetic seal between the ferrule 122 and the alumina ceramic insulator 134. Gold braze 132 forms a 360 degree mechanical and hermetic seal between the lead wire or terminal pin 136 and the alumina ceramic terminal 134. The capacitor ground electrode plates 120 are connected in parallel to the capacitor outside termination 112. The capacitor ground electrode plates 120, in turn, are connected to the ferrule 122 by way of the electrical connection material 126 disposed between the capacitor metallization 112 and the surface of the ferrule 122. In a typical medical implant EMI filter, the material 126 is of the group of solder, braze, or a thermal setting conductive polymer such as conductive polyimide or conductive epoxy. The electrical connection is made between the capacitor inside diameter metallization 116 and the lead wire 136 with connection material 138, which is typically of the same material described above with respect to connection material 126. If the lead wire 136 is of solderable material, which, for human implant applications, includes the group of platinum and platinum iridium biocompatible alloys, then material 138 can be solder, conductive thermal setting adhesives or the like. However, in the case where the lead wire 136 is of niobium, tantalum or titanium, solders and conductive adhesives generally cannot be applied directly to such pin materials. In this case, the pin 136 would need pretreatment in order to eliminate contact problems associated with high resistance surface oxides.

Figure 5:
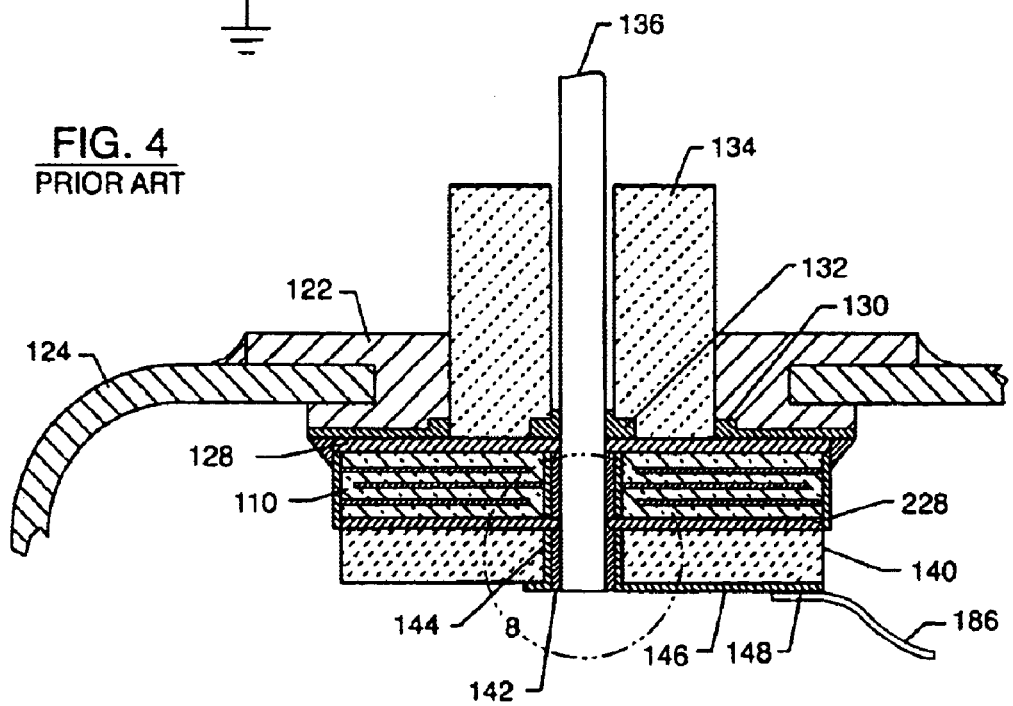
FIG. 5 is a sectional view similar to FIG. 3, illustrating a circuit board or substrate co-bonded to the capacitor.

FIG. 5 is the unipolar feedthrough capacitor 110 of FIG. 3 with a circuit board or substrate 140 co-bonded to the capacitor 110. The substrate 140, in a particularly preferred embodiment, is a thin alumina or aluminum oxide ceramic or equivalent insulative disk. A thin layer of nonconductive polyimide 228 bonds the alumina substrate 140 to the monolithic ceramic feedthrough capacitor 110. In the preferred embodiment, a conductive thermal setting polymer, solder or braze joint 142 electrically connects the inside diameter metallization 144 of the via hole through the ceramic substrate 140 to the lead wire 136. In turn, this also connects lead wire 136 by way of the via hole metallization 144 to a continuous circuit trace 146 to the wire bond pad area 148 which is more readily seen in FIG. 7. The wire bond pad area 148 generally consists of a pure gold layer which is thick enough for conventional wire bonding. A lead wire 186 is shown attached to bond pad area 148 by thermosonic wire bonding. Lead wire 186 can then be routed to AIMD internal circuits (not shown).

It should be pointed out that in human implant applications, the purpose of the hermetic terminal is to allow conductive lead wires 136 to pass in nonconductive relationship through the titanium housing or can 124 of the pacemaker or implantable cardioverter defibrillator. Accordingly, all materials used on the body fluid side of such can or housing must be biocompatible. This limits the materials that can be used to noble metals, titanium, stainless steel and the like. Usually the lead wire 136 shown in FIG. 5 would be of platinum, platinum-iridium alloy, tantalum, niobium or the like. If the lead 136 is platinum or platinum-iridium, these are highly solderable materials and therefore, it is easy to form a well wetted solder joint or conductive polymer connection between the inside diameter metallization 144 of the alumina substrate 140 and the outside diameter of the lead wire 136. However, if the lead wire is constructed of tantalum or niobium, these materials are generally not easily wetted by solder or conductive polymers. This can complicate the solder or conductive polymer joint 142 shown in FIG. 5 and its exploded view in FIG. 8. This is because niobium and tantalum form a heavy oxide layer on their surfaces. Accordingly, a niobium or tantalum lead wire 136 must be pretreated so that a solder joint or connection 142 with a conductive thermal setting material can be accomplished. It is a feature of the present invention to pretreat such leads such that they can be reliably electrically connected to via hole metallization 144 of the substrate 140. U.S. Pat. No. 6,159,560 describes a method of depositing silver on a tantalum pin to displace surface oxide and deposit a conductive finish suitable for making an electrical connection. There are other pin metal coating methodologies, including sputter or vacuum deposition (as described in U.S. Pat. No. 5,531,003), of materials such as gold, titanium and other conductors which can then be followed up with surface plating with gold, iridium or the like.

FIG. 6 is a Table which specifies the properties of a thermal plastic polyimide supported tape adhesive 228 which is ideal for laminating the substrates 140 of the present invention to the ceramic capacitor 110 surface. The industry designation for this is ABLELOC(R)5500. This is the same polyimide supported tape adhesive 128 that is generally used to bond the ceramic capacitor 110 to the surface of the hermetic terminal 122. This material is convenient in that it can be die cut, stamped or laser cut into convenient geometries to co-bond an alumina substrate 140 to the capacitor 110 or bond the capacitor to a hermetic terminal 122. In addition, polyimide is an ideal high-temperature material that will readily withstand the installation stresses into the implantable medical device caused by laser welding. A number of other bonding materials can also be used including adhesives, epoxies, glasses and the like.

Referring now back to FIG. 5, the cross-sectional view of the alumina substrate 140 illustrates a top circuit trace metallization layer 146. Metallization 146 is continuous from the inside diameter via hole of the substrate 144 all the way over to the wire bond pad area which is shown in cross-section FIG. 5 as 148.

Figure 7:
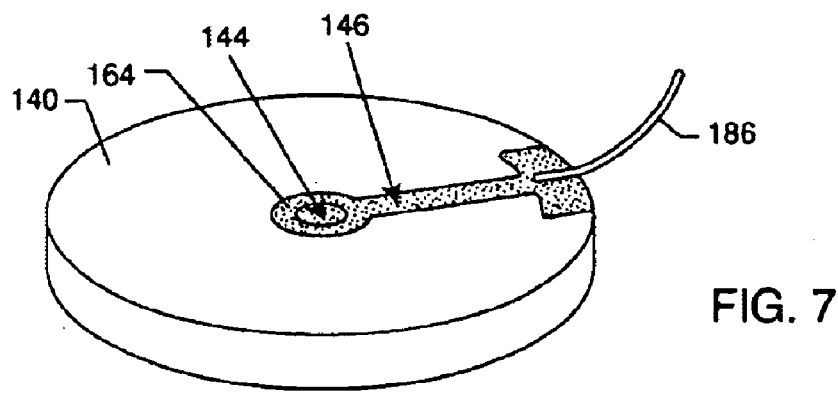
FIG. 7 is a perspective view of the circuit board or substrate illustrated in FIG. 5.

FIG. 7 better illustrates the circuit board or substrate 140 that is co-bonded to the feedthrough capacitor 110 as previously described in FIG. 5. It should be noted that in FIG. 7 the circuit board or substrate 140 is shown inverted so that the wire bond area 148 and circuit trace(s) 146 can be readily observed. The circuit trace 146 is conductive and metallic in nature. The wire bond pad area 148, in the preferred embodiment, is finished with high purity gold suitable for thermal or ultrasonic bonding of a gold lead wire to the circuitry inside the implantable medical device. In the preferred embodiment, the substrate 140 is made of a solid highly insulative material like ceramics such as alumina, aluminum oxide or Fosterite. This solid insulative substrate 140 is then co-bonded to the barium titanate ceramic capacitor 110 as previously described in FIG. 5 using a thermal plastic polyimide supportive tape adhesive 228 such as described in FIG. 6 and shown in FIG. 5.

Referring now again to FIG. 5, the plated or metallized through via hole 144 is shown installed over lead wire 136. It is important to note that the electrical connection using material 142 between the feedthrough wire 136 and the inside diameter metallization 144 of the circuit board or substrate is very important. The electrical connection material 142, such as solder, conductive polyimide, conductive epoxy or the like, desirably penetrates into the angular space between the inside diameter of the metallized hole 144 of the substrate 140 and the outside diameter of the lead wire 136. This puts the electrical connection material 142 in shear as opposed to having just an electrical connection on top. This is very important to make a highly reliable electrical connection.

A significant deficiency in previous designs, such as U.S. Pat. Nos. 6,031,710 and 5,870,272 and 5,867,361, is that the series connection between the lead wire and the wire bond pad depends on a large mass of solder in series. This is not an optimal situation. It has been known in U.S. Space programs for a number of years that a designer should not rely on solder, conductive epoxies or the like in a large mass which could later result in an open circuit during use. For lead wire connections, it is generally a NASA policy to have a mechanical connection before a solder joint is formed. This is particularly important in a spacecraft application where such electrical connections are subjected to high shock and vibration forces. However, a similar situation occurs during ultrasonic wire bonding. By nature of the ultrasonic bonding process, significant vibration forces are set up on the wire bond pad which can transmit to the electrical connection material 142. Accordingly, as seen in FIG. 5, a highly reliable "in shear" electrical connection using material 142 is made between the inside diameter metallization 144 of the circuit board or substrate 140 and the lead wire 136.

Figure 8:
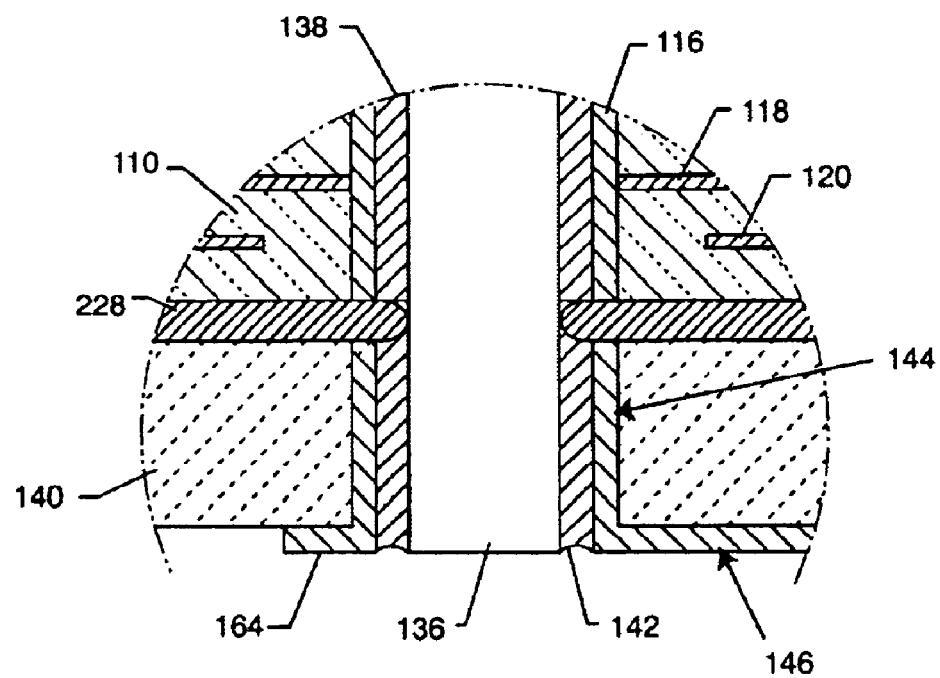
FIG. 8 is an enlarged view of the structure of area "8" of FIG. 5.

As mentioned, FIG. 8 is an enlarged cross-section view of FIG. 5 showing the detail of the electrical connection between lead wire 136 and the via hole metallization 144 of substrate 140 more clearly. In a previous operation, this ceramic substrate 140 has been selectively metallized so that its through hole or via has conductive termination or plating 144 on the inside diameter. There is a continuous metallic electrical connection 146 between the inside diameter metallization of the via hole 144 all the way over to the bond pad area 148 (which is not visible in FIG. 8). An important point is that the electrical connection material 142 is in shear between the lead wire 136 and the inside diameter metallization 144 of substrate 140. Material 142 is of the group of solder, thermal setting conductive adhesives, such as a thermal setting conductive polyimide, braze or the like. As can be seen in FIG. 8, the electrical connection material 142 forms a 360 degree electrical connection joint around the lead wire 136 and a 360 degree joint around the metallized inside diameter 144 of the substrate 140. This forms a highly reliable electrical connection in that material 142 has a large wetted surface area that is in shear. In addition, the relative volumes of materials are such that the solder or conductive thermal setting adhesive is used properly. In a very large mass, high tensile stresses can develop as solder brazes or conductive adhesives shrink or when their thermal coefficients of expansion are mismatched with the surrounding materials (such as the relatively weak barium titanate ceramic capacitor 110). If solder is used to make the electrical connection 142 in FIG. 8, then it would be desirable if the solder is malleable, such as a high lead content solder. A preferred alloy would be alloy SN10, which is a common Kester solder. In addition, the metallized circuit trace 146 as seen in FIG. 7 forms a continuous metallized surface from the inside diameter metallization 144 of the via hole all the way to the wire bond pad area 148. Accordingly, the electrical connection from wire bond pad 148 through the circuit trace 146 to the inside diameter of the via hole 144 is continuous, conductive and highly reliable.

Referring now back to FIG. 7, the wire bond pad area 148 is not an ideal surface for attachment of a lead wire by conventional thermosonic or ultrasonic bonding processes. It is preferred that a metallic wire bond pad made of Kovar, Alloy 42 or similar materials be used, as will be more fully described herein. It is well known in the art that these Kovar pads are nickel plated and then over-plated with an ultra-pure soft gold. The thermal or ultrasonic bonding of a pure gold lead wire is facilitated by the mating together of the two gold surfaces.

Wire bond attach area 148 need not be gold plated if the subsequent lead wire connection is to be made by soldering, welding, brazing or the like. In this case, the wire attach area could be tin, electro-tin plating, solder coat and the like.

Figure 9:
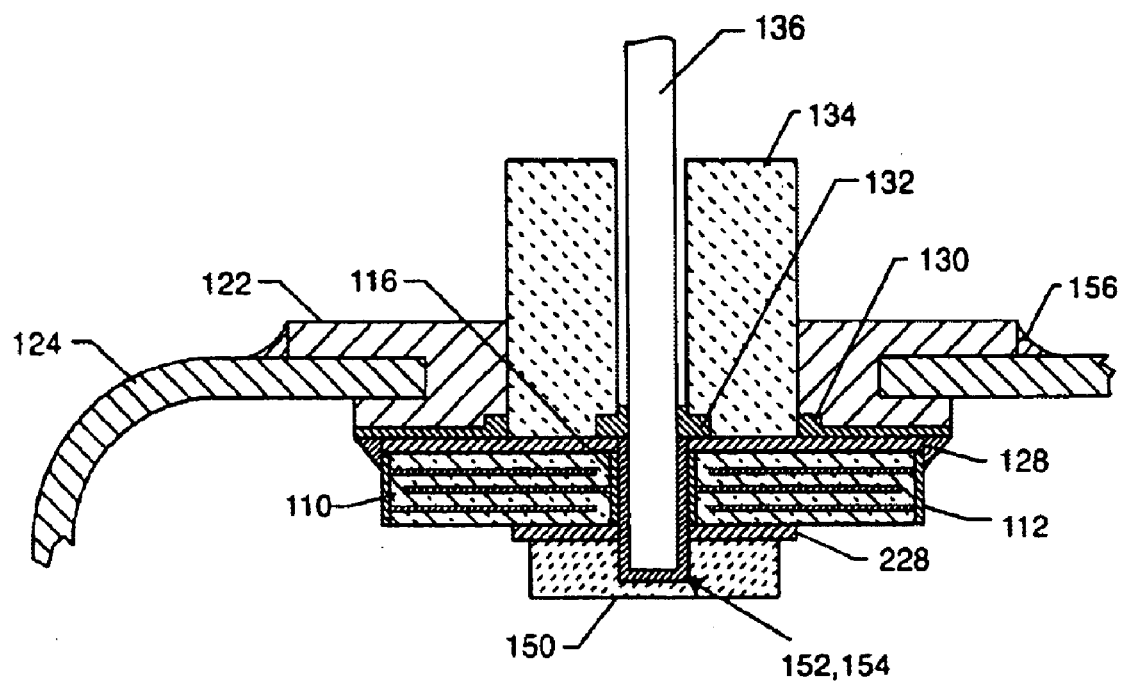
FIG. 9 is a sectional view similar to FIG. 5, illustrating use of a wire bond pad bonded or laminated onto the top of the capacitor over a shortened lead wire.

A novel method of providing a wire bond pad 150 is shown in FIG. 9. In this case, a counterbored Kovar or Alloy 42 disk, as also shown in FIGS. 10 and 11, is bonded or laminated 228 onto the top of capacitor 110 over a shortened lead wire 136 by soldering, conductive thermal-setting adhesives, resistance welding, laser welding material 154 or the like.

Figure 10:
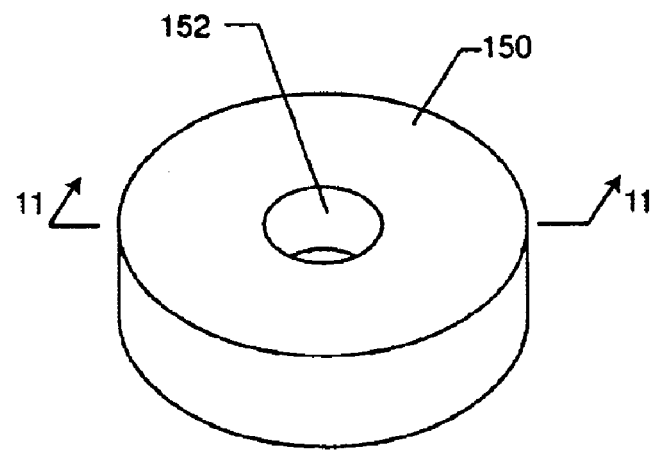
FIG. 10 is an enlarged perspective view of the wire bond pad of FIG. 9.
Figure 11:
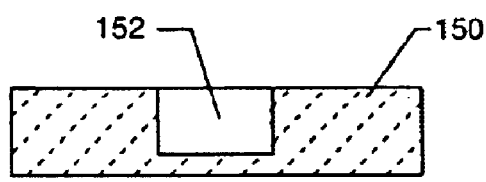
FIG. 11 is a sectional view taken generally along the line 11—11 of FIG. 10.

FIG. 10 is an isometric view of the wire bond cap 150 and FIG. 11 is a cross-sectional view of the wire bond cap 150 of FIG. 9. In the preferred embodiment, such wire bond cap 150 as shown in FIGS. 9 and 10 would be constructed of Kovar or Alloy 42. The Kovar would be nickel plated and then over plated with soft gold suitable for compatibility with ultrasonic, thermal or thermal sonic wire bonding processes. As discussed in the FIGS. 5 and 8 drawing descriptions, electrical connection material 154 is preferably placed in shear between the wire bond pad 150 and the lead wire 136. Again, this is essential to form a highly reliable electrical connection that will withstand the vibration and shock forces associated with subsequent ultrasonic wire bond attachment(s). This shear area is accomplished by the counterbore area 152 shown in FIGS. 10 and 11. The wire bond cap 150 of FIG. 10 is also described in pending U.S. patent applications Ser. Nos. 10/377,018, 10/377,272 and 10/377,086. FIGS. 44, 45, 46, 47A, 47B, 47C, 48 and 49 from pending U.S. patent application Ser. No. 10/377,086, entitled, EMI FEEDTHROUGH TERMINAL ASSEMBLY FOR HUMAN IMPLANT APPLICATIONS UTILIZING OXIDE RESISTANT BIOSTABLE CONDUCTIVE PADS FOR RELIABLE ELECTRICAL ATTACHMENTS, describes alternate methods to build the wire bond cap 150 shown in FIGS. 10 and 11.

In FIG. 9, an alternative method of forming the electrical connection 154 between the counterbore 152 of wire bond cap 150 and lead wire 136 is by prior art resistance welding techniques. In resistance welding, the counterbore 152 of wire bond cap 150 would fit very tightly onto lead wire 136. Electrical contacts would be placed on the outside diameter of wire bond cap 150 and a current pulse from the resistance weld machine would be applied sufficient to cause heating and reflow of metals and/or the plating of wire bond cap 150 to form a low resistance metallurgical bond to lead wire 136.

Referring now back to FIG. 9, as illustrated, electrical connection material 154 also makes a reliable and oxide free electrical connection to the gold braze area 132. This important feature is described by co-pending U.S. patent application Ser. No. 10/377,086. The gold braze material 132 penetrates through any surface oxidation on lead wire 136, for example, if lead wire 136 is niobium or tantalum, and thereby forms a highly conductive and reliable hermetic seal connection. In turn, electrical connection material 154 also makes an electrical connection to the inside diameter metallization 116 of feedthrough capacitor 110 and to the gold plated counterbore area 152 of the Kovar wire bond cap 150. This means that lead wire 136 can be of any biocompatible material including oxidized materials such as niobium, and that no pretreatment, for example, sputter coating, is required to make a reliable electrical connection from lead wire 136 to the feedthrough capacitor inside diameter metallization 116 or to the gold plated wire bond cap 150. In other words, no direct electrical contact from the capacitor inside termination 116 or the wire bond cap 150 is required to lead wire 136.

FIGS. 12 and 17 illustrate another embodiment of the present invention. As previously mentioned, it is highly desirable in the output and input circuitry of implantable medical devices, that all electrical connections that are in series with the input and output be of highly reliable metallurgical joints. In other words, it is generally unacceptable to have a conductive thermal setting polymer, conductive polyimide, or less reliable metallurgical joint such as solder to rely on in series with the lead wires that are connected, for example, to the human heart. Mechanically robust and reliable metallurgical joints are preferred and are generally of the group of laser welding, brazing and the like. A preferred embodiment illustrated in FIGS. 12 and 17, overcomes such deficiencies with a wire bond pad 250 that has been modified to accommodate laser beam welding. Another advantage of using this laser weld approach is that lower cost hermetically sealed feedthrough terminals can be used. Lower cost means that the lead wires can be of niobium or tantalum construction instead of relatively expensive platinum or platinum-iridium alloys. Niobium and tantalum are notorious for forming heavy oxides on their surface and generally do not readily accept solder or thermal setting conductive adhesives. Previous methods of making the electrical contact with niobium or tantalum lead wires include an expensive process of pre-treating the niobium with vacuum or sputter deposition processes or other metallic overcoating. Such overcoat materials can be platinum, gold and the like.

FIGS. 12 and 17 overcome all of these previous deficiencies with the novel assembly method as illustrated. FIG. 12 is similar to the unipolar hermetic terminal assembly of FIG. 5 with a metallic ferrule 122. Co-bonded to this assembly is a prior art ceramic feedthrough capacitor 110. The ferrule 122 is designed to be laser welded 156 into the housing 124 of an implantable medical device such as a cardiac pacemaker or implantable cardioverter defibrillator (ICD). Gold braze 130 forms a hermetic seal connection between the ferrule 122 and the alumina insulator 134. The gold braze material 132 makes the hermetic connection between the lead wire 136 and the hermetic alumina insulator 134. It will be obvious to one skilled in the art that the alumina insulator 134 could be replaced by a variety of glasses or other sealing materials. The mounting of the unipolar capacitor 110 to this terminal is in accordance with prior art U.S. Pat. No. 5,333,095 and others. In FIG. 12, one can see that the alumina substrate 240 of the present invention is placed on top and co-bonded 228 to the ceramic capacitor 110. A counterbored wire bond cap 250 is placed over the top of the co-bonded alumina substrate 240 as shown. It is a novel aspect of the Kovar cap that it have one or more side through holes 158. These holes 158 are designed so that a laser beam from a laser welder can be directed into the through hole 158 to impinge its energy upon the lead wire 136. Accordingly, a highly reliable laser weld connection 160 is formed between the counterbored wire bond cap 250 and the lead wire 136.

Another novel aspect of the assembly shown in FIG. 12 is the fact that no electrical connection is needed from the inside diameter termination 116 of the feedthrough capacitor 110 and the lead wire 136. This is because there is an electrical connection from a bottom termination surface 162 of the feedthrough capacitor 110 to a corresponding top termination surface 164 of the alumina substrate 240. The electrical connection material 166 joining these two surfaces can be solder, conductive thermal setting adhesives and the like. In turn, the wire bond cap 250 has been previously gold brazed 168 to a metallized surface 170 of the alumina substrate 240 as shown. As mentioned, the wire bond cap 250 is first gold brazed using a gold braze preform 168 to the metallization 170 that is on the surface of the alumina substrate 240. The laser weld 160 is then made by projecting a laser beam through the holes 158 in the wire bond cap 250.

This is better understood by examining FIGS. 13 through 16. FIG. 13 is an inverted isometric view of the feedthrough capacitor 110. One can see the typical inside diameter metallization 116. An important feature is the circular surface metallization band 162 which forms a continuous electrical connection with the inside diameter termination 116. In a preferred embodiment, the capacitor 110 would be tumbled either in the green or fired state prior to metallization application so that the sharp transmission corner from the passage hole to the surface is rounded. This makes for a more reliable electrical connection between the top circular metallization 162 and the inside diameter metallization 116. FIG. 14 is an enlarged cross-section taken along line 14—14 of FIG. 13, which illustrates the rounded corner 172. A sharp, non-tumbled square corner could cause the metallization 116-162 to pull away during firing and becoming undesirably thin and discontinuous at the sharp edge. Such condition could lead to high resistance or even loss of circuit continuity.

Referring now to FIG. 15, one can see an alternative embodiment of the alumina substrate 240. In this embodiment, the alumina substrate 240 has an inside diameter or via hole metallization 144 which forms a continuous electrical connection with a similar circular metallization stripe 164. FIG. 16 illustrates an alternative embodiment of the alumina substrate 240 of FIG. 15 which incorporates a circular boss 174 into which a counterbore holds an electrical connection material 166. This boss also appears in FIG. 12. Electrical connection material 166 can be either a thermal setting conductive adhesive, solder a gold braze preform or the like. This gold brazed preform 166 is designed to seat against the metallized surface 164 of the alumina substrate 240. The wire bond cap 250 is pre-assembled by gold braze 168 to a circular metallized band 170 on the opposite side of the alumina substrate 240 as shown in FIGS. 12, 15 and 16. Referring now back to FIG. 12, one can see in the sandwiched construction that the capacitor circular metallization band 162 is electrically connected through material 166 to the corresponding metallization band 164 of the alumina substrate 240. After the wire bond cap 250 is gold brazed to the opposite side metallization surface 170 of the alumina substrate 240, there is then a continuous electrical connection from the inside diameter metallization of the feedthrough capacitor 116 through the inside diameter via hole metallization 144 of the substrate 240 all the way to its top metallization 170 and in turn, to the wire bond cap 250. The rest of the electrical circuit is completed by the laser weld connection between the wire bond cap 250 and the lead wire 136 shown as 160.

This assembly technique is further illustrated in FIG. 17 and offers a number of important advantages which include the ability to make a reliable electrical connection to niobium, tantalum or other leads that are notorious for forming a heavy oxide. Another advantage is the ability to pre-assemble the wire bond cap 250 to the alumina substrate 240 to the feedthrough capacitor 110 and test and inventory this piece as a sub-assembly 176. This sub-assembly 176 is shown in FIG. 17. The most expensive part of the hermetically sealed filtered terminal is the hermetic seal feedthrough 178 without a capacitor 110. This consists of the assembly of the lead wire 136 to the alumina insulator 134 to the ferrule 122 which is hermetically and mechanically connected by gold brazes 130 and 132. In this way, a large quantity of the hermetic terminal 178 assemblies can be built and kept in inventory. A quantity of the pre-assemblies 176 can also be built and kept in inventory. The capacitance value determined by the feedthrough capacitor 110 varies anywhere in human implant applications from 25 picofarads to around 9000 picofarads. In one cardiac pacemaker application alone, the capacitance value can vary from approximately 1000–9000 picofarads. Accordingly, it is an advantage to be able to inventory various capacitance values of the pre-assembly 176 and keep them in inventory ready to be installed by co-bonding 128 and laser welding to the hermetic terminal 178 and then final tested and shipped.

The pre-assembly 176 consists of the following manufacturing operations:

Step 1. Machine the Kovar wire bond pad 250 and then prepare it by nickel plating followed by pure gold plating as a final finish.

Step 2. Manufacture or purchase the alumina substrate 240, including tungsten, molybdenum, gold or equivalent metallization through its via hole 144, which extends onto the top and bottom surfaces of the alumina as circular metallized areas 164 and 170.

Step 3. Attach the wire bond pad 250 to the alumina substrate 240 with a gold braze preform 168 sandwiched in between the surface metallization 170 on the alumina substrate 240 and the wire bond pad 250.

Step 4. Reflow the gold braze perform 168 in a vacuum brazing furnace which metallurgically and electrically bonds the wire bond cap 250 to the metallization 170 of the alumina substrate 240.

Step 5. Select a capacitor 110 of the appropriate capacitance value and size from inventory.

Step 6. Place a polyimide supported insulating washer 228 with an enlarged center hole sandwiched on the opposite side of the alumina substrate 240.

Step 7. Load electrical connection preform 166 which is a thermal setting conductive adhesive, solder preform or the like.

Step 8. Place the capacitor 110 on top of the aforementioned preform 166, forming the sandwich construction shown as subassembly 176.

Step 9. Co-cure or reflow the nonconductive laminating material or polyimide based insulating washer 228, at elevated temperature along with the electrical connection material 166.

Step 10. The subassembly consisting of the capacitor 110, the insulative bonding washer 228, the alumina substrate 240, and the Kovar wire bond pad 250 is then electrically tested and inventoried as subassembly 176.

This a significant advantage in that the most costly part of the overall filtered hermetic terminal is the hermetic terminal feedthrough assembly 178. By using the pre-assembly technique 176, as described in FIG. 17, substantial cost can be saved. A large quantity of the standardized hermetic terminal assemblies 178 can be maintained. When there is an order for a particular capacitance value, one can just select the related pre-assembly 176 and quickly install it onto the hermetic terminal.

Step 11. Select appropriate hermetic seal and capacitor pre-assemblies 176 and 178 from inventory and insert a sandwiched nonconductive adhesive backed polyimide supported tape adhesive washer 128.

Step 12. Cure the adhesive backed polyimide washer 128. This bonds the ceramic capacitor pre-assembly 176 to the hermetic terminal assembly 178.

Step 13. Laser weld the wire bond cap 250 to the lead wire 136 through one or more holes 158 in wire bond cap 250. This is typically performed by an automated robotic laser welder. Comparison of the wire bond cap 250 shown in FIG. 17 to the improved wire bond cap 250' shown in FIGURES. 17A and 18 reveals that a thin metal wall 159–159' has been formed during machining. This preferred embodiment allows the laser welder beam to impinge upon wall 159–159' thereby welding this material to lead wire 136 (weld not shown).

Step 14. Final electrical testing and packaging for shipment.

FIG. 17A illustrates an alternative method of making an electrical attachment 168' from the wire bond pad 250 to the metallization 170 of substrate 240. Referring back to FIG. 17, wire bond cap 250 was electrically and mechanically attached to the substrate 240 by reflowing a gold preform 168 between wire bond cap 250 and the metallization 170 which is part of substrate 240. Referring now to FIG. 17A, the wire bond cap 250 has been electrically and mechanically attached to the metallization 170 of the substrate 240 using a conductive polyimide solder or the like shown as 168'.

In FIG. 18 one can see the laser weld holes 158. In step 13 above, the laser beam is directed through this hole 158 which impinges upon the lead wire 136 thereby forming the laser weld joint 160. As shown in FIG. 18, this laser weld 160 can be performed from one or more sides, achieving a very mechanically strong and low resistivity connection 160. An alternative method is shown in cross-sectional view 19. In the enlarged cross-sectional view FIG. 19A of FIG. 19, one can see that the wire bond pad 250 has had its laser through hole 158' enlarged at the opening point. This can be done by a counter sink, counterbore or the like. In this way, it is easier to direct the laser beam energy against the lead wire 136 thereby facilitating formation of the laser weld connection 160 between the wire bond cap 250 and the lead wire 136. This can be done on one or more sides around the circumference of the wire bond cap. As stated, the laser weld hole 158', shown in FIG. 19, has a counterbore which enlarges the opening for the laser beam. This enlarged opening also facilitates easier fixturing and robot programming to form the laser weld 160 between the wire bond cap 250 and the lead wire 136. In this particular embodiment, the lead wire 136 can be of a non-wettable material such as niobium or tantalum. As one can see, there is an electrical connection material 168 which attaches the wire bond cap 250 directly to the capacitor top metallization 162. Capacitor top metallization 162 is continuous and also forms a termination surface 116 all around the inside diameter of the capacitor 110 feedthrough hole. The capacitor 110 depicted in FIG. 19 requires no additional electrical connection between the lead wire 136 and the feedthrough capacitor inside diameter termination 116. This is because there is continuous electrical connection from the capacitor active electrodes 118, to the capacitor inside diameter metallization 116 to the capacitor top circular termination 162 through electrical connection material 168 to the wire bond cap 250 and in turn by laser weld 160 to the lead wire 136. This forms a highly reliable and low impedance electrical connection suitable for the EMI filtering purposes of the feedthrough capacitor 110. The electrical connection material 168 between the wire bond cap 250 and the capacitor circular metallization stripe 162 can be of solder, thermal setting conductive adhesives, brazes or the like. The assembly shown in FIG. 19 does not require an intermediate substrate 140 or 240 as described in previous FIGURES.

Figure 19:
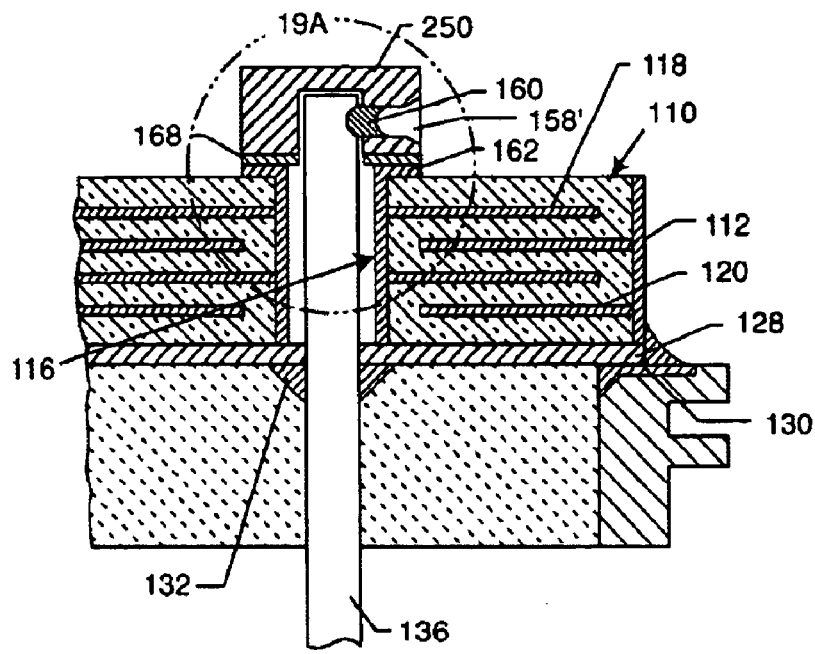
FIG. 19 is a partially fragmented sectional view similar to FIG. 17, illustrating use of an alternative wire bond pad.
Figure 19A:
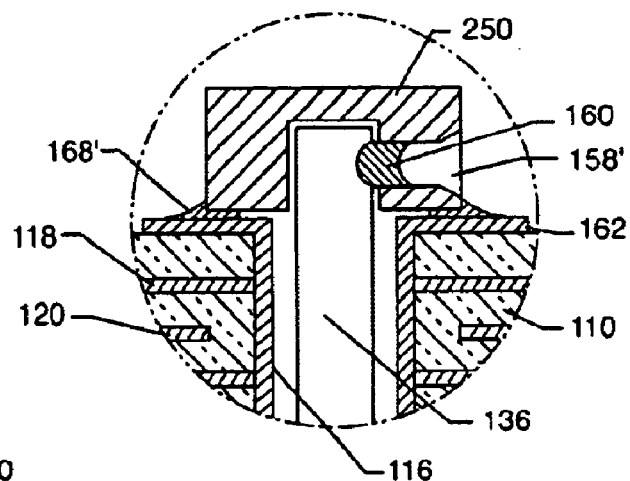
FIG. 19A is an enlarged, fragmented cross-sectional view of the area 19A of FIG. 19, illustrating an alternative configuration of components.

FIG. 19A illustrates an alternative method of attaching the wire bond cap 250 to the top metallization 162 of the ceramic capacitor 110. Referring back to FIG. 19, wire bond cap 250 is attached to the top capacitor metallization 162 through a sandwiched electrical connection consisting of either gold braze, solder, conductive thermosetting adhesives or the like. Referring now to FIG. 19A, the electrical connection material has been relocated as shown. In this case, 168' would typically not be a gold braze but of the group of solder, conductive polyimide or conductive epoxy.

Figure 20:
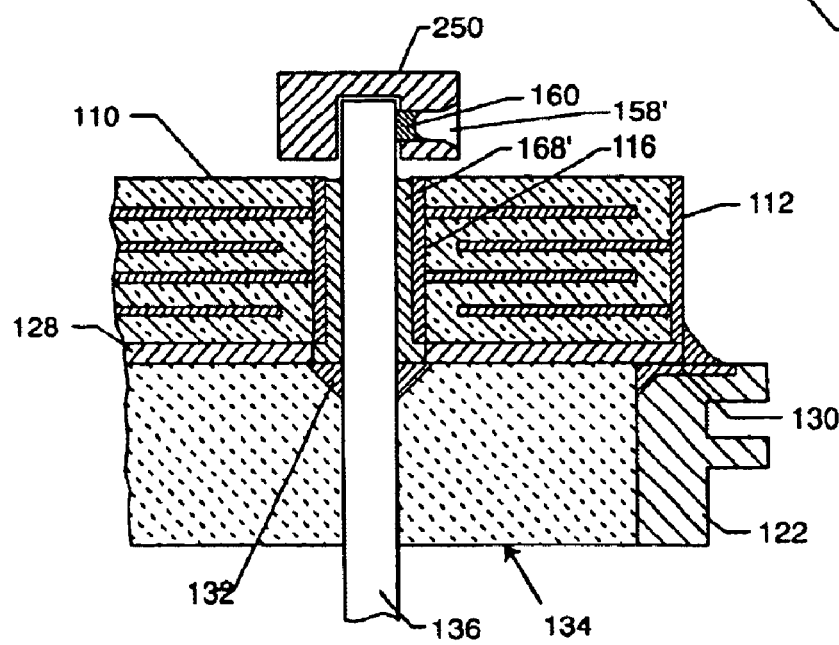
FIG. 20 is a view similar to FIG. 19, illustrating an alternative embodiment of the wire bond cap.

FIG. 20 illustrates an alternative embodiment of the wire bond cap 250 of FIG. 19. A laser weld joint 160 is formed in the same manner as previously described for FIG. 19. However, in this case, there is no top metallization 162 as a circular stripe on top of the capacitor 110. This has been removed along with the material 168 or 168' that formed an electrical connection between the wire bond cap 250 and the top metallization 162 of the FIG. 19 capacitor. In this embodiment, the electrical connection material 168' is only between the lead wire 136 and the capacitor inside diameter metallization 116. An insulating material, such as a polyimide supported tape adhesive 128, has been placed between the capacitor 110 and the alumina of the hermetic seal 134 to prevent material 168' from leaking out underneath the capacitor 110 and shorting it out to the conductive ferrule 122. If the lead wire 136 were of platinum iridium or pure platinum or similar highly solderable alloy, then no additional electrical connection is required. However, in the case where the lead wire 136 is of a tantalum, niobium or other easily oxidizable material, then insulating material 128 would be pulled back away from the lead wire 136, as shown, so that the electrical connection material 168' penetrates down and contacts to the gold braze 132 of the hermetic seal 134. This forms an oxide free electrical connection and is the subject of a pending U.S. patent application Ser. No. 10/377,086, the contents of which are incorporated herein.

Figure 21:
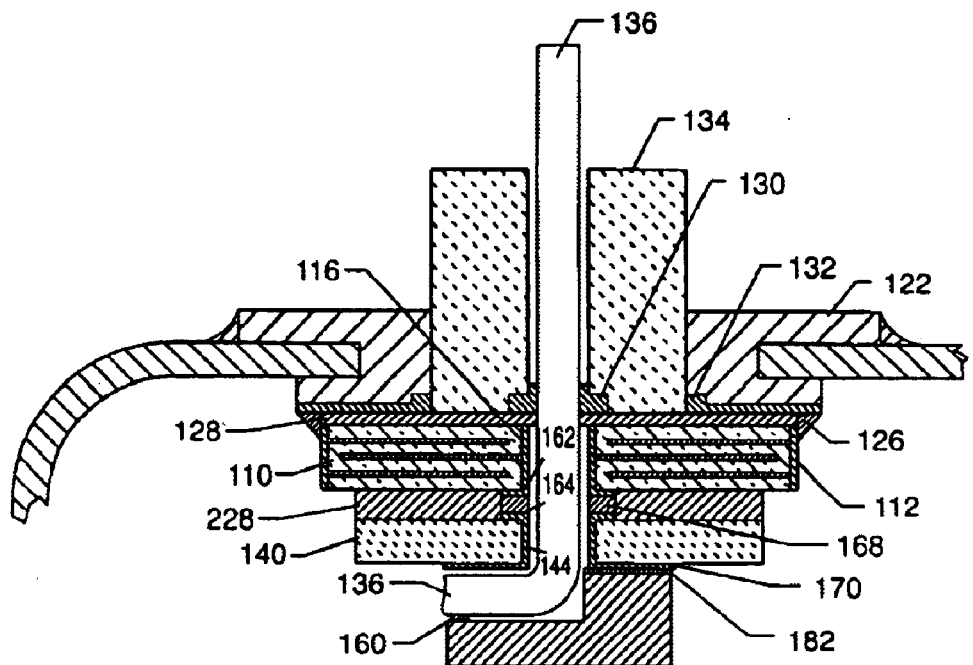
FIG. 21 is a fragmented cross-sectional view similar to FIG. 12, illustrating yet another alternative wire bond pad.
Figure 22:
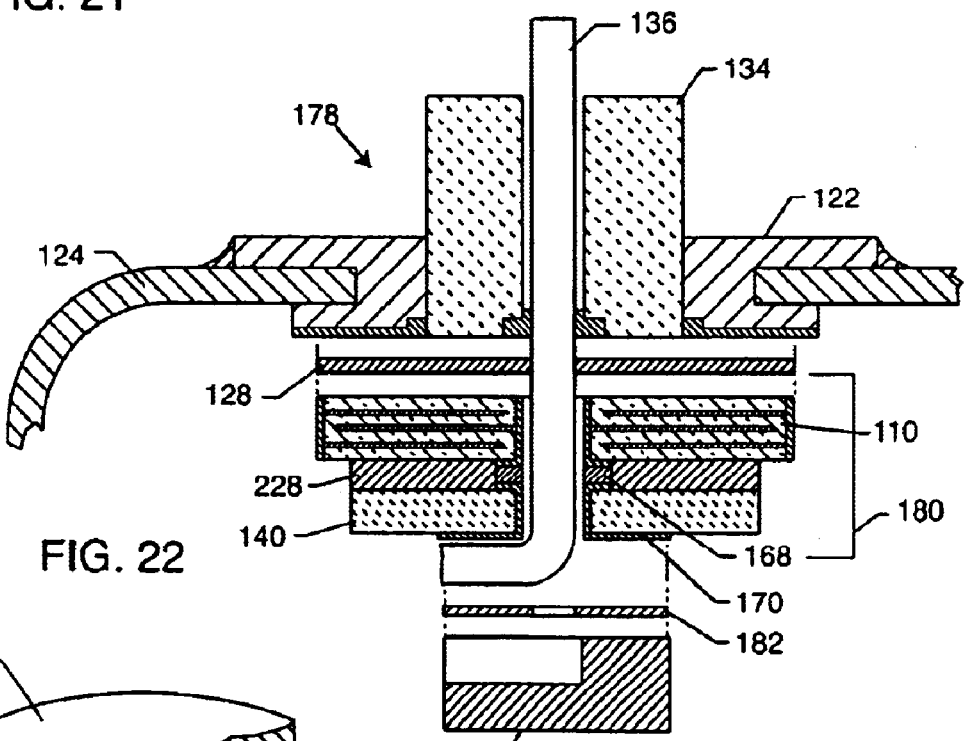
FIG. 22 is an exploded, assembly view of the EMI filter hermetic terminal assembly of FIG. 21.

FIG. 21 is the EMI filtered hermetic terminal assembly of FIG. 12 with the wire bond pad 350 modified as shown. This embodiment is better understood by examining FIG. 22, which is an exploded view taken from FIG. 21. Referring to FIG. 22, a subassembly 180 is pre-manufactured by bonding the ceramic feedthrough capacitor 110 to the alumina substrate 140 of FIG. 15. As previously described, electrical connection material 168 connects the inside diameter metallization 116 of the capacitor 110 to the inside diameter metallization 144 of the via hole of the substrate 140. After curing bonding washer 228, the pre-assembly 180 is placed onto the hermetic terminal assembly 178 consisting of hermetic gold braze joints 130 and 132, alumina insulator 134, lead wire 136 and ferrule 122. The ceramic capacitor pre-assembly 180 is then bonded to the aforementioned hermetic terminal assembly 178 by means of polyimide supported adhesive washer 128. After curing washer 128, lead wire 136 is bent over at a 90 degree angle as shown in FIGS. 21 and 22 thereby allowing the wire bond cap 350 to be bonded to the top metallization 170 of substrate 140 using a thermal setting conductive adhesive, gold braze or solder shown as material 182.

Referring now back to FIG. 21, the completed assembly is shown except for the remaining step which is to form the laser weld connection 160 which connects the lead wire 136 to the wire bond cap 350. As previously mentioned, wire bond cap 350 would normally be made of Kovar or Alloy 42 and be first nickel plated and then over plated with a final finish an ultra-pure or soft gold suitable for wire bonding.

Figure 23:
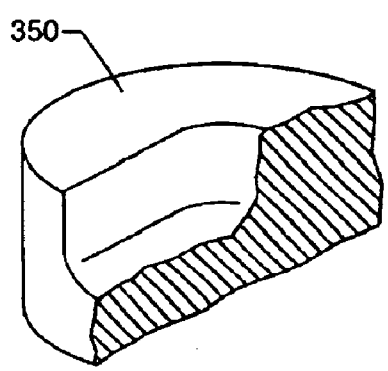
FIG. 23 is a cutaway isometric view of the wire bond cap of FIGS. 21 and 22.

FIG. 23 is a cut away isometric view of the wire bond cap 350 of FIGS. 21 and 22.

Figure 24:
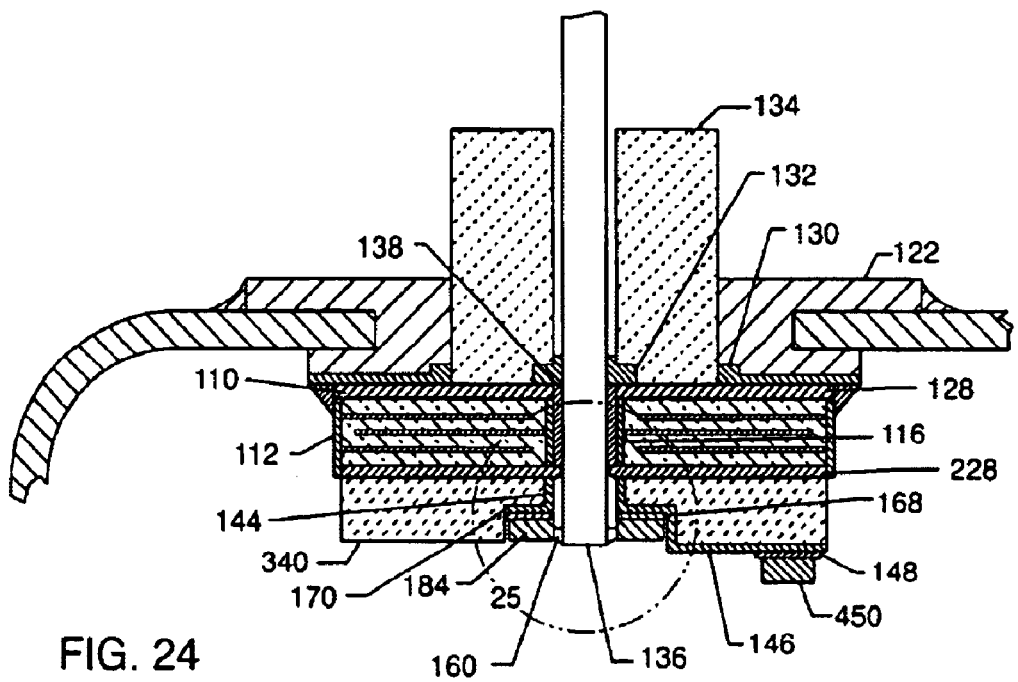
FIG. 24 is a fragmented cross-sectional view of the EMI filter hermetic terminal of FIG. 5 with modifications.
Figure 25:
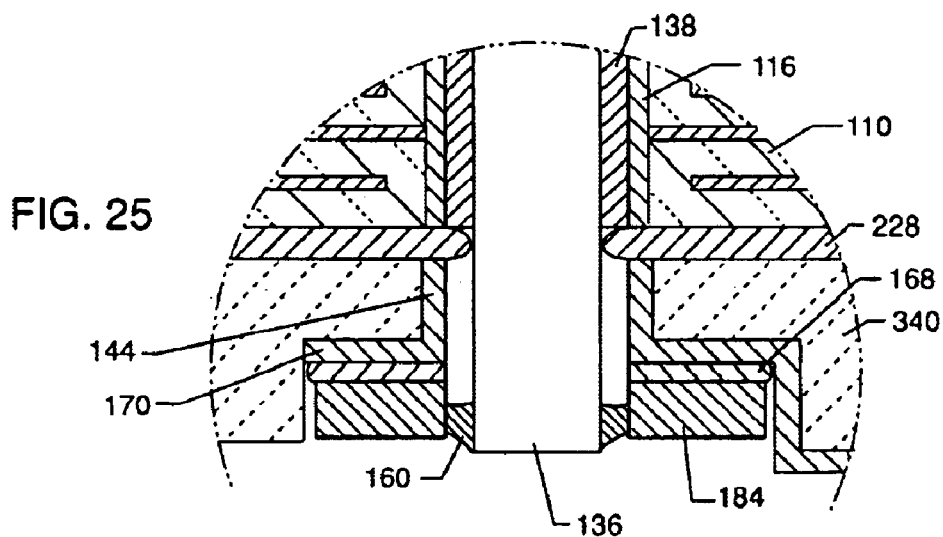
FIG. 25 is an enlarged, fragmented cross-sectional view of the area indicated by the number 25 in FIG. 24.

FIG. 24 is a cross-sectional view of the EMI filtered hermetic terminal of FIG. 5 modified with two improvements. As previously mentioned, it is highly desirable that all electrical connections that are in series with the input or output of an implantable medical device be of extremely high reliability. Accordingly, referring to FIG. 24, one can observe that there is a Kovar, Alloy 42 or equivalent metal insert ring 184 that is placed either on top of or into a counterbore of the alumina substrate 340. This is better understood by looking at the enlarged cross-section view of this same area of FIG. 24 in FIG. 25. According to FIG. 25, one can see the cross-section of the insert metal piece 184 which has been selectively plated with nickel and then pure gold. Ring 184 has been previously gold brazed to the metallization 170 of the alumina ceramic substrate 340 making a solid mechanical and electrical connection. The lead wire 136 is then attached by laser welding 160 to the metallic ring 184. Laser welding makes a very reliable and rugged electrical and mechanical joint in this important series connection.

Referring now back to FIG. 24, one can see that the metallization 144 on the inside diameter or via hole on the alumina substrate 340 is continuous as a circuit trace to 170 to 146 all the way to the wire bond pad area 148. The wire bond pad 450 is a metal block preferably of Alloy 42 or Kovar and is also undercoated with nickel and then overcoated with ultra-pure or soft gold suitable for wire bonding. It is well known in the art that laser welding or wire bonding is much more easily accomplished to a Kovar or Alloy 42 surface.

Figure 26:
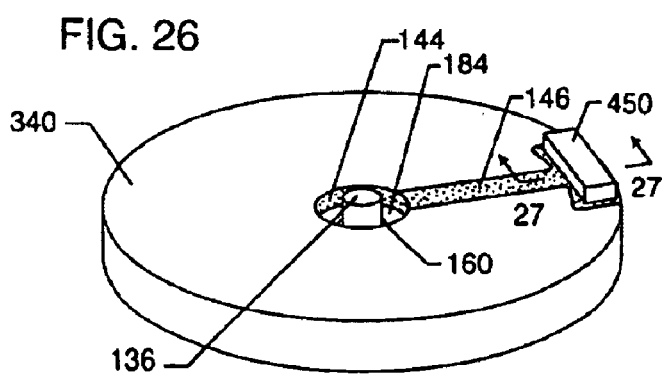
FIG. 26 is an inverted perspective view of the alumina substrate of FIG. 24.

FIG. 26 shows an inverted isometric view of the alumina substrate 340 of FIG. 24. In this view, one can easily observe the top of the insert ring 184, the tip of the lead wire 136, the circuit trace 146 and the Kovar or Alloy 42 wire bond pad 450.

Figure 27:
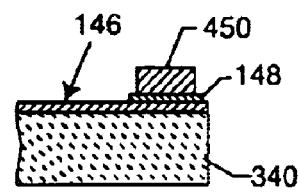
FIG. 27 is an enlarged, fragmented cross-sectional view taken along the line 27—27 of FIG. 26.

FIG. 27 is a cross-sectional view from FIG. 26 which better illustrates the mounting of the wire bond pad 450. As one can see, wire bond pad 450 has been electrically and mechanically attached to the circuit trace 146 using braze preform 148. This brazing operation would typically be performed on the alumina substrate 340 in a high temperature vacuum-brazing furnace. The braze joints 168 and 148 of FIG. 24, which attaches the ring 184 to the alumina substrate metallization 170 and the wire bond pad 450 to the alumina substrate 340 metallization 146 would typically be done prior to capacitor bonding at the same time in vacuum brazing furnace re-flow operation.

Referring again back to FIG. 24, one can see that the electrical connection material that electrically connects the inside diameter metallization 116 of the feedthrough capacitor 110 to the lead wire 136 also directly contacts the hermetic terminal gold braze material 132. Accordingly, it is an important feature of the novel EMI filtered terminal with wire bond substrate as shown in FIG. 24 that the lead wire 136 can be of both solderable or heavily oxidized materials. Specifically, lead wire 136, as shown in FIG. 24, can be of the group of niobium, tantalum, titanium or other heavily oxidized materials. Normally, such heavily oxidized materials are not readily wettable with solder or suitable for attachment using a thermal setting conductive adhesive. However, as described in pending U.S. patent application Ser. No. 10/377,086, it is not necessary to make direct contact to the lead wire if contact is made to the gold braze material of the hermetic terminal 132. It is important to note that the manufacturing step of brazing gold material 132 to the lead wire 136 burns through any such surface oxides or contamination and makes a very highly reliable hermetic and electrical connection to the lead wire 136. In turn, direct contact of the thermal setting conductive adhesive or solder material 138 makes a highly reliable, low impedance, electrical connection for the proper operation of the feedthrough capacitor EMI filter 110.

Referring once again to FIG. 24, a similar electrical connection from the insert ring 184 to the lead wire 136 is formed by the laser welding material 160. This laser weld also burns through any surface oxide on niobium, tantalum, or titanium pins and the like, thereby making a highly reliable electrical connection from the pin 136 to the ring 184 which has been previously gold brazed to the surface metallization 170, of substrate 340.

In summary, the novel feedthrough capacitor with substrate as described in FIG. 24 has a number of advantages, including the obvious one of having highly reliable brazed electrical connections, and being suitable for wire bonding, but also suitable for use with literally any type of biocompatible lead wire 136.

Figure 28:
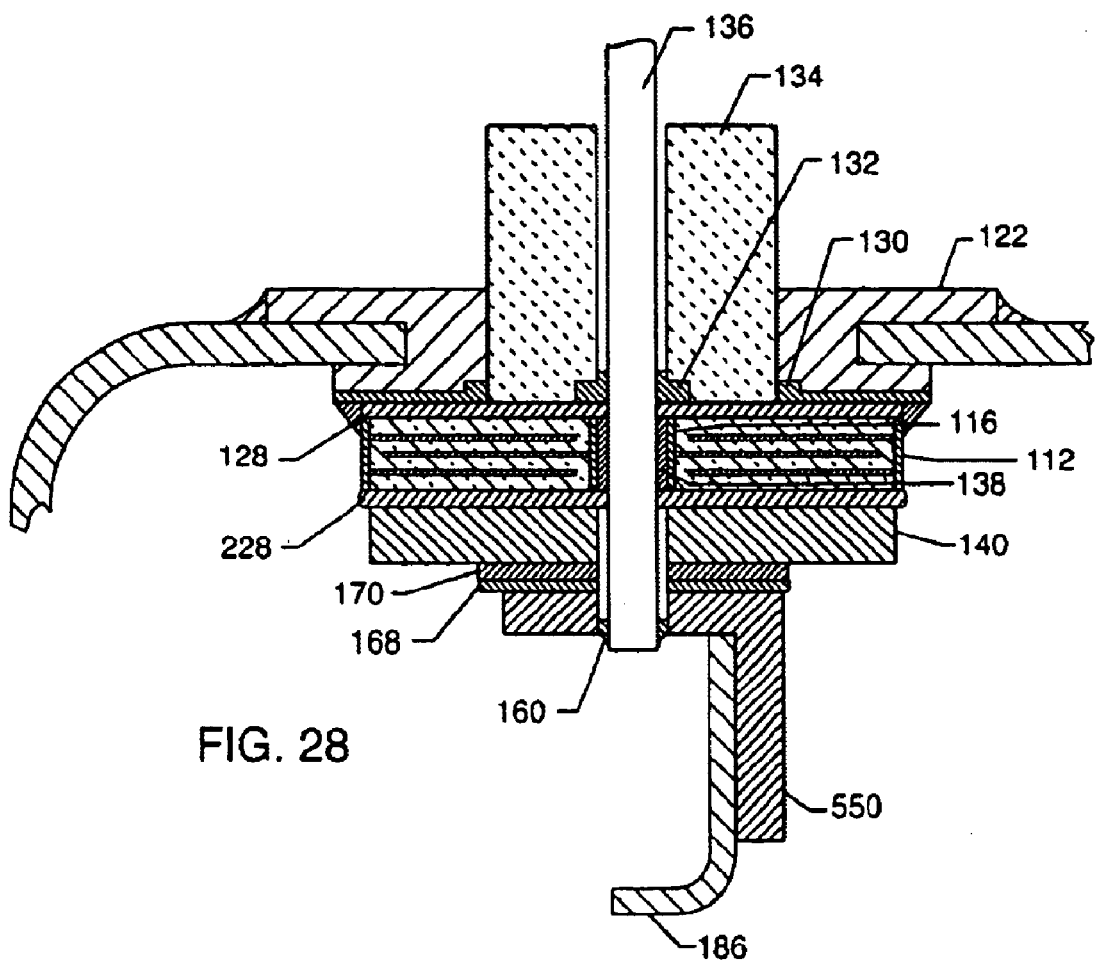
FIG. 28 is a fragmented cross-sectional view similar to FIG. 5, illustrating the use of an L-shaped wire bond cap.
Figure 29:
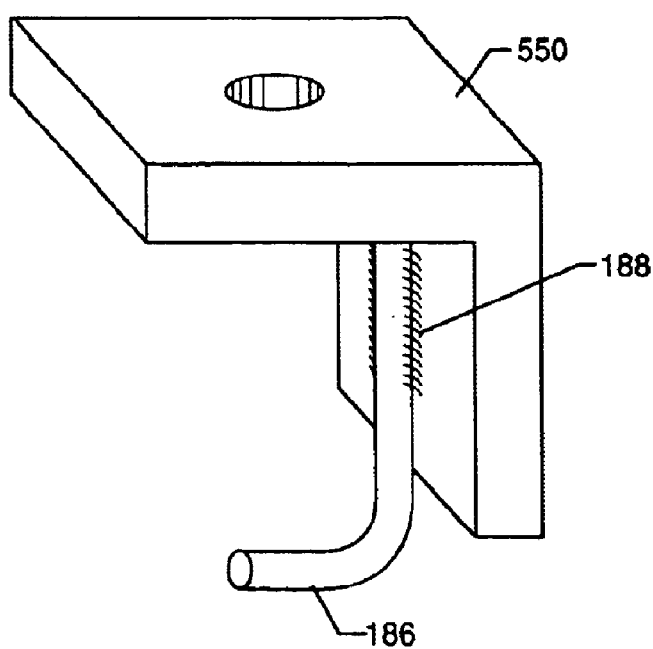
FIG. 29 is a perspective view of the attachment of a lead wire to the L-shaped wire bond pad of FIG. 28.

FIG. 28 illustrates a cross-sectional view of the present invention with an L-shaped wire bond cap 550. This wire bond cap 550 is typically Kovar or Alloy 42 and is gold plated. Also shown in FIG. 28 is the cross-section of a wire bonded lead wire 186. The attachment of lead wire 186 to the L-shaped wire bond pad 550 is better seen in isometric view FIG. 29. As one can see, lead wire 186, which is routed to internal implanted medical device circuitry, has been wire bonded in the area shown as 188 to the wire bond pad 550. It is typical in the art that 186 be a small diameter, pure gold or aluminum wire, such as a wire 0.005 inches in diameter. The wire bond connection 188 is typically formed by ultrasonic or thermosonic processes that are very well known in the art.

Figure 30:
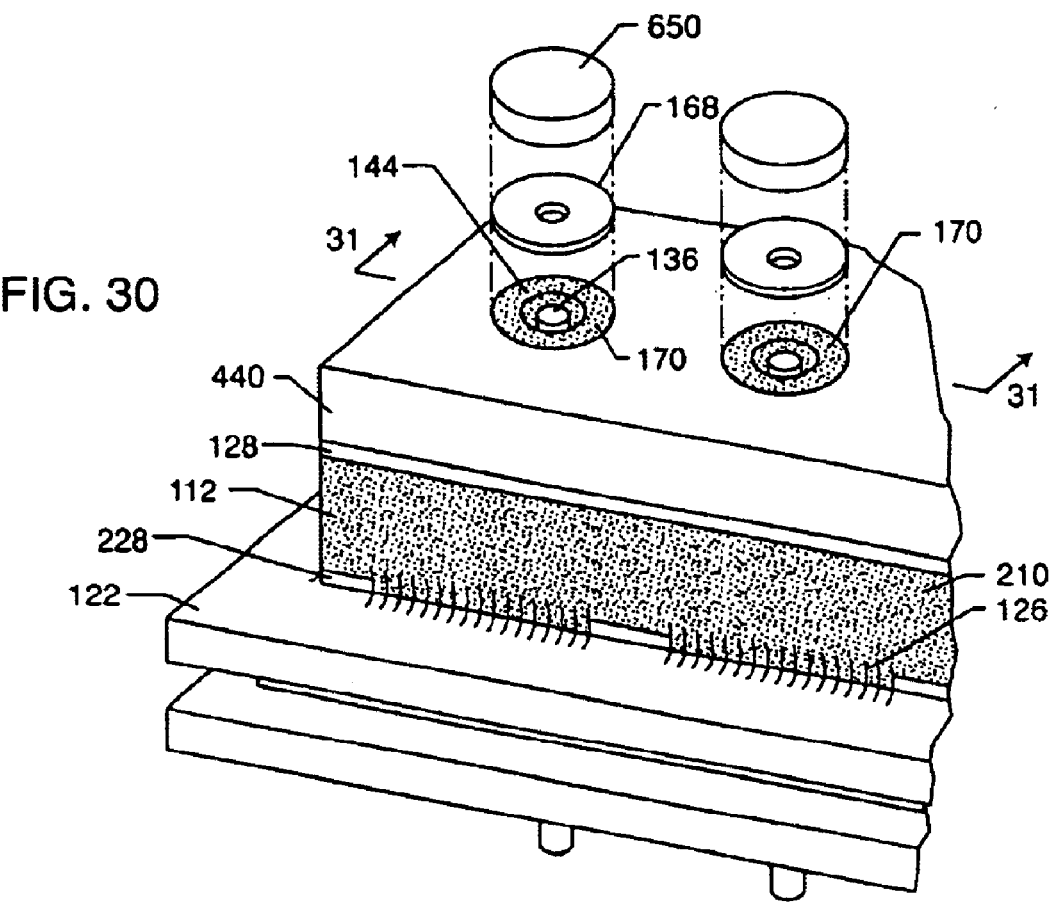
FIG. 30 is a fragmented perspective and partially exploded view of a bipolar feedthrough terminal assembly with wire bond caps.
Figure 31:
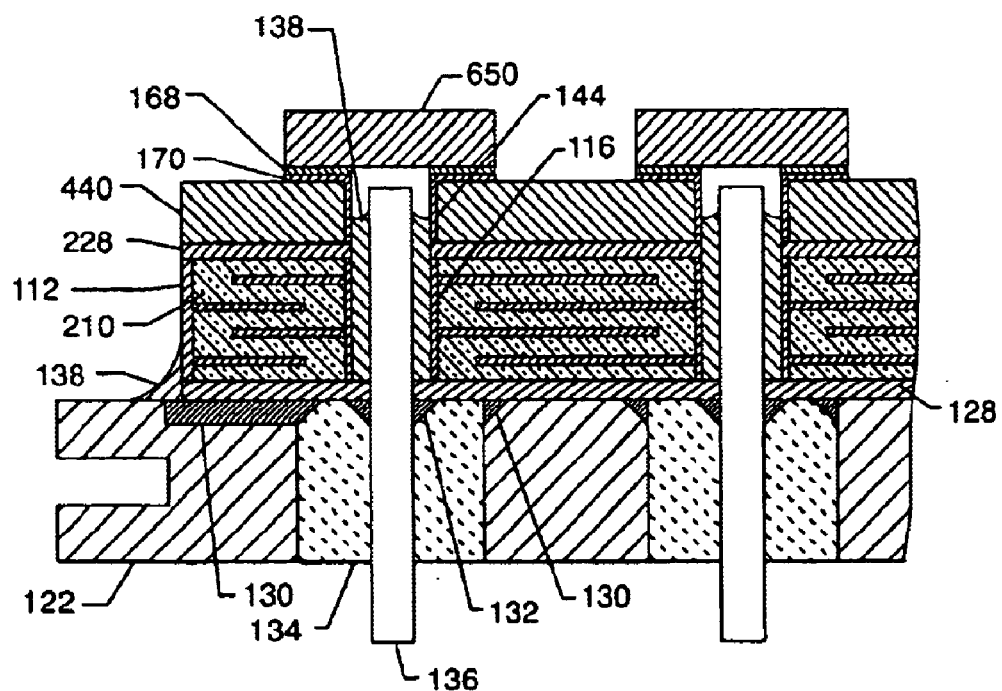
FIG. 31 is an enlarged, fragmented cross-sectional view taken generally along the line 31—31 of FIG. 30.

FIG. 30 illustrates the top view of a bipolar capacitor of the present invention. In this embodiment, exploded away circular wire bond pads 650 are placed over the top of the feedthrough holes of substrate 440 for convenient attachment of lead wires 186 (not shown). This is better understood by observing the cross-section of FIG. 30 illustrated in FIG. 31. As shown in FIG. 31, a circular wire bond pad 650 is attached to the top surface via metallization 170 of the ceramic substrate 440. The attachment of the circular wire bond pad 650 is by gold brazing 168 to the top metallization 170 of the alumina substrate 440. In this case, the lead wire 136, which comes from the hermetic terminal consisting of 122, 130, 132, 136 and 134, is shortened as shown. The alumina substrate 440 is co-bonded using a nonconductive polyimide preform 228 to the top surface of the ceramic capacitor 210. The electrical connection material 138 is typically a conductive thermal setting polymer, such as a conductive polyimide, solder or the like. The electrical connection material 138 electrically connects the inside diameter or via hole metallization 144 of the substrate 440 to the lead wire 136 and in turn to the inside diameter metallization 116 of the feedthrough capacitor 210.

Figure 32:
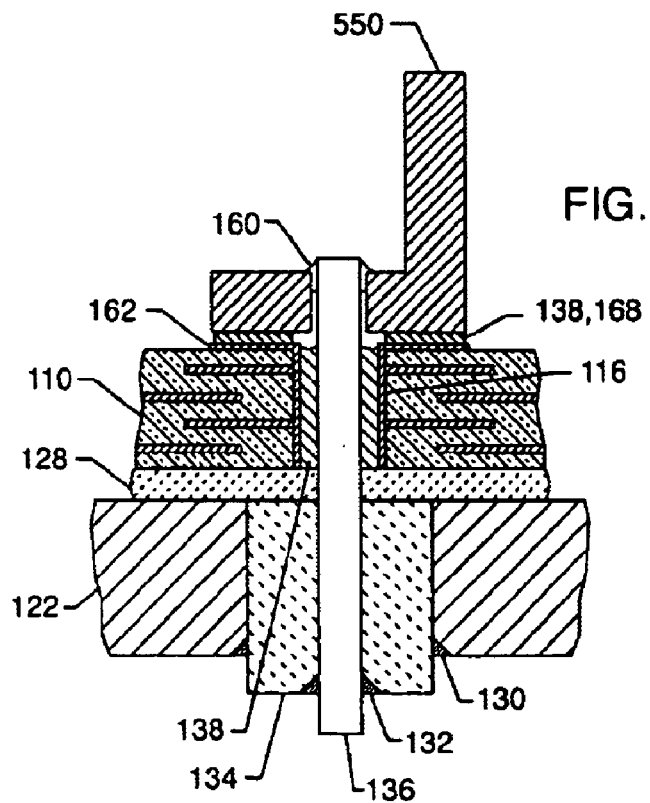
FIG. 32 is a sectional view of an alternative wire bond pad arrangement in comparison with that illustrated in FIG. 28.

FIG. 32 shows an alternative embodiment to that previously described in FIG. 28. In both cases, there is an L-shaped wire bond pad 550. The difference in FIG. 32 is that the wire bond pad 550 has been directly attached to the top of the ceramic feedthrough capacitor 110. In this case, there is not an alumina or other substrate that is intermediary between the wire bond pad 550 and the top surface of the ceramic capacitor 110. In this case, the wire bond pad 550 is electrically and mechanically attached to the top of the ceramic capacitor using a conductive thermal setting polymer 138, a gold braze or a solder 168. A laser weld connection 160 is formed between lead wire 136 and the wire bond pad 550 as shown. FIG. 32 is a lower cost alternative, but is not considered to be as mechanically robust as having an alumina or equivalent material substrate 140 placed between the wire bond pad 550 and the ceramic capacitor 110. In FIG. 32, the ultrasonic wire bonding forces that would be applied during the attachment of the lead wire 186 (not shown) would put substantial mechanical stress onto the relatively fragile ceramic capacitor 110 itself. This must be a highly controlled process so that microfractures are not induced into the ceramic capacitor 110. Such microfractures have been shown to cause immediate or latent failure (electrical short circuit) of capacitor 110. Such short circuiting could be life threatening to a pacemaker patient.

Figure 33:
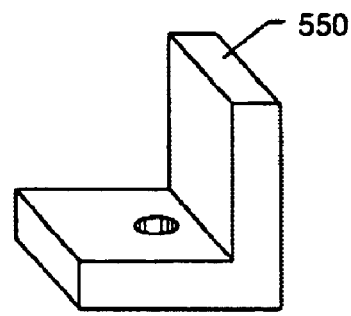
FIG. 33 is a perspective view of the L-shaped wire bond pad of FIGS. 32 and 28.
Figure 34:
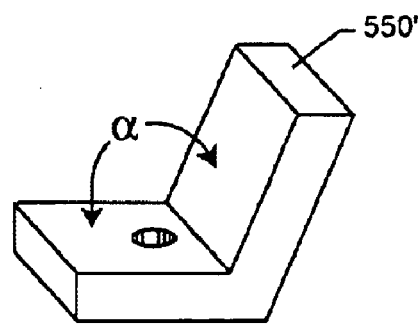
FIG. 34 is a perspective view similar to FIG. 33, illustrating the configuration of an alternative wire bond pad.

FIG. 33 is an isometric view of the L-shaped wire bond pad 550, previously described in FIG. 32. FIG. 34 is a similar wire bond pad 550' as described in FIG. 33, except that it is angled ($\propto$) to line up with the geometry or architecture of the internal circuits of the implanted medical device. As shown in FIG. 34, any convenient angle ($\propto$) can be used.

Figure 35:
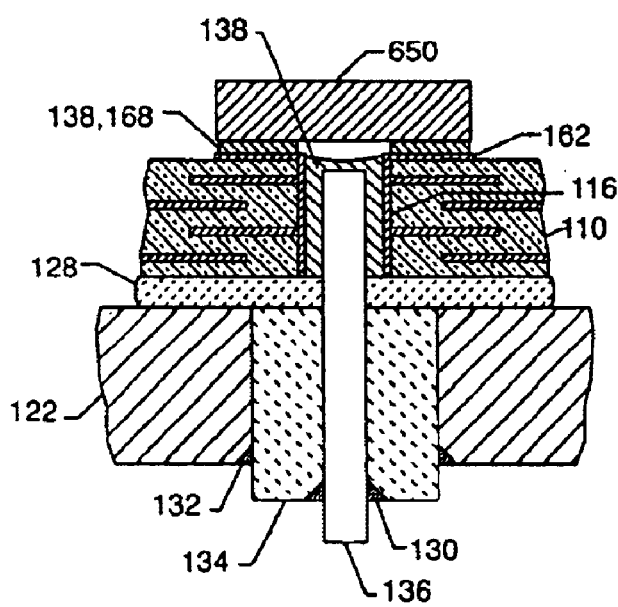
FIG. 35 is a sectional view similar to FIG. 32, illustrating the use of a circular or rectilinear wire bond pad.

FIG. 35 is similar to FIG. 32 with a circular or rectilinear wire bond pad 650 or 650'. In FIG. 35, direct attachment is made from the wire bond pad 650 to the top surface metallization 162 of ceramic capacitor 110. As described in FIG. 32, there is no alumina or other substrate 140 that is intermediary between the wire bond pad 650 and the ceramic capacitor 110. Attachment of the circular wire bond pad 650 can typically be done by thermal setting conductive adhesive 138 or brazing or solder 168. Generally, a gold braze would not be used since braze materials tend to be too brittle and could induce microfractures into the ceramic capacitor.

Figure 36:
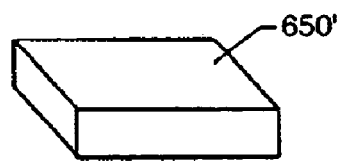
FIG. 36 is a perspective view of a rectilinear wire bond pad that could be incorporated into the assembly of FIG. 35.
Figure 37:
FIG. 37 is a perspective view of a circular wire bond pad that can be utilized in FIG. 35.

FIG. 36 is an isometric view of a square wire bond pad 650' of FIG. 35 and FIG. 37 is an isometric view of a circular wire bond pad 650 that would also be suitable for the cross-sectional assembly as shown in FIG. 35.

Figure 38:
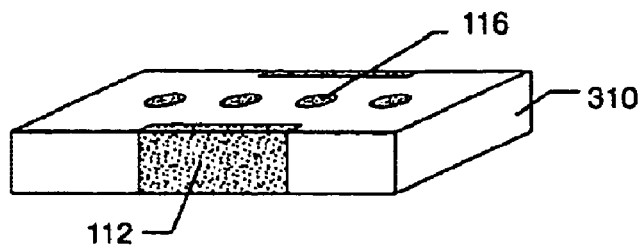
FIG. 38 is a perspective view of a prior art in-line quadpolar feedthrough capacitor.
Figure 39:
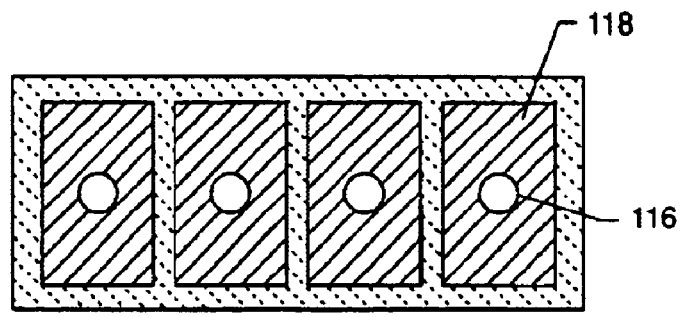
FIG. 39 illustrates the active electrode plate configuration of the capacitor shown in FIG. 38.
Figure 40:
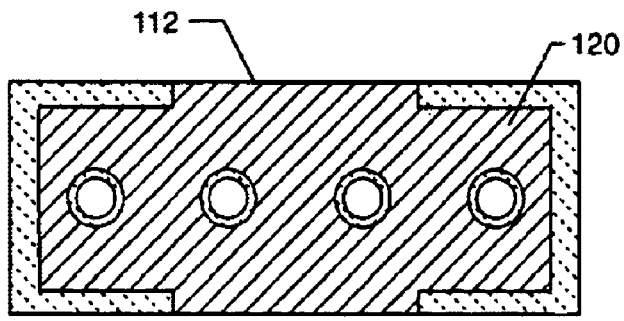
FIG. 40 illustrates the ground electrode configuration of the capacitor illustrated in FIG. 38.

FIG. 38 illustrates a prior art in-line quadpolar feedthrough capacitor 310. The inside diameter of the feedthrough holes are metallized shown as 116. There are two ground electrode connections 112 as shown. FIG. 39 illustrates the active electrodes 118 of the capacitor of FIG. 38. FIG. 40 illustrates the ground electrodes 120 of the capacitor shown in FIG. 38.

Figure 41:
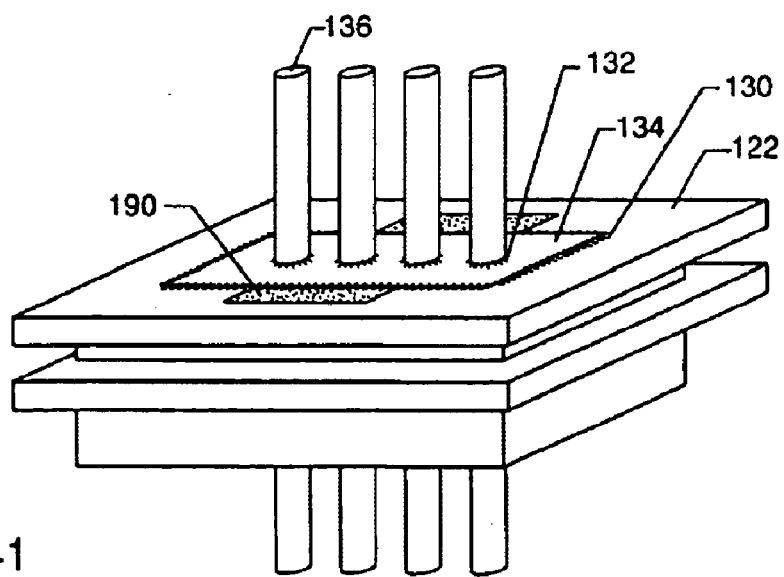
FIG. 41 is a perspective view of a prior art quadpolar hermetic feedthrough terminal assembly.

FIG. 41 illustrates a quadpolar hermetic feedthrough terminal assembly as described in pending U.S. patent application Ser. No. 10/377,086. The four lead wires 136 are in nonconductive relationship by way of alumina ceramic insulator 134. Hermetic seals 132 are made around the outside diameter of each lead wire 136 and the inside perimeter 130 of the metallic ferrule 122 typically by gold brazing, glass sealing or the like. There are two gold pad areas 190 described in pending U.S. patent application Ser. No. 10/377,086 for convenient electrical attachment of the feedthrough capacitor ground metallization 112 of FIG. 38. As described in pending U.S. patent application Ser. No. 10/377,086, it is important to make contact directly to gold and not to the titanium ferrule 122. This is because titanium oxides can preclude the proper operation of the feedthrough capacitor of FIG. 38 at high frequency.

Figure 42:
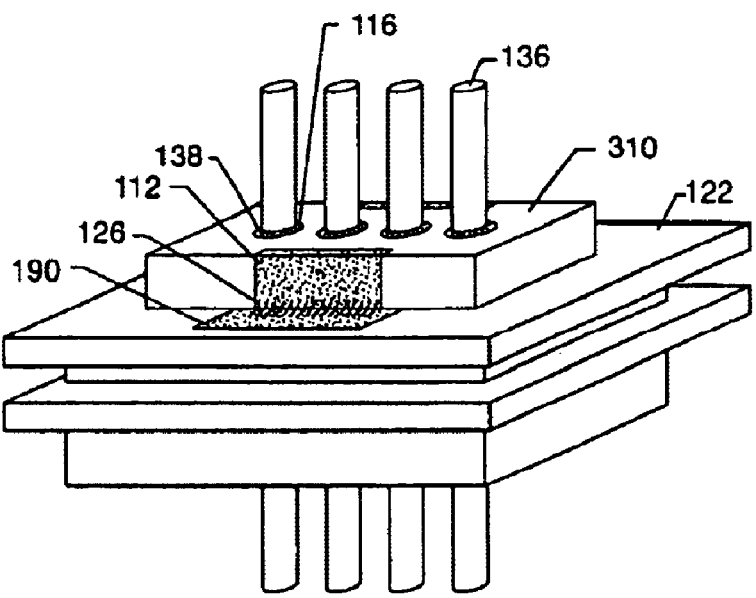
FIG. 42 is a perspective view illustrating the assembly of the capacitor of FIG. 38 to the terminal assembly of FIG. 41.

FIG. 42 illustrates the inline quadpolar feedthrough capacitor of FIG. 38 shown mounted to the hermetic terminal assembly of FIG. 41. Attachment is made between the capacitor ground metallization 112 and the gold braze areas 190 using a suitable electrical connection material 126 which can be of a number of materials, including thermal setting conductive adhesives, solders and the like. There is also an electrical connection material 138 that connects the lead wires 136 to the inside diameter metallization 116 of the feedthrough capacitor 310.

Figure 43:
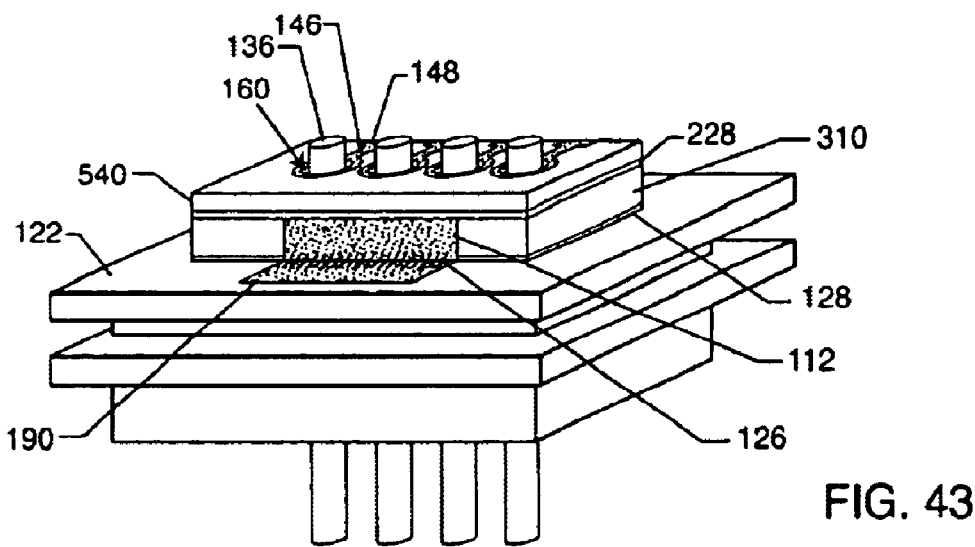
FIG. 43 is a perspective view similar to that illustrated in FIG. 42, illustrating modifications in accordance with the present invention, namely use of a quadpolar alumina substrate co-bonded to the top of the ceramic capacitor.

FIG. 43 is the feedthrough filtered capacitor assembly of FIG. 42 modified in accordance with the present invention. In this case, a quadpolar alumina substrate 540 has been co-bonded to the top of the ceramic capacitor 310 using insulating adhesive material 228. Highly reliable laser weld connections 160 are used to connect the inside diameter or via metallization 144 (not shown) of the alumina ceramic substrate 540 to the four lead wires 136. As one can see, there are circuit traces 146 as part of the alumina substrate that connect to wire bond pad areas 148. As previously mentioned, such circuit traces 146 and wire bond pad areas 148 with selectively metallized via holes are very typical in the art and are in very common use with a number of substrate materials, including aluminum oxide, alumina, fiberglass, polyimide and many others.

Figure 44:
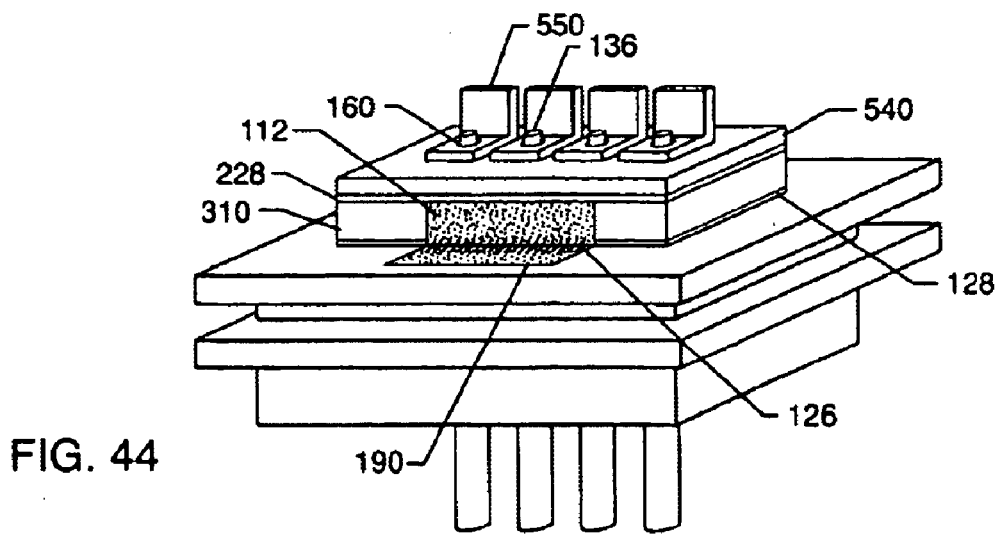
FIG. 44 is a perspective view similar to FIG. 43, illustrating the use of L-shaped wire bond pads.

FIG. 44 illustrates an alternative embodiment of FIG. 43 showing L-shaped wire bond pads 550. As previously described in other FIGURES, these wire bond pads are gold brazed to metallization 170 (not shown) on the top of the alumina ceramic substrate 540. A laser weld connection 160 is then made from the lead wires 136 to each of the L-shaped wire bond pads 550. It would be obvious to one skilled in the art that a variety of shapes of wire bond pads would be available. In general, the L-shaped wire bond pad 550 arrangement illustrated in FIG. 44 is highly preferable to that previously described in FIG. 32. This is because alumina substrate 540 is placed intermediary between the wire bond pads 550 and the ceramic capacitor 310. Therefore, when wires 186 (not shown) from implantable device circuits are attached to the L-shaped pads 550 by thermal, thermosonic or ultrasonic bonding, the substantial forces generated can be distributed throughout the alumina substrate 540. Alumina ceramic and other common substrate materials are typically much stronger than the ceramic feedthrough capacitor itself. It is a general rule in ceramic engineering that the higher the dielectric constant the weaker the material is. For example, in a 2500K barium titanate feedthrough capacitor, the material is relatively weak compared to that of alumina ceramic which has a K of below 10. The alumina substrate 540 as illustrated in FIG. 43 and FIG. 44, is co-bonded to the top of the ceramic feedthrough capacitor 310 using a suitable insulator washer 228, which in the preferred embodiment, would be an adhesive coated polyimide as described in FIG. 6 which would be cured at high temperature. Polyimide is an ideal polymer in this case because it forms a ring molecule which tends to absorb stresses. An epoxy or similar material could work, however, it would tend to transmit more stress to the surface of the ceramic capacitor.

The sandwiched type of construction as illustrated in FIGS. 43 and 44 minimizes the stresses to the ceramic capacitor 310. These ceramic materials, including barium titanate, tend to be stronger in compression than in tension or shear. By laminating the structure as shown in FIGS. 43 and 44, most of the shear and tension type loads are absorbed by the alumina ceramic substrate. The resulting compression loads that are distributed to the ceramic feedthrough capacitor are not of great concern because of the fact that ceramic materials are stronger in compression.

FIG. 45 illustrates a hermetic terminal with a grounded lead wire 236 as described in U.S. Pat. Nos. 5,905,627 and 6,529,103, the contents of which are incorporated herein. Lead wires 136 are held in insulative or nonconductive relation with the metallic ferrule 122 by way of the two alumina or glass insulators 134.

FIG. 46 shows a prior art internally grounded bipolar feedthrough capacitor 410. Internally grounded feedthrough capacitors are well known in the art and are described by U.S. Pat. Nos. 5,905,627 and 6,529,103. FIG. 47 illustrates the active electrode plates 118' of the internally grounded feedthrough capacitor of FIG. 46. FIG. 48 illustrates the ground electrode plates 120' of the internally grounded feedthrough capacitor of FIG. 46.

Figure 49:
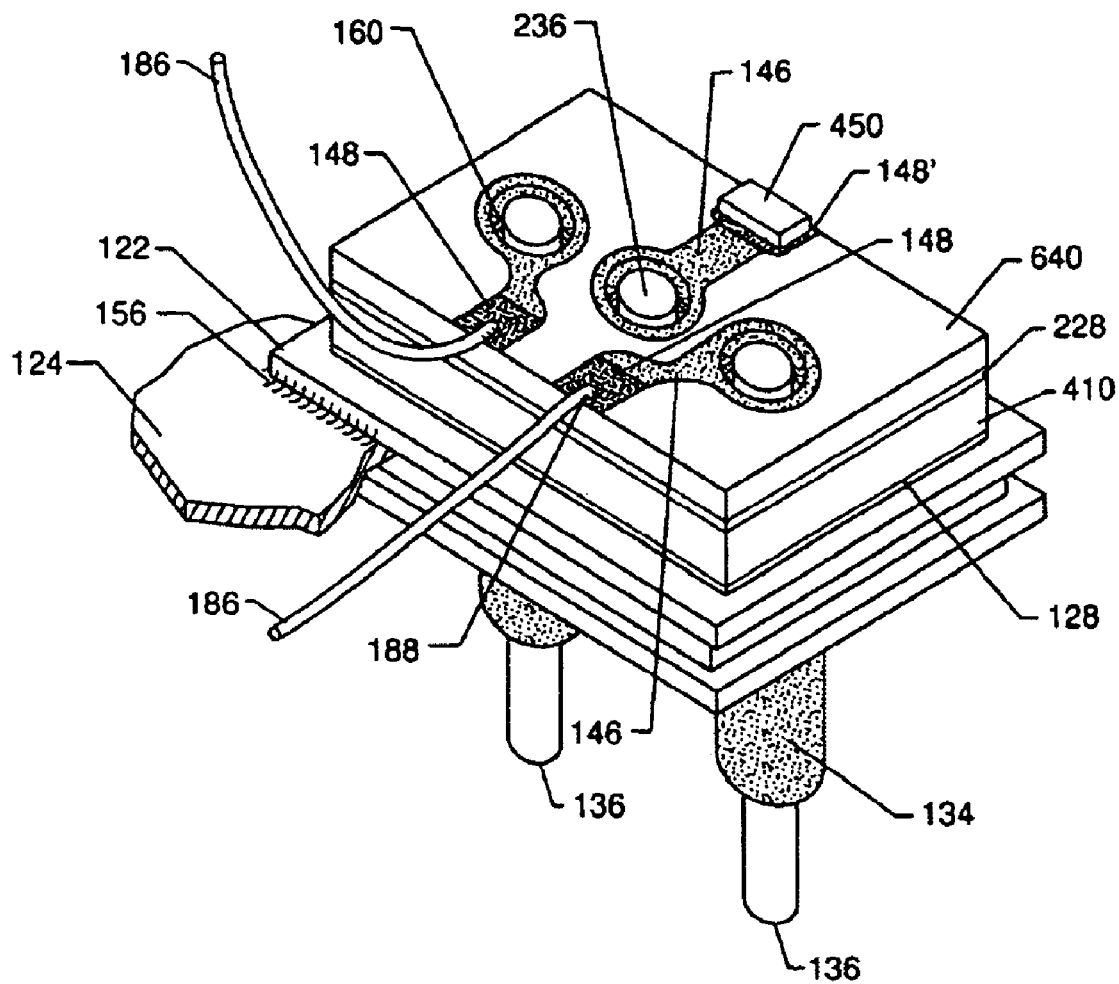
FIG. 49 is a perspective view of the capacitor of FIG. 46 mounted to the hermetic terminal assembly of FIG. 45 with a co-bonded wire bond substrate.

FIG. 49 illustrates the internally grounded bipolar feedthrough capacitor 410 of FIG. 46 mounted to the internally grounded hermetic terminal assembly as illustrated in FIG. 45. Ferrule 122 is typically of titanium and has been designed to be laser welded into the housing of an implantable medical device 124, such as a cardiac pacemaker, which is shown as a cut away of the housing of a cardiac pacemaker and having a laser weld 156 which makes a mechanical and hermetic connection to the hermetic terminal ferrule 122. FIG. 49 also illustrates the internally grounded bipolar feedthrough capacitor 410 of FIG. 46 employing the novel embodiments of the present invention. Alumina substrate 640 has been co-bonded using nonconductive insulating adhesive material 228 to the ceramic capacitor 410. Also illustrated in FIG. 49 are two alternative circuit traces 146 and wire bond pads 148 and 148'. Wire bond pad 450 is shown connected to the grounded lead bond pad 148' as suitable for a more reliable wire bond connection. A lead wire 186 is wire bonded 188 directly to the circuit trace wire bond pad area 148 of the alumina ceramic substrate 640. In the preferred embodiment, the inside diameter via hole metallization 144 (not shown) of the alumina substrate 640 would be connected to the lead wires 136 and 236 by laser weld material 160. Other suitable (but less reliable) connections could be made using solder, thermal setting conductive adhesives or the like. In general, a laser weld or braze makes for a much higher reliability in series electrical connection.

Figure 50:
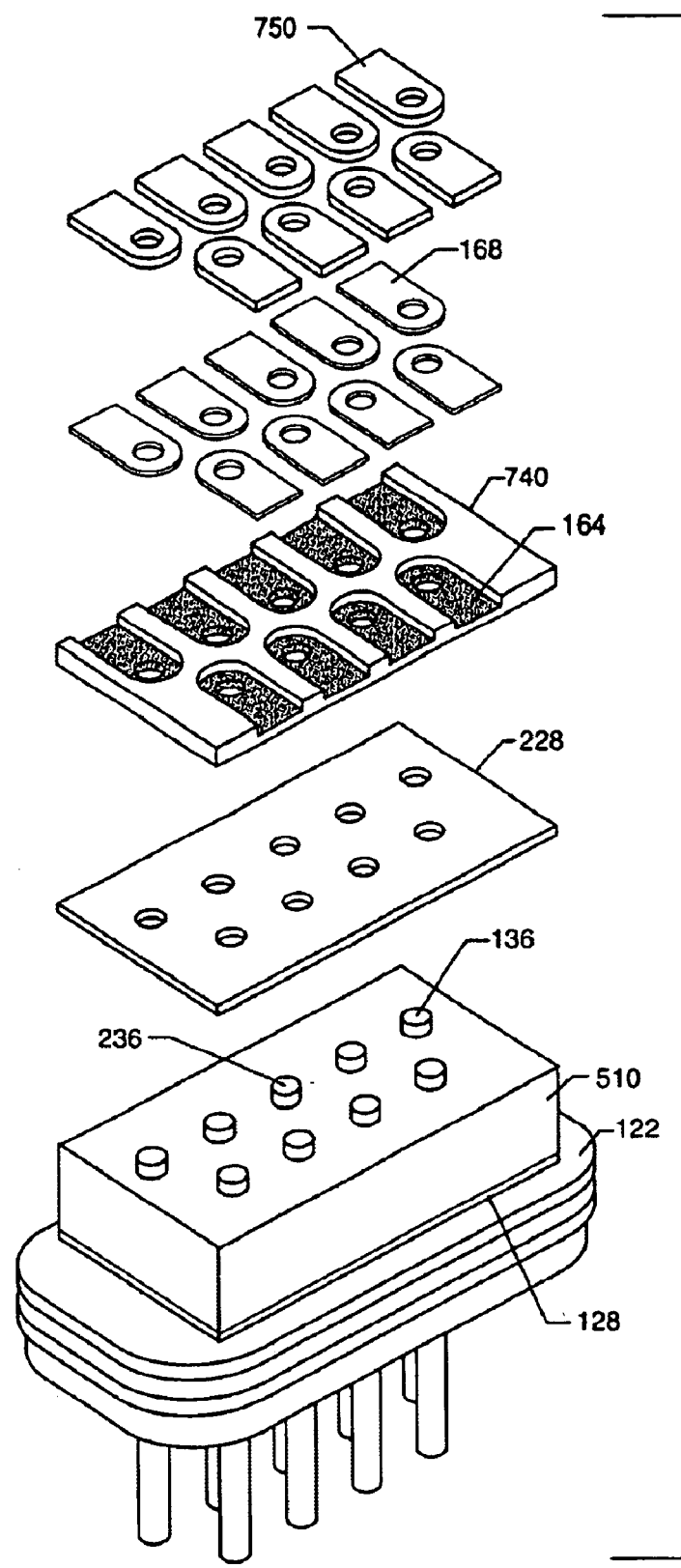
FIG. 50 is an exploded perspective view of an internally grounded dual inline 9-pole filter feedthrough capacitor hermetic terminal embodying the present invention.

FIG. 50 illustrates an exploded view of an internally grounded dual inline 9-pole filtered feedthrough capacitor 510 hermetic terminal of the present invention. In the exploded view, one can see the wire bond pads 750, which are typically of gold plated Kovar or the like. The alumina substrate 740 has convenient recesses and metallized areas 164 (typically of gold or nickel coated tungsten) suitable for metallurgical connection via gold brazing material or preforms 168 to the wire bond pads 750. An adhesive coated polyimide nonconductive preform 228 bonds the alumina substrate 740 to the ceramic feedthrough capacitor 510. As previously mentioned, internally grounded feedthrough capacitors are well known in the art. As described in U.S. Pat. No. 5,905,627, it is preferable that the ground pin 236 be centered to provide a low inductance path to the feedthrough capacitor active electrode plates (not shown). Accordingly, ground pin 236 has been centrally located and solidly welded, gold brazed or machined into the metallic ferrule 122. All of the other pins 136 are in nonconductive relationship with the ferrule 122 as previously described in the prior art.

Figure 51:
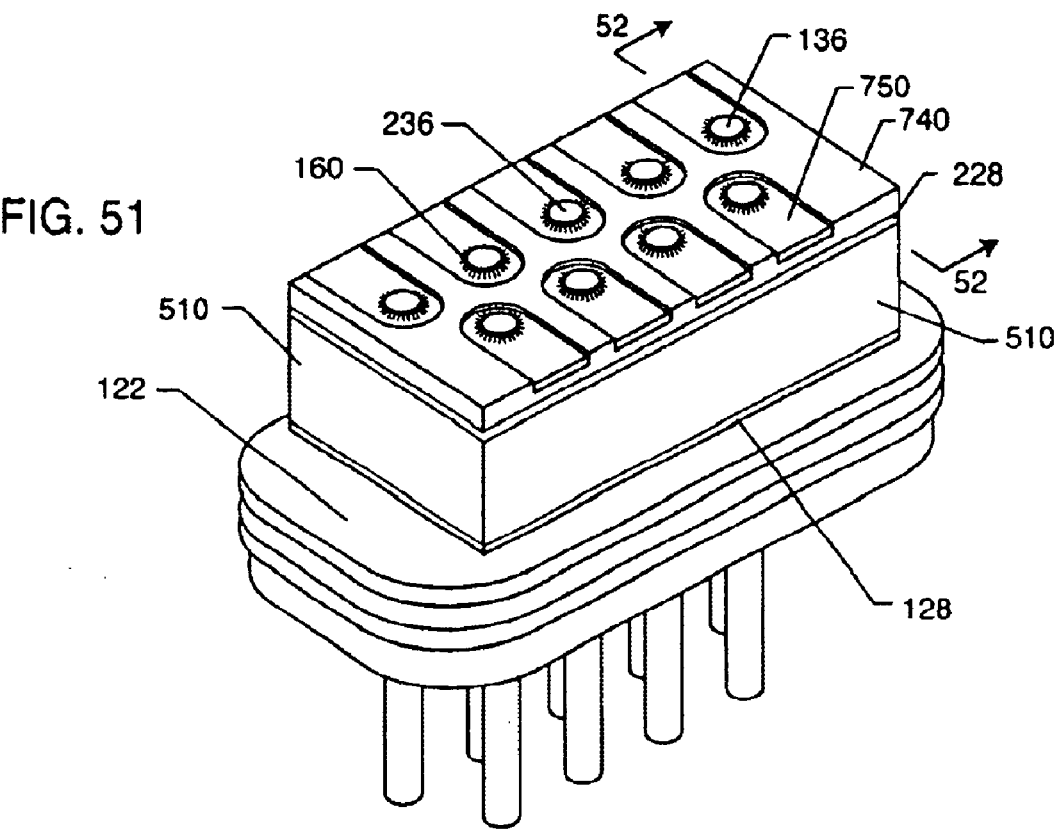
FIG. 51 is a perspective view of the assembled 9-pole filter feedthrough capacitor hermetic terminal of FIG. 50.

FIG. 51 illustrates a perspective view of the completed assembly of FIG. 50. As one can see, convenient wire bond attachment can be made to the wire bond pads 750. It should also be noted that there are a number of alternative shapes including L-shapes that could be used for these wire bond pads.

Figure 52:
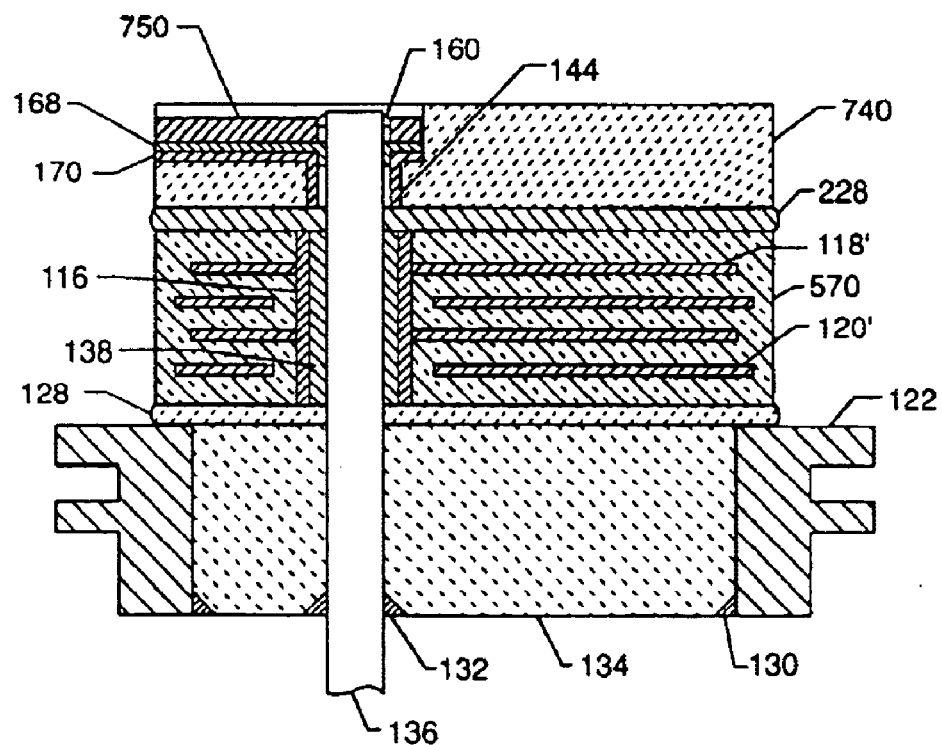
FIG. 52 is an enlarged cross-sectional view taken generally along the line 52—52 of FIG. 51.

FIG. 52 is a cross-sectional view of the 9-pole internally grounded feedthrough capacitor of FIG. 51. As one can see in the cross-sectional view, laser weld connection 160 is made between each wire bond pad 750 and the corresponding lead wire 136.

Figure 53:
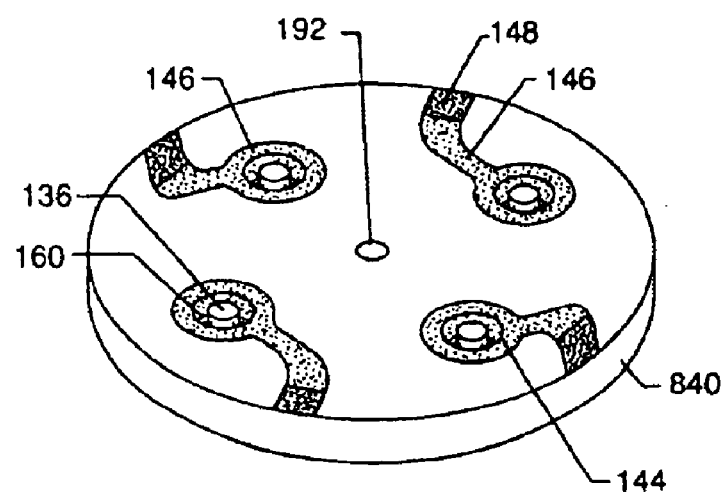
FIG. 53 is a perspective view of a quadpolar alumina substrate with circuit traces, wire bond pad areas and a leak detection vent hole in accordance with the present invention.

FIG. 53 illustrates a quadpolar alumina substrate 840 with circuit traces 146 and wire bond pad areas 148. Each of the four via holes has been metallized with material 144. In the art, via hole metallization can be done by plating, vacuum pull through processes, cladding, screen printing, silk screen, metal deposition or the like. In the preferred embodiment, such metallizations would be of tungsten/nickel, molybdenum, gold or the like. In FIG. 53, the center hole 192, is not metallized as it is provided for helium leak detection purposes only.

Figure 54:
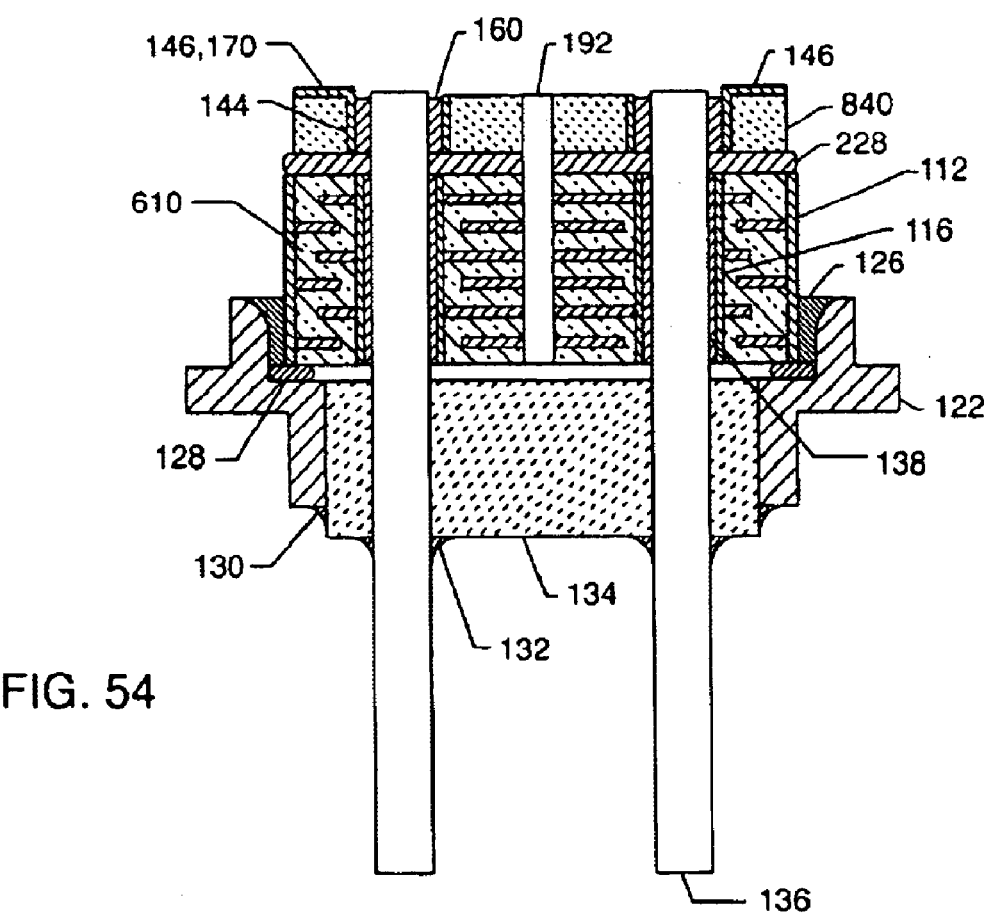
FIG. 54 is a cross-sectional view of a quadpolar feedthrough capacitor mounted to a ferrule with a capture flange, and incorporating the alumina substrate of FIG. 53.

FIG. 54 is a cross-sectional view of a quadpolar feedthrough capacitor 610 mounted to a ferrule with a capture flange 122. This ferrule is part of a quadpolar hermetic terminal assembly consisting of alumina ceramic insulator 134, lead wires 136 and gold braze connections 130 and 132. As noted, the ferrule 122 of the hermetic terminal in FIG. 54 has a capture flange, as described in U.S. Pat. No. 6,275,369. The quadpolar feedthrough capacitor 610, illustrated in FIG. 54, incorporates a centered helium leak detection vent hole 192, as described in U.S. Pat. No. 6,566,978. FIG. 54 also incorporates the novel alumina ceramic substrate 840 as previously described in FIG. 53. The substrate 840 is co-bonded 228 to the top of feedthrough capacitor 610 as shown. The leak detection vent 192 shown in the center of substrate 840 in FIG. 53, is centered over the corresponding leak detection vent in the feedthrough capacitor 610. One skilled in the art will realize that any of the ceramic substrates as described herein can be incorporated along with a leak detection vent hole 192 which is aligned with a corresponding leak detection vent hole in a feedthrough capacitor.

Figure 55:
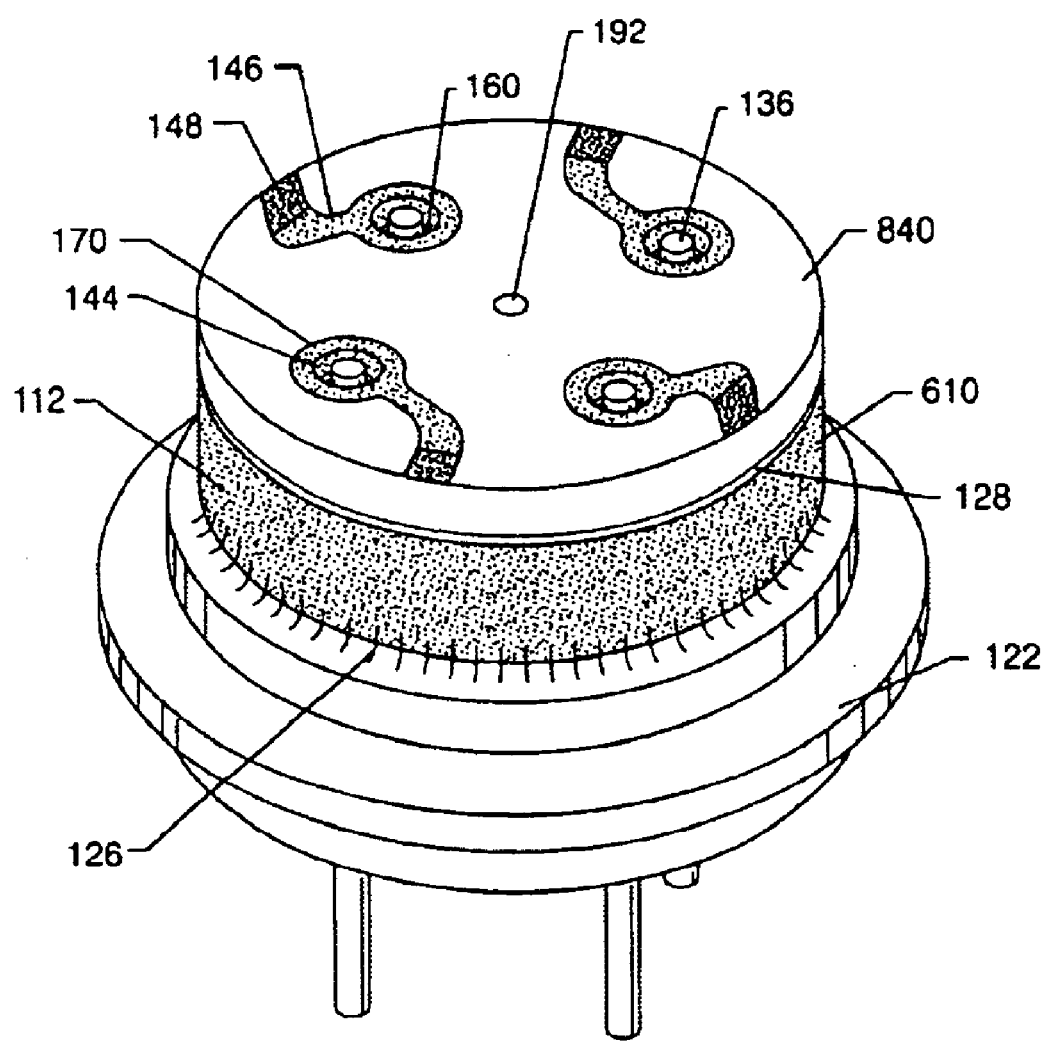
FIG. 55 is a perspective view of the quadpolar feedthrough capacitor of FIG. 54.

FIG. 55 illustrates an isometric view of the quadpolar feedthrough capacitor 610 with vent hole 192 of FIG. 53 and FIG. 54. The leak detection vent 192 is shown in the center. In a preferred embodiment, the electrical connection between the lead wires 136 and the inside diameter of the via holes 144 would be accomplished using a laser weld 160 or equivalent high reliability connection.

FIG. 56 illustrates a two-element or L-section filter which is the subject of U.S. patent application Ser. No. 60/508,426, the contents of which are incorporated herein. In this case, a ferrite inductor 194 has been co-bonded 328 to the top surface of the feedthrough capacitor 110 as shown. The schematic diagram of FIG. 56 is shown in FIG. 57. As described in U.S. patent application Ser. No. 60/508,426, series inductance improves the EMI filter performance. FIG. 56 also incorporates the features of pending U.S. patent application Ser. No. 10/377,086, wherein an electrical connection from both the capacitor inside diameter metallization 116 and outside diameter metallization 112 using connection material 138, 126 is made directly to gold braze material 132 and 130. This avoids any problem with oxides of titanium that are typical of titanium ferrule 122. An optional cosmetic over-coating of epoxy 196 has been added to provide a finished appearance to the FIG. 56 L-section filter.

FIG. 58 is the L-section filter of FIG. 56 modified in accordance with the present invention. As one can see, an alumina substrate 140 has been co-bonded 228 to the bottom surface of the ferrite bead 194. Co-bonding of the substrate 140 to the ferrite bead is typically done with the same adhesive backed polyimide insulating material as previously described in FIG. 6. An electrical connection 168 is made between the lead wire 136 and the inside diameter metallization 144 of the via hole of the substrate 140. This connection material 168 is typically solder, thermal setting conductive adhesive, brazes a laser weld (160) or the like.

Top metallization 170 of the alumina substrate 140 forms part of a continuous circuit trace 146 which is directed to a wire bond pad area 148. As previously described, this wire bond pad 148 can feature gold directly on the top surface of the alumina substrate 140 or incorporate a variety of Kovar of Alloy 42 wire bond pads 450 (not shown).

Figure 59:
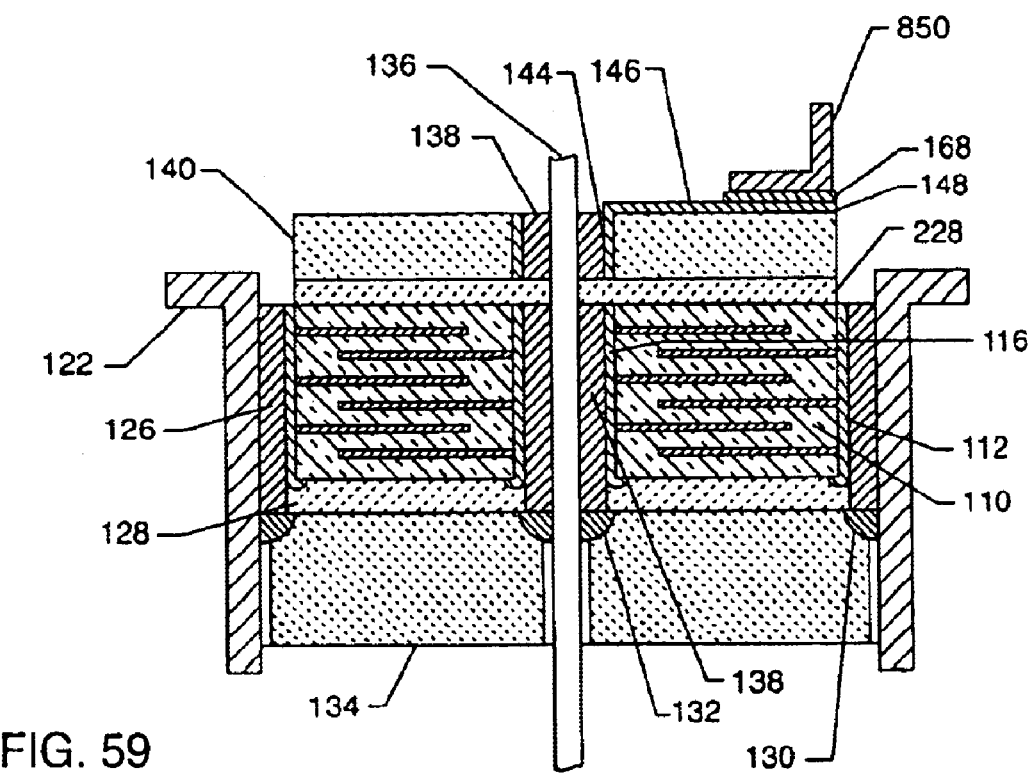
FIG. 59 is a cross-sectional view illustrating an embedded unipolar feedthrough filter capacitor including a substrate co-bonded directly to the top surface of the ceramic feedthrough capacitor in accordance with the present invention.
Figure 60:
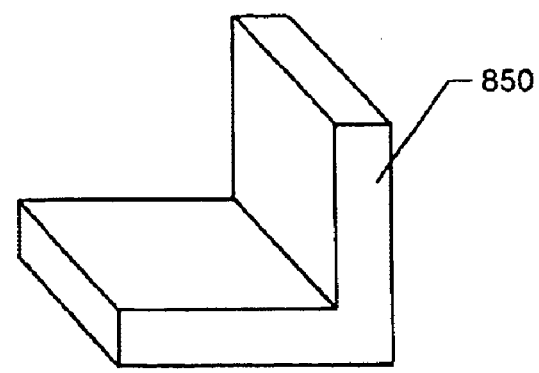
FIG. 60 is a perspective view of the L-shaped wire bond pad shown in FIG. 59.

FIG. 59 illustrates an embedded unipolar feedthrough capacitor in accordance with pending U.S. patent application Ser. No. 10/377,086. As shown, the substrate 140 has been co-bonded 228 directly to the top surface of the ceramic feedthrough capacitor 110. In this case, an L-shaped wire bond pad 850, as shown in FIG. 60, has been gold brazed 168 to the top surface metallization 148 of the alumina ceramic substrate 140. There is a continuous electrical connection through top metallization 146 to the inside diameter metallization of the via hole 144. Connection material 168 can be of gold braze, solder, thermal setting conductive adhesive and the like. The lead wire 136 is thereby electrically connected to the inside diameter metallization 144 of the alumina ceramic substrate 140.

Figure 61:
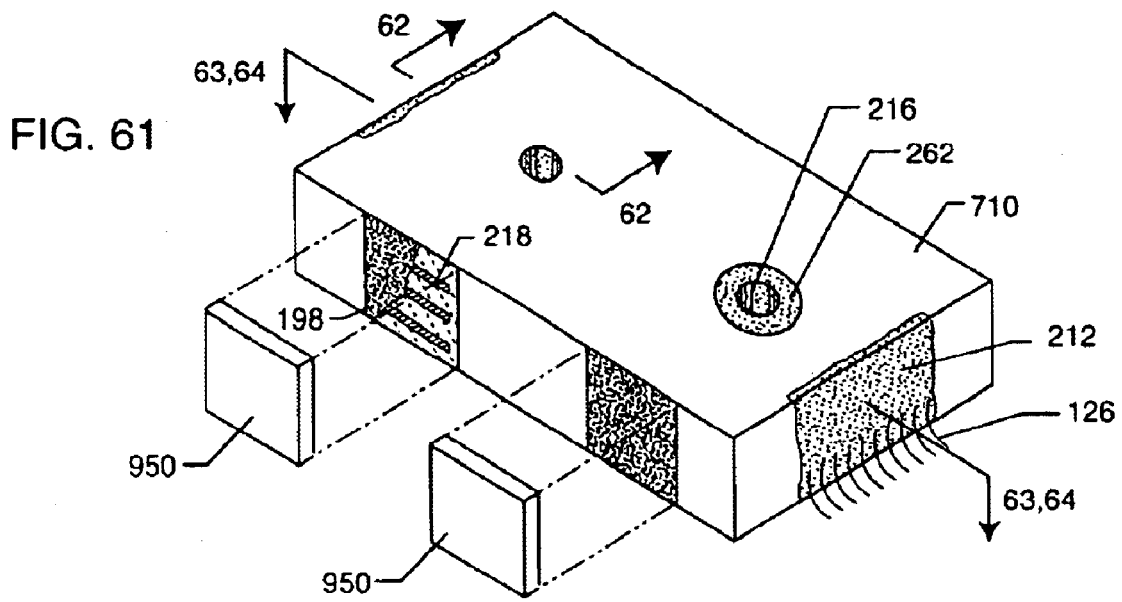
FIG. 61 is a perspective view of a bipolar feedthrough capacitor incorporating integrated wire bond pads in accordance with the present invention.

FIG. 61 is a bipolar feedthrough capacitor 710 incorporating integrated wire bond pads 198. The ground electrode metallization 212 is electrically connected by connection material 126 to a metallic ferrule (not shown).

Figure 62:
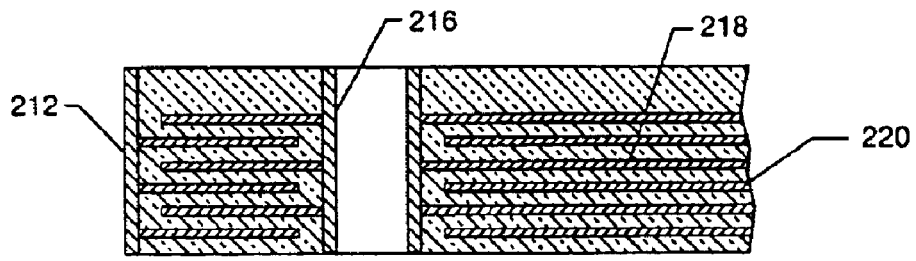
FIG. 62 is an enlarged cross-sectional view taken generally along the line 62—62 of FIG. 61.
Figure 63:
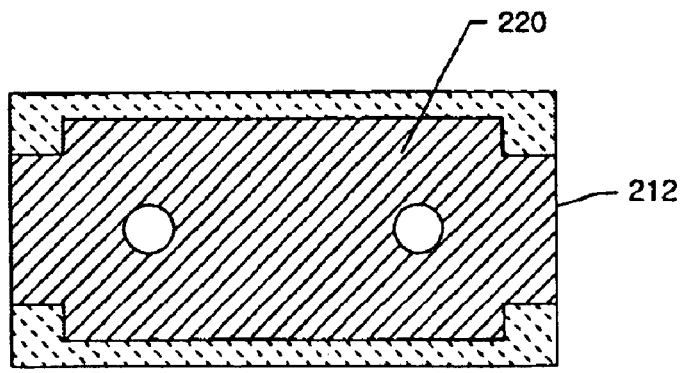
FIG. 63 is a sectional view taken generally along the line 63—63 of FIG. 61, illustrating the configuration of ground electrode plates within the capacitor.

FIG. 62 is a cross-sectional view of the bipolar capacitor 710 of FIG. 61. The ground electrode plates 220 of the bipolar feedthrough capacitor, as shown in FIG. 63, extend to the outer metallization 212.

Figure 64:
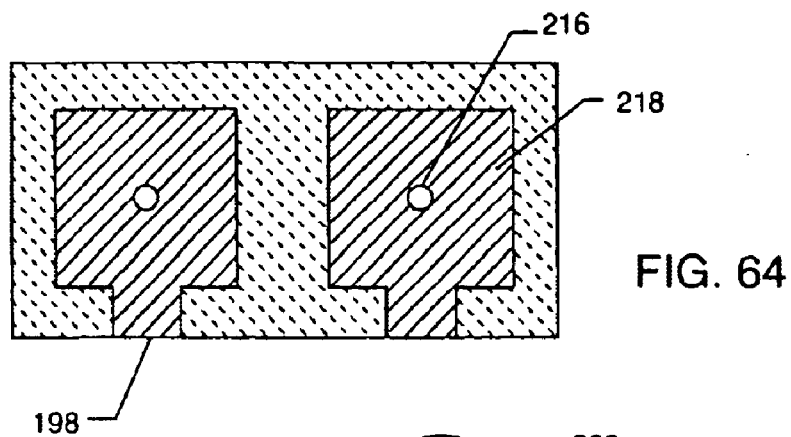
FIG. 64 is a cross-sectional view taken generally along the line 64—64 of FIG. 61, illustrating the configuration of active electrode plates within the capacitor.

FIG. 64 illustrates the active electrode plate sets 218 of the bipolar capacitor of FIG. 61. The two points where the active electrode plates 218 are brought to the outside perimeter of the capacitor 710 define the bonding areas 198, as shown in FIG. 61. Referring to FIG. 61, one can see the three exposed active electrodes 218 in the cutaway of the wire bond pad area 198 of FIG. 61. Moreover, FIG. 61, the number of active and ground electrodes acting in parallel determines and adjusts the capacitance value measured from each feedthrough hole 216 with reference to the ground metallization 212.

Figure 65:
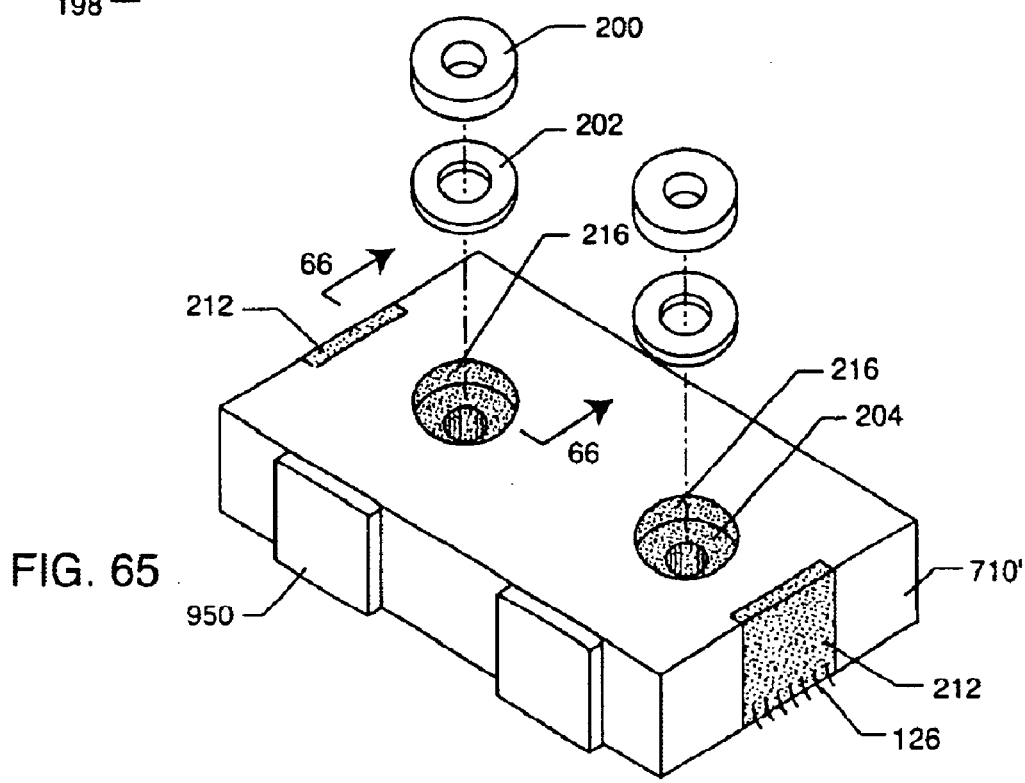
FIG. 65 is a partially exploded perspective view of a modified bipolar feedthrough capacitor similar to that shown in FIG. 61.
Figure 66:
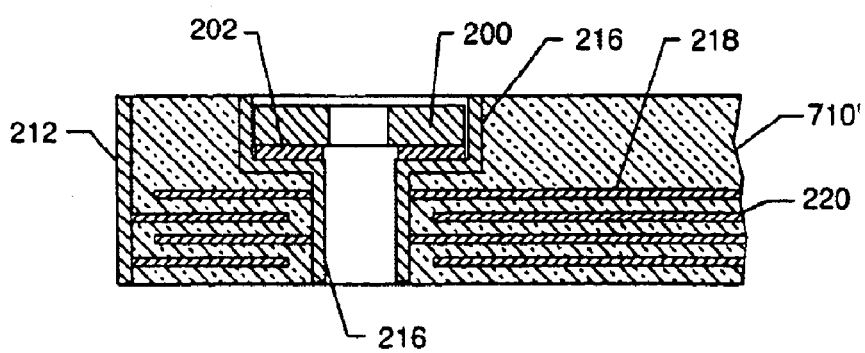
FIG. 66 is an enlarged, fragmented cross-sectional view taken generally along the line 66—66 of FIG. 65.

FIG. 65 illustrates a modification of the bipolar feedthrough capacitor of FIG. 61. The top view of the electrode plates 218 and 220 of the bipolar capacitor 710' of FIG. 65 are essentially the same as those previously, illustrated for FIG. 61 in FIGS. 63 and 64. Accordingly, the active electrode plate set 218 of the bipolar capacitor 710' of FIG. 65 is as shown in FIG. 64. The ground electrode plate set 220 of the bipolar capacitor 710' of FIG. 65 is illustrated in FIG. 63. However, the capacitor 710' of FIG. 65 has been modified to accept circular metal inserts 200 which are shown exploded in view FIG. 65. The insert ring 200 would typically be machined or formed of Kovar, Alloy 42 or equivalent metal. The insert ring 200 would be finished with a conductive plating, such as gold, electro tin, silver or the like. The ring 200 is designed to be gold brazed by using gold preform 202 to metallization surface 216 of the ceramic capacitor 710'. An alternative to gold brazing 202 would be to use solder, thermal setting conductive adhesives or the like. In order for there to be space for a counterbore 204 directly into the capacitor itself, the electrode plates 218 and 220 can be located below the point of the counterbore 204. This is best illustrated in the cross-sectional view of FIG. 65 which is shown in FIG. 66. In this cross-section, one can see insert ring 200 which has been electrically connected using material 202 to the inside diameter metallization 216 of the bipolar feedthrough capacitor 710'. As one can see, the electrode plates 218 and 220 have been located near the bottom of the capacitor 710', thereby providing room for the counterbore 204 in which ring 200 is seated. It will be obvious to one skilled in the art that the counterbore is not necessary. That is, the ring 200 could have also been situated on top and electrically connected to metallization band 262 of the feedthrough capacitor 710 as previously illustrated in FIG. 61.

An optional circumferential metallization band 262 as shown in FIG. 61 would facilitate the direct attachment of the circular ring 200 to the top surface of the FIG. 61 capacitor 710 that does not have the counterbore 204 as shown in FIG. 65.

With reference to FIGS. 61–66, a lead wire from pacemaker circuits 186 (not shown) could be directly attached to either the ring 200 or to bond pads 950. The ring 200 or pad 950 shield the capacitor 710' from damage due to attachment forces.

FIG. 67 illustrates a related but expanded embodiment of the present invention. In FIG. 67, a multi-layer substrate 940 embodies embedded circuit traces 246 at various levels within the laminated and sintered ceramic substrate 940. Multi-layer circuit boards and substrates are well known in the art and are used for a variety of purposes. In a preferred embodiment, substrate 940 is of alumina ceramic or fosterite or similar ceramic material. However, multi-layer substrate 940 could be constructed of any commonly used circuit board materials, including plastics, fiberglass, polyimides and the like. The multi-layer substrate 940 shown in FIG. 67 is shown co-bonded to a bipolar ceramic feedthrough capacitor 210.

FIG. 68 is a cross-sectional view of the multi-layer alumina ceramic substrate 940 taken generally along the section line 68—68, as shown. FIG. 68 illustrates two embedded circuit traces 246 which are typically of gold, molybdenum, tungsten or other suitable metallic conductor.

FIG. 69 shows the ground electrode plate set 220 of the multiplayer ceramic capacitor 210 shown in FIG. 67, and FIG. 70 illustrates the active electrode plate set 318.

Referring now back to FIG. 67, the circuit traces 246 are shown exposed on the edge of the bipolar substrate 940 underneath the partial cutaway view of the right-hand wire bond pad 950. Wire bond pad 950 is typically attached by gold brazing as previously described herein. In FIG. 67, there are two embedded circuit trace layers 246 contained within the substrate 940. In this particular embodiment, both circuit traces 246 are geometrically identical, redundant, and in parallel. Depending upon the implantable device application, there could be one, two or many more of the FIG. 68 parallel embedded circuit traces 246 as shown in FIG. 67. For example, in a cardiac pacemaker the pacing and biological sensing currents are relatively small. Accordingly, the DC resistance of these circuit traces is not particularly critical. Therefore, in the case of a cardiac pacemaker, only one or two parallel circuit traces 246, as illustrated in FIG. 67, would be required. However, in an implantable cardioverter defibrillator, very high currents are produced when the cardioverter defibrillator or ICD delivers high voltage discharge therapy to the heart. Accordingly, any voltage drop or energy loss across the resistance of the embedded circuit traces 246 would be problematic. Therefore, in the case of an ICD application, up to 10 or even more circuit traces 246 could be required. The resistance of an individual circuit trace 246 also depends upon its thickness, width, resistivity and length.

Referring now back to FIG. 67, in a preferred embodiment, the contact to the lead wires 136 would be by way of an embedded or surface (not shown) ring 200 and highly reliable laser weld connection 160 to lead wires 136.

FIG. 71 illustrates a very similar multi-layer substrate 1040 bonded on top of an internally grounded feedthrough capacitor 810 as previously discussed in FIGS. 45, 46, 47, 48 and 49. A similarity between FIG. 71 and FIGS. 45 and 49 is that in FIG. 71 the capacitor 810 is also internally grounded through a grounded lead wire 236. The hermetic terminal assembly that is included within FIG. 71 is as previously described in FIG. 45 in that ground pin 236 has been brazed or welded directly to the metallic ferrule 122. FIG. 72 is a top view of one of the two embedded circuit traces 246 contained within the multilayer alumina substrate 1040. FIG. 73 illustrates the ground electrode plates 320 of the internally grounded bipolar feedthrough capacitor 810 of FIG. 71. FIG. 74 illustrates the active electrode plate set 318 of the feedthrough capacitor 810 of FIG. 71.

Referring now back to FIG. 71, there are three wire bond pads 950 shown attached to the side of the alumina substrate 1040. The center wire bond pad 950', which is connected to circuit traces 346, provides a convenient ground point for attachment to the internal circuitry of the implantable medical device. This is because lead wire 236 is brazed or welded directly to the ferrule 122 of the hermetic terminal assembly. In many cases, implantable medical devices require a ground to the titanium housing 124 or equipotential surface. By providing a grounded wire bond pad 950 as shown in FIG. 71, this avoids the need to provide a special grounding location within the inside of the titanium housing of an implantable medical device. A laser weld 160 connects the embedded metal rings 200 to the lead wires 136. The metal ring 200 is typically plated and gold brazed to the via hole metallization 144 of the substrate 1040.

Figure 75:
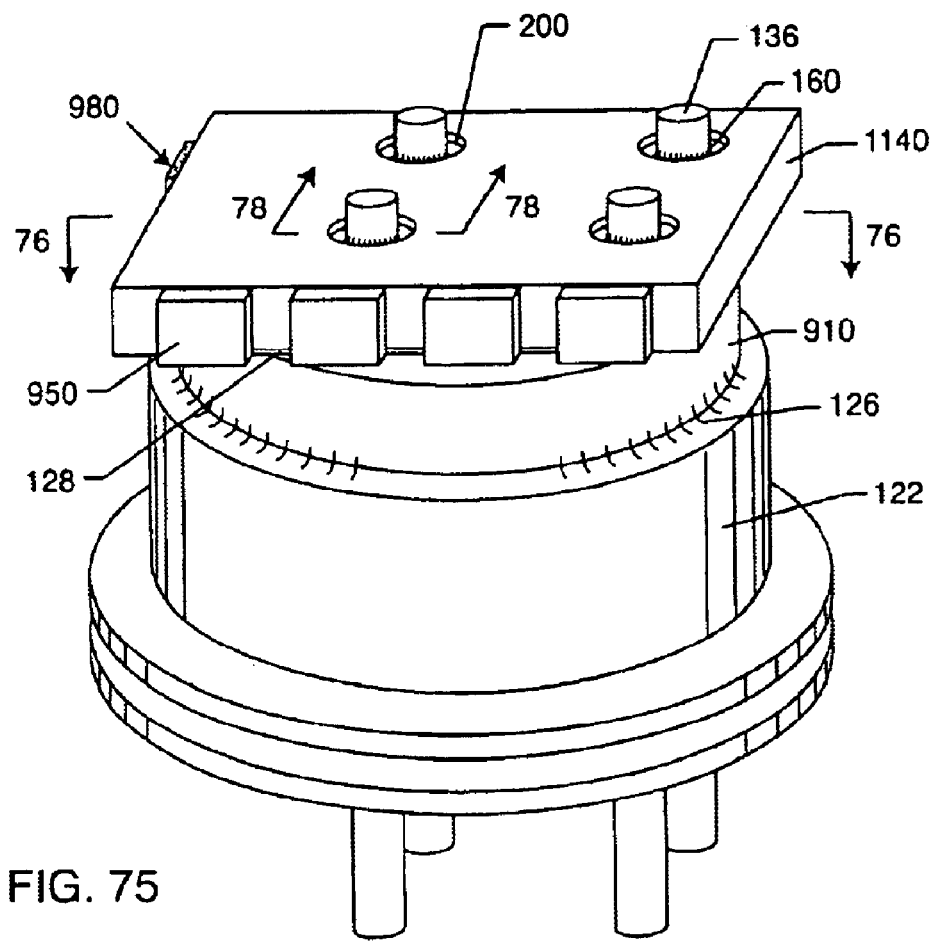
FIG. 75 is a perspective view illustrating a round quadpolar feedthrough capacitor assembly with a rectangular circuit substrate attached by co-bonding.

FIG. 75 illustrates a round quadpolar feedthrough capacitor 910 assembly with a rectangular circuit substrate 1140 of the present invention attached by co-bonding 128. There are a number of reasons why implantable device manufacturers often prefer circular geometry for the hermetic seal. One is the fact that these are easier to laser weld into the overall housing or can 124 (not shown) of an implantable medical device. However, when it comes to connecting the lead wires from internal circuits to a round feedthrough this is often not the optimal geometry. Hybrid circuit boards that are used in implantable medical devices are usually rectilinear in dimension. Accordingly, having wire bond pads 950 that are lined up along straight lines are often preferred. The embodiment shown in FIG. 75 solves this problem by adding a rectangular multi-layer substrate 1140 with wire bond pads 950 as shown.

Figure 76:
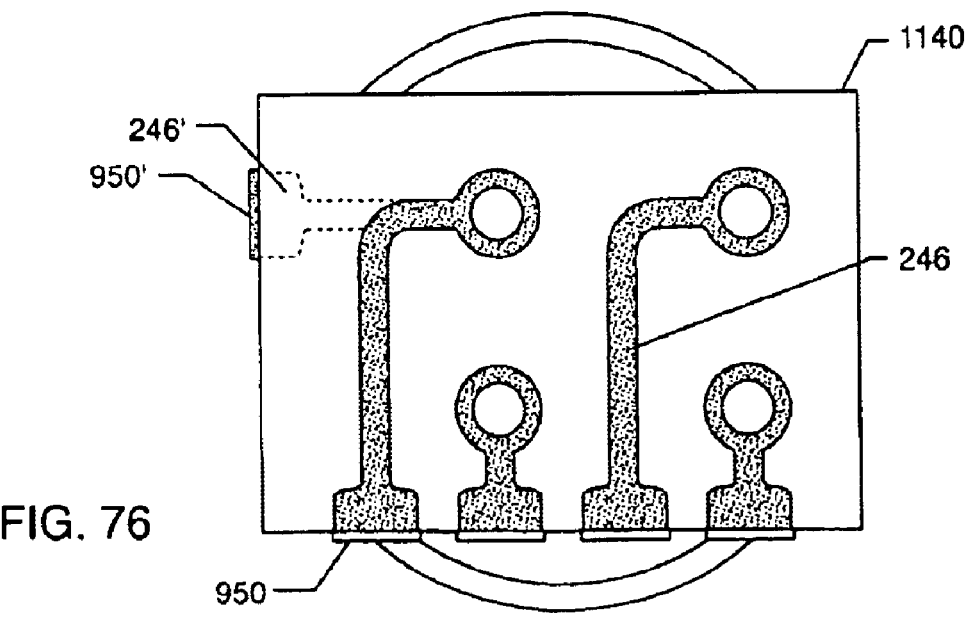
FIG. 76 is a sectional view taken generally along the line 76—76 of FIG. 75, illustrating one of four internal circuit traces at one level of the substrate.

FIG. 76 is a top down cross-section showing one of four internal circuit traces 246 at one level of the substrate 1140 of FIG. 75. As previously mentioned, there can be one or many of these identical circuit trace layers all acting in parallel within the multi-layer substrate 1140. An optional location for the circuit trace and wire bond pad 246' and 950' is shown to illustrate that these circuit traces can be run in any direction in which ones imagination allows. These are usually laid down by high production volume metal cladding, silk-screening or similar deposition methods.

Referring now back to FIG. 75, one can see that the round quadpolar feedthrough capacitor 910 has also been mounted and bonded 126 to the ferrule 122 of the hermetic terminal. In accordance with the present invention, the substrate 1140 is co-bonded using a nonconductive adhesive polyimide washer 128 to the surface of the ceramic capacitor 910.

Figure 77:
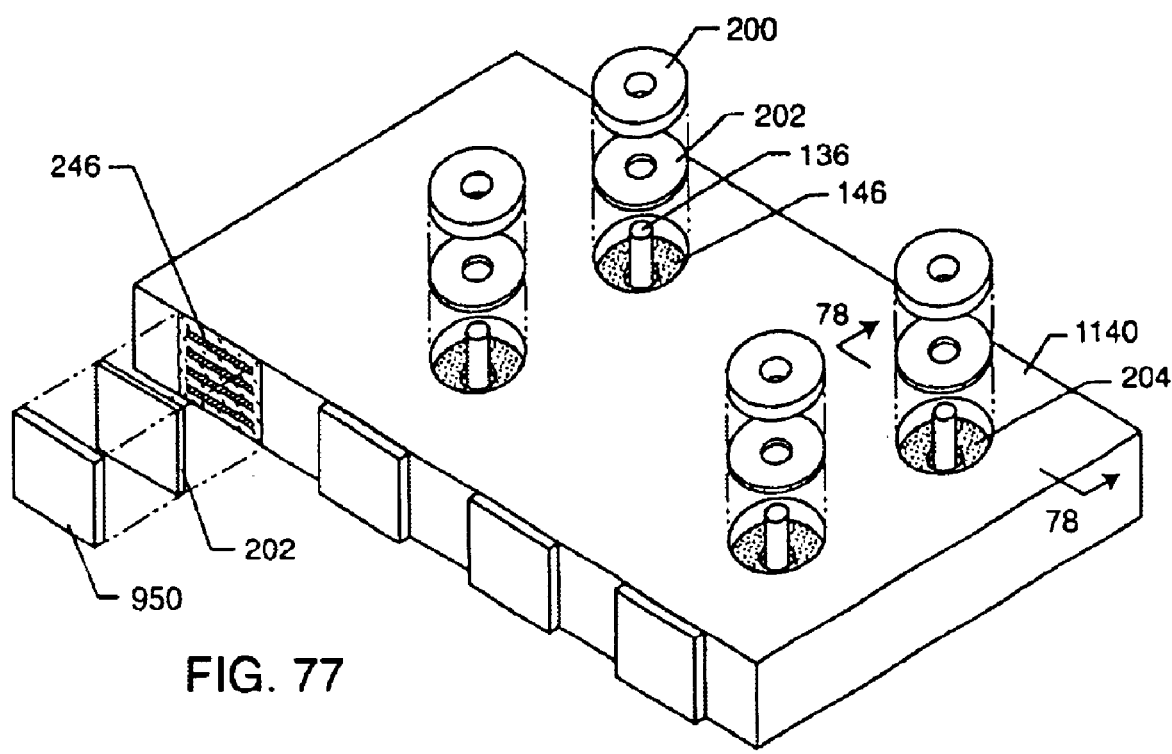
FIG. 77 is an enlarged and partially exploded perspective view of the alumina substrate of FIG. 75, illustrating the methodology of application of the wire bond pads to the alumina substrate.

FIG. 77 illustrates the methodology of application of the wire bond pads 950 to the alumina substrate 1140 of FIG. 75. As one can see, in this case there are four parallel embedded circuit traces 246. As mentioned, these act in parallel reducing the overall DC resistance and inductance of the circuit. The wire bond pad 950 is typically of Kovar, Alloy 42 or similar construction which has been nickel and then gold plated. A gold preform 202 is used to attach the Kovar pad 950 to metallization which covers the circuit traces 246 (metallization not shown). This operation is typically performed in a gold brazing furnace. FIG. 77 also illustrates a metallic ring 200 which is gold brazed to metallization 146 on the inside diameter surface of the counterbore 204 of the alumina substrate 1140. As previously described, and as illustrated in FIG. 75, the most reliable connection is a laser weld 160 between the lead wire 136 and the metallic ring 200.

Figure 78:
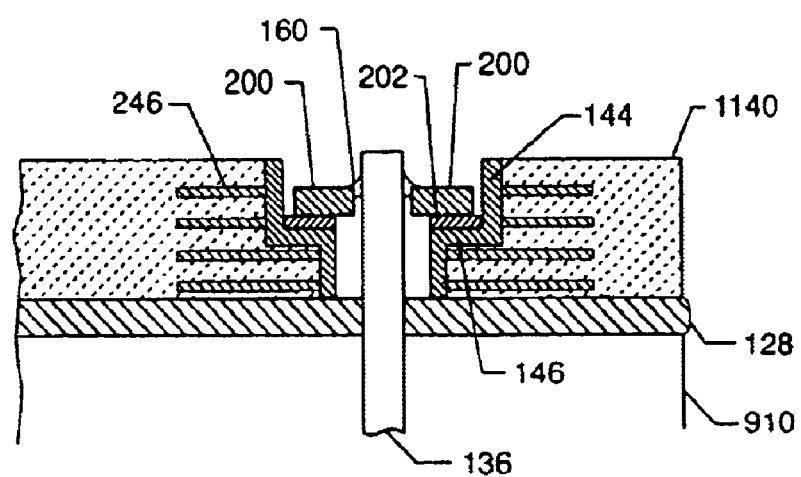
FIG. 78 is an enlarged, fragmented cross-sectional view taken generally along the line 78—78 of FIG. 75.

FIG. 78 is a cross-sectional view of this metallic ring 200 shown attached to the lead wire 136 with a laser weld connection 160. The cross-sectional view of FIG. 78 also shows the end view of the four embedded circuit traces 246 which electrically connect to the inside diameter via hole metallization 144 and 146. As mentioned, the metal ring 200 would typically be of Kovar or Alloy 42 and gold brazed 202 to the via hole metallization 146. In the cross-section shown in FIG. 78, one can also see the nonconductive bonding washer 128 which is attached to the top surface of the feedthrough capacitor 910 (not shown).

Figure 79:
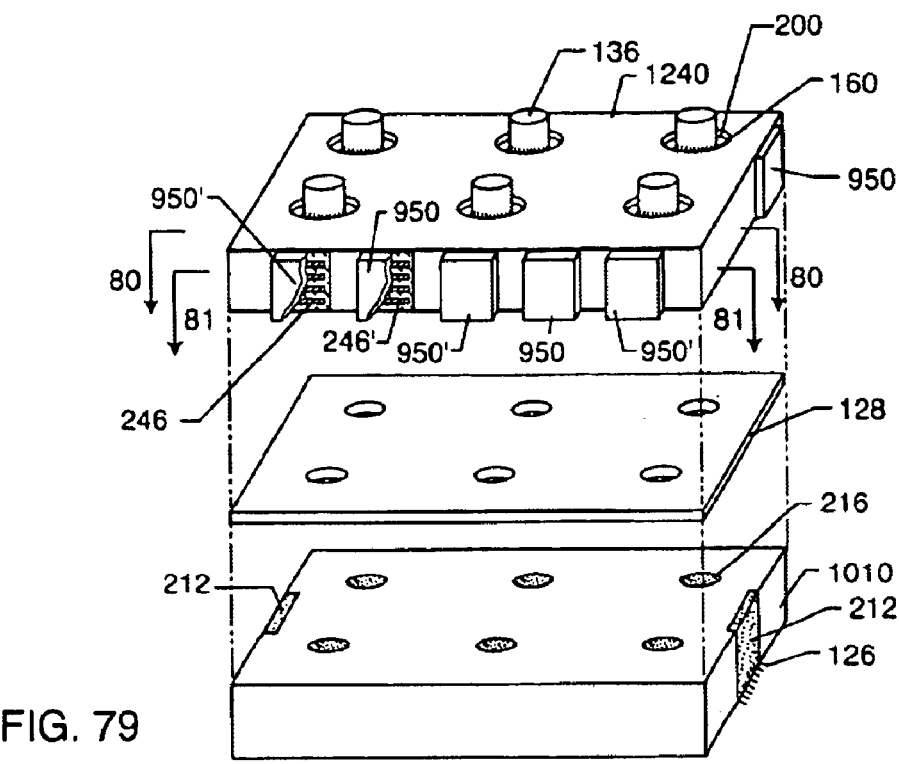
FIG. 79 is an exploded perspective view of a rectangular hexpolar substrate and related capacitor, in accordance with the present invention.
Figure 80:
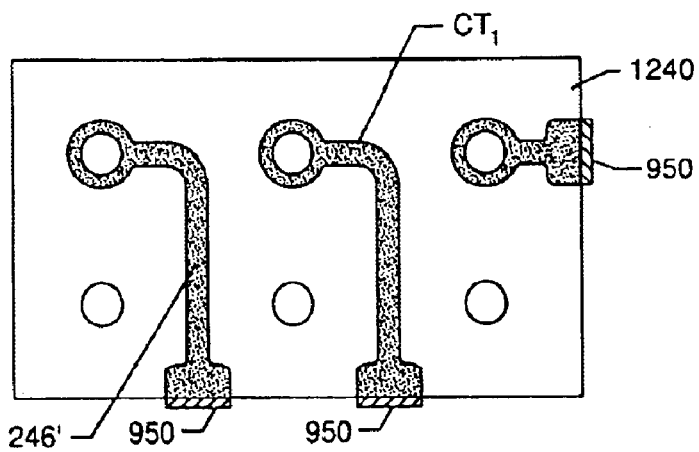
FIG. 80 is a cross-sectional view through the substrate taken generally along the line 80—80 of FIG. 79.
Figure 81:
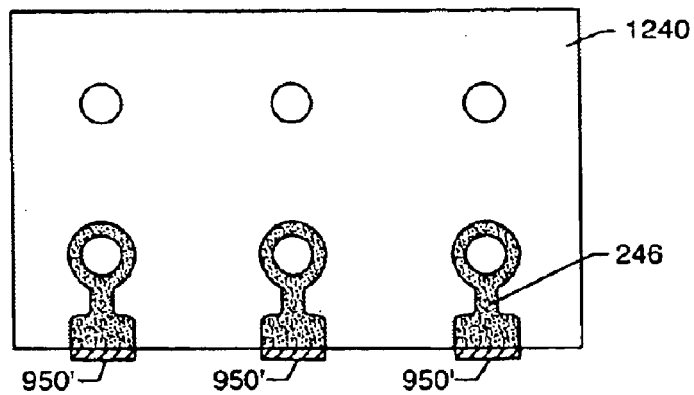
FIG. 81 is a cross-sectional view taken generally along the line 81—81 of FIG. 79.

FIG. 79 illustrates a rectangular hexpolar substrate 1240 of the present invention. As shown, there are a total of six wire bond pads 950 and 950' shown in various locations around the perimeter of the substrate 1240. As previously described, the substrate 1240 is designed to be co-bonded using an insulating washer 128 to the top surface of the hexpolar feedthrough capacitor 1010. The lead wires 136, as shown in FIG. 79, are shown broken off in the substrate 1240 for illustrative purposes only and, of course, would actually protrude upward from a hermetic feedthrough terminal (not shown) of an implantable medical device to which feedthrough capacitor 1010 is mounted or bonded. These lead wires 136, in the preferred embodiment, would be attached to embedded or surface (not shown) rings 200 as previously described in FIGS. 77 and 78 with attachments 160 by laser welding. A novel aspect of the multi-layer substrate 1240 shown in FIG. 79, is that its embedded circuit traces 246 and 246' need not be the same on different substrate levels. For example, FIG. 80 illustrates the circuit trace 246' on a first cross-section level of the substrate 1240 FIG. 79. FIG. 81 illustrates the circuit traces 246' on a different level. As previously mentioned, a number of these embedded circuit traces 246 and 246' can be placed in parallel to lower the overall DC resistance. For example, there might be five 246 layers in parallel to handle the output of an implantable defibrillator and only one 246' layer to handle the cardiac sensing and pacing currents which would be of very low current. As one can see, having different geometries on different circuit trace layers, allows one great latitude and flexibility in designing a filtered hermetic terminal for an implantable medical device. This is particularly important in an implantable cardioverter defibrillator where voltages are quite high. In this regard, adjusting the number, thickness and length of the circuit traces on differing levels is utilized to adjust the overall resistance and current handling capability of the active implantable medical device. Using the techniques described, in FIGS. 80 and 81, one can be sure the circuit traces 246 and 246' are placed widely apart, but at various levels within the substrate 1240 so that they do not have any chances of arcing or shorting out.

Referring now back to FIG. 79, one can see that the wire, bond pads 950' are attached to circuit traces 246 as shown in FIG. 81, and wire bond pads 950 are attached to circuit traces 246' as shown in FIG. 80. There are literally an infinite number of possible circuit trace geometries on various levels as will be obvious to one skilled in the art.

Figure 82:
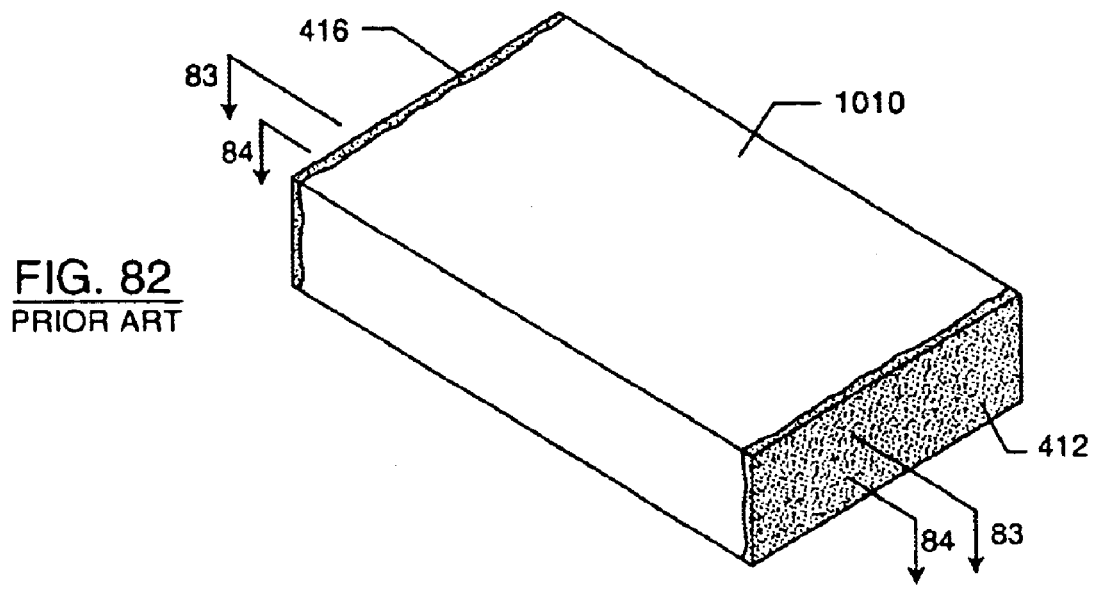
FIG. 82 is a perspective view of a prior art monolithic chip capacitor.

FIG. 82 is a prior art monolithic ceramic chip capacitor (MLCC) 1010. This is also known as a two-terminal capacitor (feedthrough capacitors are three terminal capacitors).

Figure 83:
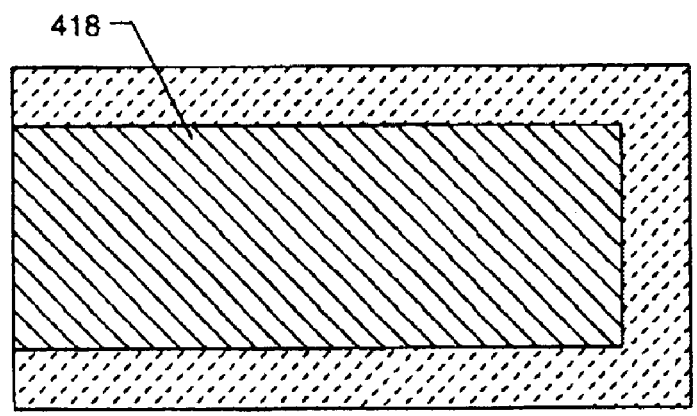
FIG. 83 is a horizontal cross-sectional view generally along line 83—83 through the capacitor of FIG. 82, illustrating the configuration of a first set of electrode plates.
Figure 84:
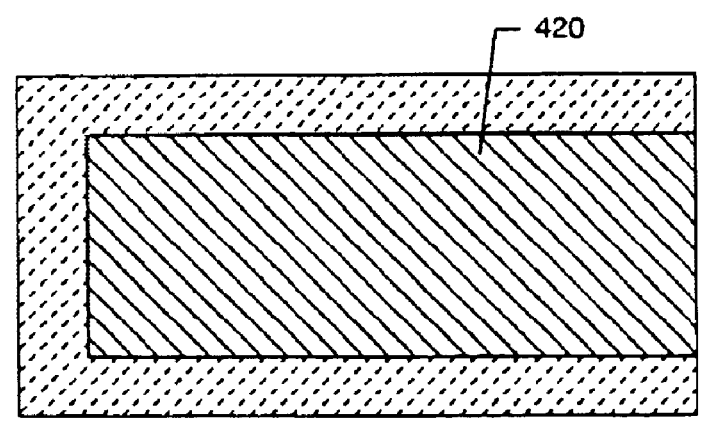
FIG. 84 is a horizontal sectional view taken through the capacitor of FIG. 82, illustrating the configuration of second set of electrode plates.

FIG. 83 shows one electrode plate set 418 of the prior art MLCC 1010 of FIG. 82. FIG. 84 shows the opposite electrode plate set 420 of the MLCC 1010 of FIG. 82.

MLCCs (two-terminal devices) are generally not desirable EMI filters in that they have a substantial amount of series inductance. This means that they will self resonate or series resonate at a particular frequency. For example, for an industry standard 0805 chip, which is 0.080 inch long by 0.050 inch wide, the self-resonance frequency is typically around 150 MHz. This means that at cellular telephone frequencies; for example, above 900 MHz, the chip capacitor 1010 as shown in FIG. 82 is really no longer a capacitor. That is, above its resonant frequency it becomes increasingly inductive. Therefore, it does not make an effective low pass EMI filter element at very high frequency. Nevertheless, such rectangular chip capacitors 1010 as shown in FIG. 82 are used in a variety of lower frequency filtering applications.

Figure 85:
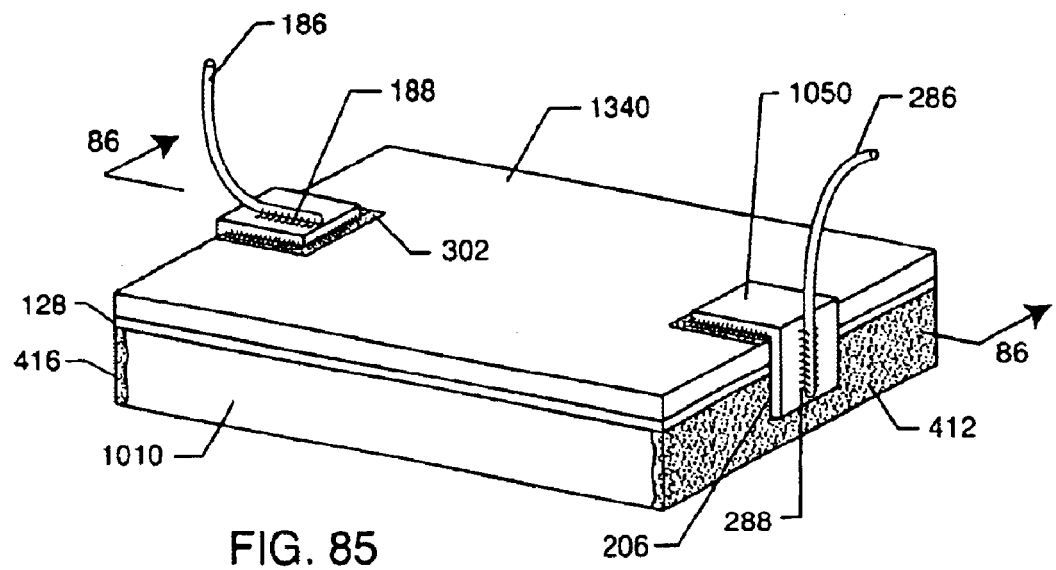
FIG. 85 is a perspective view illustrating the co-bonding of a substrate of the present invention to the prior art monolithic chip capacitor of FIG. 82.
Figure 86:
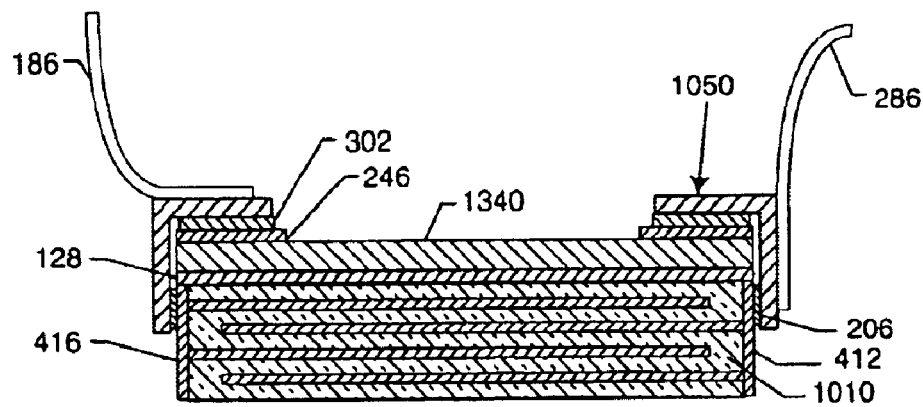
FIG. 86 is a cross-sectional view taken generally along the line 86—86 of FIG. 85.

FIG. 85 illustrates the co-bonding of a substrate 1340 of the present invention to the prior art monolithic chip capacitor 1010 of FIG. 82. As one can see from FIG. 85, L-shaped wire bond pads 1050 have been provided in order to make electrical contact to the capacitor electrode metallization surfaces 412 and 416. There is an electrical connection material 206 that is better illustrated in the cross-sectional view of FIG. 85 shown in FIG. 86. Electrical connection material 206 makes electrical connection between the wire bond pad 1050 and the capacitor end metallizations 412 and 416. As shown in the cross-sectional view in FIG. 86, the substrate 1340, which is preferably alumina or aluminum oxide, is co-bonded to the ceramic capacitor 1010 using an adhesive backed polyimide washer 128.

Referring now back to FIG. 85, one can see that wire bonds 188 and 288 have been formed between wire 186 and wire 286 to the gold plated wire bond pads 1050. In order to make sure that ultrasonic or thermosonic wire bond forces do not fracture the ceramic capacitor 1010, the wire bond pad 1050 is also desirably gold brazed to the top surface of the alumina substrate 1340. This will help to make sure that mechanical vibration forces are properly dissipated with the alumina substrate 1340. This is also illustrated in the cross-section shown in FIG. 86. In this cross-section, one can see the gold or CuSil braze 302 which connects the wire bond pad 1050 to the top surface metallization 246 of the alumina substrate 1340.

Figure 87:
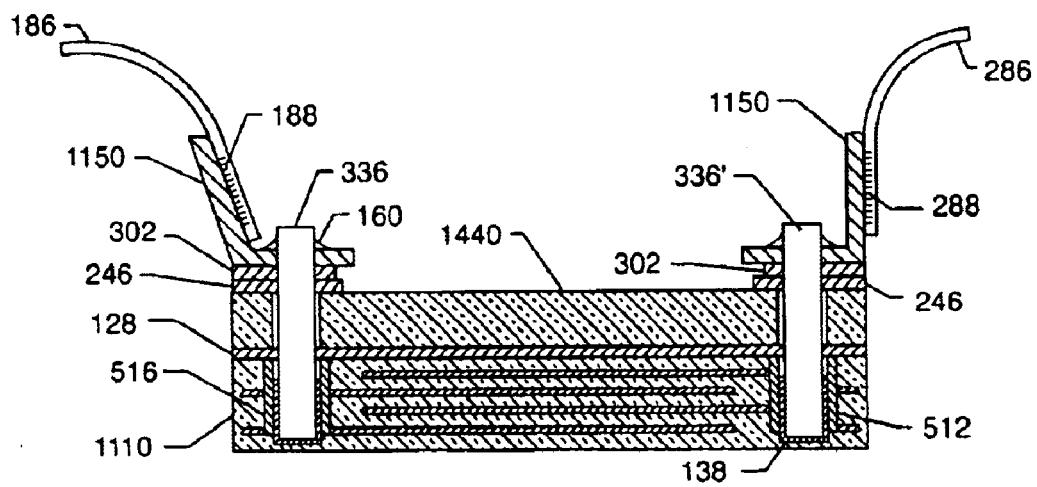
FIG. 87 is a cross-sectional view similar to that shown in FIG. 86, illustrating an alternative embodiment wherein the prior art monolithic chip capacitor of FIG. 82 has been modified with two blind holes.

FIG. 87 illustrates an alternative embodiment wherein a prior art monolithic chip capacitor 1110 similar to FIG. 82 has been modified by drilling two blind holes as shown. Short pins 336 and 336' are placed into these two holes and electrically connected to the interior electrode plates metallization 512 and 516 by electrical connection material 138. Electrical connection material 138 can be solder, thermal setting conductive adhesives or the like. The electrical connection material 138 makes electrical contact between the pin 336 and 336' and the inside diameter metallization 516 and 512 of the rectangular chip capacitor 1110. The L-shaped (angled) wire bond pads 1150 have been attached by gold brazing 302 to the top surface metallization 246 of the ceramic substrate 1440.

It should be noted that the capacitor 1110 that is illustrated in FIG. 87 is not a feedthrough capacitor. It has the same two-terminal device self resonance problems as described for the prior art chip capacitor 1010 of FIG. 82.

Figure 88:
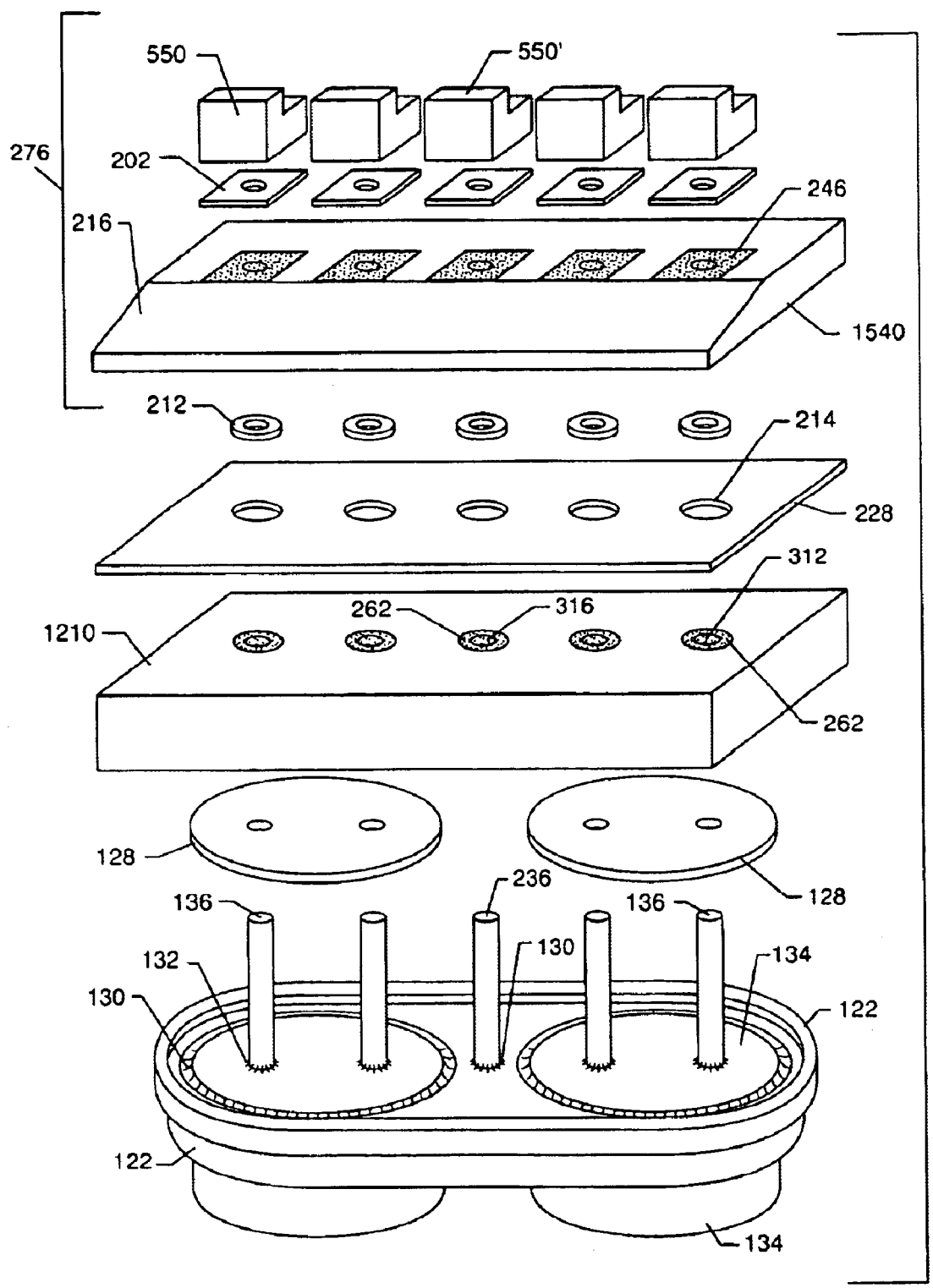
FIG. 88 is an exploded perspective view of an internally grounded quadpolar feedthrough capacitor embodying the present invention.

FIG. 88 illustrates an exploded view of an internally grounded quadpolar plus ground pin EMI filter hermetic terminal for human implant applications. The internally grounded feedthrough capacitor 1210 has four active feedthrough pins 136 and one ground pin 236. The ground pin 236 is shown welded to ferrule 122 in the center which is desirable to minimize the inductance for proper de-coupling of EMI through the active electrode plates. Internally grounded feedthrough filter capacitors are well known in the art as described by U.S. Pat. Nos. 6,529,103 and 5,905,627.

With continuing reference to FIG. 88, one can see that alumina substrate 1540 of the present invention has rectangular metallized areas 246 for convenient attachment of wire bond pads 550 and 550' to these metallized areas using braze preforms 202. The wire bond pads 550 and 550' would typically be attached to substrate 1540 as a first step by reflowing the braze preforms 202 in a high temperature vacuum brazing furnace. The next step would be to assemble the capacitor 1210 to hermetic seal 122, 134 using a sandwich construction by first inserting the two nonconductive adhesive coated polyimide preforms 128 over the lead wires 136 and seating them against each of the alumina insulators 134. The internally grounded feedthrough capacitor 1210 would then be placed over the five lead wires 136 and 236 of the hermetic terminal assembly. Adhesive coated nonconductive polyimide insulating washer 228 would then be put in place and the solder or thermosetting conductive preforms 212 would be loaded so that they seat inside the through holes 214 of insulating washer 228 and against the top capacitor metallization 262. The pre-assembly 276 consisting of the substrate 1540 with the gold braze wire bond pad 550 would then be slipped in place over the five lead wires 136. Metallization 246 on the bottom of the substrate 1540 (not shown) is designed to press up against the five solder or thermosetting conductive adhesive preforms 212. Electrical connection is made from this bottom metallization of substrate 1540 up through each one of its metallized via holes so that there is a continuous electrical connection to the top surface metallization 246. Because of the gold braze 202 attachment of the wire bond pads 550 and 550', this means that there will be a continuous electrical circuit from wire bond pads 550 and 550' through to the top metallization 262 of the feedthrough capacitor 1210 and in turn to the inside diameter metallization 312 of the internally grounded feedthrough capacitor 1210. This sandwich as shown exploded in FIG. 88 is then clamped together and cured at a high temperature such that the nonconductive bonding washers 228 and 128 are cured and that the solder preforms or thermosetting conductive polyimide preforms 212 are either reflowed or cured as well.

Figure 89:
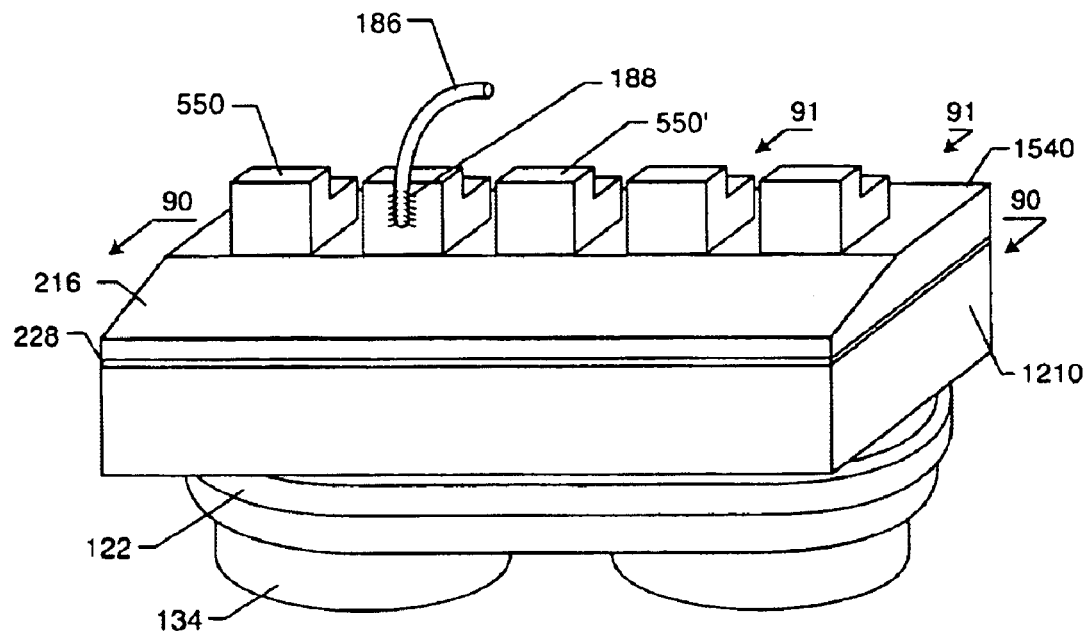
FIG. 89 is a perspective view of the assembled feedthrough terminal assembly of FIG. 88.

FIG. 89 illustrates the completed assembly of FIG. 88. For illustrative purposes a lead wire 186, which would be routed from the internal circuits of an implantable medical device such as a cardiac pacemaker, is shown wire bonded 188 to one of the wire bond pads 550. Wire bonding equipment, including automated systems with robotic controls typically have a rather large feed head through which the wire to be bonded protrudes. The wire bond equipment feed head tapers to a point and is somewhat conical in cross-section. Accordingly, substrate 1540 has been tapered down into area 216 thereby providing sufficient space for the wire bond head to come in and properly engage the leads 186 and wire bond pads 550. This is a novel aspect of the present invention that can be adapted to many other of the substrates that are described in this patent application. The center wire bond pad 550' is grounded to ferrule 122 of the hermetic terminal.

Referring now back to FIG. 88, one can see by observing lead wire 236 and gold braze or weld 130 that lead wire 286 is both mechanically and electrically connected to the center of overall metallic ferrule structure 122. Lead wire 236 is necessary for the internally grounded feedthrough capacitor 1210 in order to ground its internal electrode plates.

Wire bond pad 550' is not necessary in all implantable medical devices. In certain cardiac pacemakers and implantable defibrillators, a convenient grounding location is an important feature. For example, in an implantable defibrillator cardioverter, where the titanium housing of the device can also be a cardiac shock electrode, a low resistance connection must be made from the high voltage output circuitry of the implantable defibrillator to its overall titanium housing 124. Accordingly, wire bond pad 550' provides a convenient place to make such a connection. The rest of this shock electrode circuit is completed by laser welding the ferrule 122 into the overall housing or titanium shield 124 of the implantable medical device (not shown).

Figure 90:
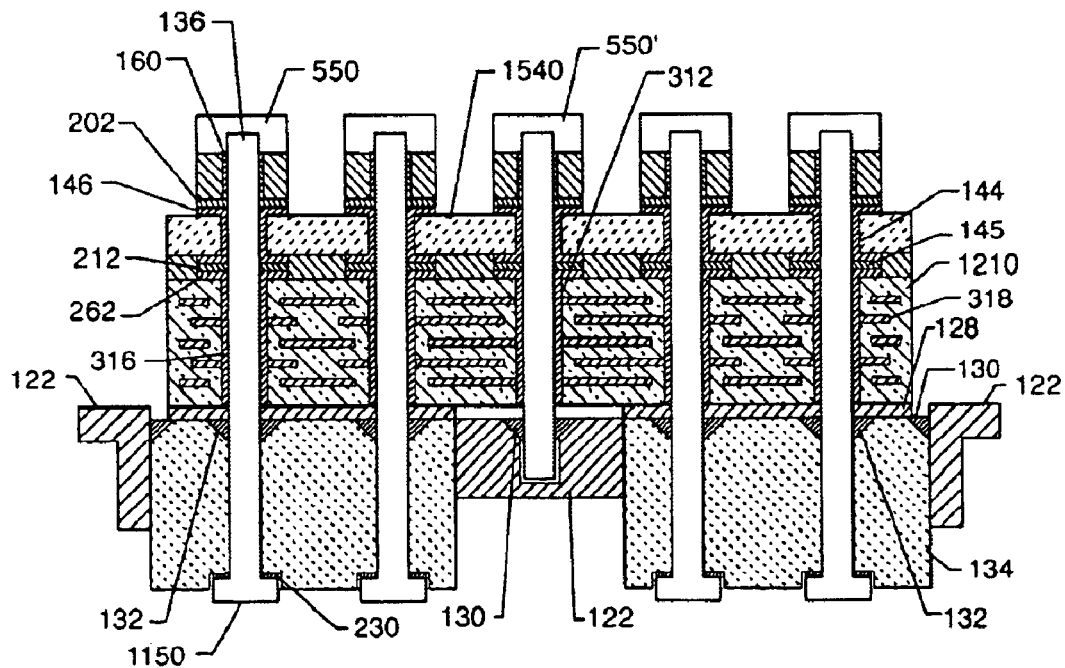
FIG. 90 is a cross-sectional view taken generally along the line 90—90 of FIG. 89.

FIG. 90 illustrates a cross-sectional view of the quadpolar plus ground pin assembly of FIG. 89. Referring to FIG. 90, one can see that the capacitor 1210 has been solidly bonded to the alumina insulator 134 of the hermetic terminal using two nonconductive insulating washers 128. Wire bond pads 550 have been attached by brazing material 202 to the top metallization 146 of the alumina substrate 1540.

Close examination reveals that the electrical connection material 212 which is sandwiched between the bottom surface alumina substrate metallization 145 and the top metallization 262 of the ceramic capacitor 1210 provides an electrical connection from wire bond pad 550 to the capacitor feedthrough hole inside diameter metallization 316 and in turn to its active electrode plates 318. This provides a low impedance RF circuit which enables feedthrough capacitor 1210 to perform as an effective high frequency EMI filter. A laser weld connection 160 is made between lead wire 136 and the wire bond pad 550 or 550' to complete the rest of the electrical circuit.

Wire bond pads 1150 can be placed on the body fluid side of the EMI filtered hermetic terminal assembly and are brazed 230 directly to the alumina insulator 134. Human body fluid is very corrosive. Accordingly, the wire bond pads 1150, the braze 230 and the underlying lead material 136 must be of suitable biocompatible material. Such materials include the group of platinum, niobium, gold, tantalum, titanium, stainless and their various alloys including alloys containing iridium and nickel.

Attachment of lead wires 186 (not shown) to the body fluid side wire bond pads 1150 is preferably done by direct lead wire welding or brazing. These lead wires would typically connect from the wire bond pads 1150 to the connector or header block (not shown) of a cardiac pacemaker and the like. If attachment to wire bond pads 1150 is by mechanical attachment, ultrasonic bonding or thermosonic bonding, then wire bond pads 1150 would either be of gold or would require an ultra-pure gold over plating.

Figure 91:
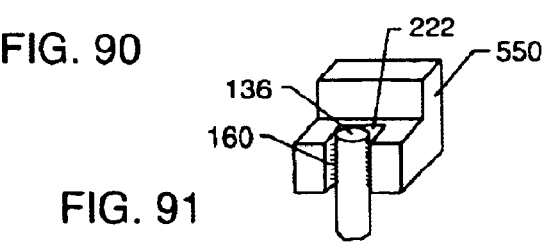
FIG. 91 is a perspective view of modified L-shaped wire bond pad taken generally of the structure illustrated by the line 91 in FIG. 89.

FIG. 91 illustrates a rotated close up view of one of the wire bond pads 550 of FIG. 89. As one can see, the laser weld area 160 is relatively long about both sides of the lead wire 136. This not only makes a highly reliable electrical connection, but is also easy to manufacture. This is because there is a natural fillet area that is formed between the outside diameter of lead wire 136, and the inside of the slot 222 which has been conveniently machined or stamped into the wire bond pad 550. As previously mentioned, it would be typical that wire bond pad 550 be of Kovar, Alloy 42, or other metallic material. Wire bond pad 550 would typically be first nickel plated and over plated with an ultra pure soft gold.

Figure 92:
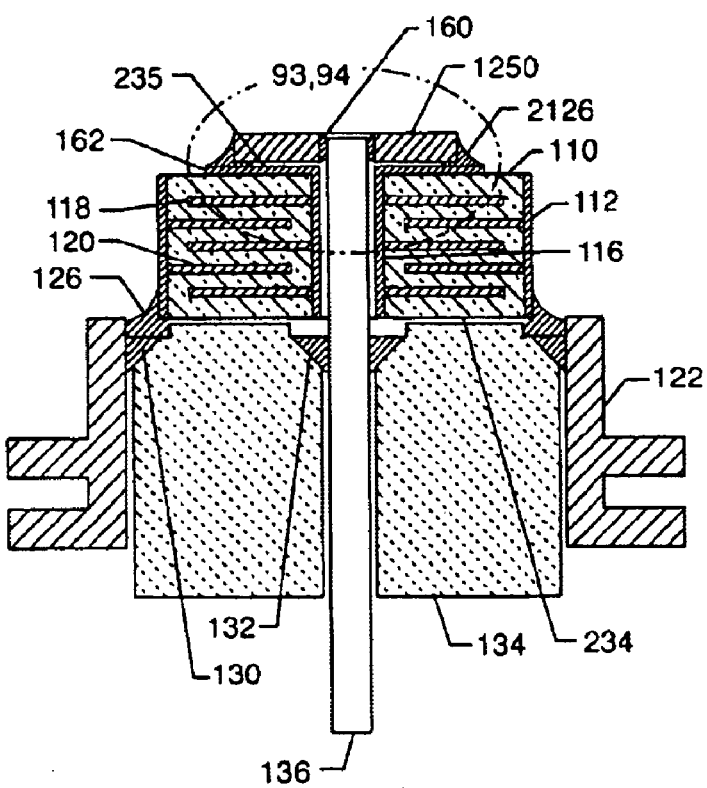
FIG. 92 is a cross-sectional view of another unipolar hermetic terminal embodying the invention.

FIG. 92 illustrates another embodiment of the present invention. Shown is a unipolar hermetic terminal with a unipolar feedthrough capacitor 110 shown attached. The novel aspect shown in FIG. 92 is that there are no nonconductive insulating washers that have been described in previous figures. The unipolar feedthrough capacitor 110 as illustrated in FIG. 92 is very simple to manufacture. A unique feature is the pedestal area which is the protruding part of the alumina insulator 134 labeled as 234. Alumina ceramic insulators can be machined, made of pressed powders and then fired, or laser cut. Accordingly, forming of the pedestal area 234 is a relatively easy and inexpensive manufacturing operation. As previously described, laser welds 130 and 132 make a mechanical and hermetic seal connection between alumina insulator 134 and both the ferrule 122 and lead wire 136. Manufacturing of the unipolar EMI filter capacitor assembly as shown in FIG. 92 is relatively simple. All that is involved is to drop capacitor 110 over lead wire 136 and then also place wire bond cap 1250 on top of capacitor 110. Fixturing would then apply pressure to center and push down on wire bond pad 1250 while automated equipment formed the laser weld 160 as shown. At this point the ceramic capacitor is captured between the pedestal area 234 of the alumina insulator 134 and the wire bond pad 1250. It is then easy to either manually or robotically dispense a thermosetting conductive polymer 2126 and 126 both around the outside diameter of the Kovar pad 1250 and the capacitor outside diameter termination 112 as shown. The connection material 2126 makes electrical contact between the wire bond pad 1250 and the top metallization ring 162 of the ceramic capacitor 110. The top metallization ring 162 forms a continuous electrical connection to the capacitor inside diameter metallization 116 and to the active electrodes 118 of the feedthrough capacitor 110.

Referring now to the outside diameter of feedthrough capacitor 110, electrical connection material 126 makes an electrical contact between the outside diameter termination 112 of the feedthrough capacitor 110 and the gold braze area 130 of the hermetic terminal ferrule 122. The outside diameter metallization 112 of the capacitor 110 is electrically connected to its ground electrode plates 120. Co-pending U.S. patent application Ser. No. 10/377,086 describes the importance of making electrical contact to a gold surface instead of directly to the titanium ferrule 122. This is because titanium is notorious for forming oxides which could preclude the proper performance of the EMI filter at high frequency.

An alternative method of assembling the unipolar capacitor 110 shown in FIG. 92 would be to first pre-assemble the wire bond cap 1250 to the ceramic capacitor 110 by making the mechanical and electrical connection 2126 to the top metallization 162 of the feedthrough capacitor 110. In this way the capacitor and Kovar pad assembly could be tested and then stored in inventory. When it came time to attach this pre-assembly to the hermetic terminal, all that would need to be done is to mount the assembly in place and perform the laser weld 160 to lead wire(s) and make the electrical connection 126 ground the capacitor outside diameter termination 112 as previously described.

As mentioned, the assembly of FIG. 92 does not incorporate the nonconductive bonding washers 228 used in previously described embodiments. This results in a space or air gap 235 between the wire bond cap 1250 and the capacitor 110. This gap is very small but could present a concern where contaminants could be trapped. Accordingly, the assembly of FIG. 92 is best suited for low voltage pacemaker applications.

Again referring to FIG. 92, one can see that a disadvantage of the wire bond cap 1250 shown is that it has a central through hole where the laser weld connection 160 is made to lead wire 136. This reduces the top surface contact area of the wire bond pad 1250 that is available for subsequent wire bonding to the lead wires of the internal circuits of the implantable medical device.

Figure 93:
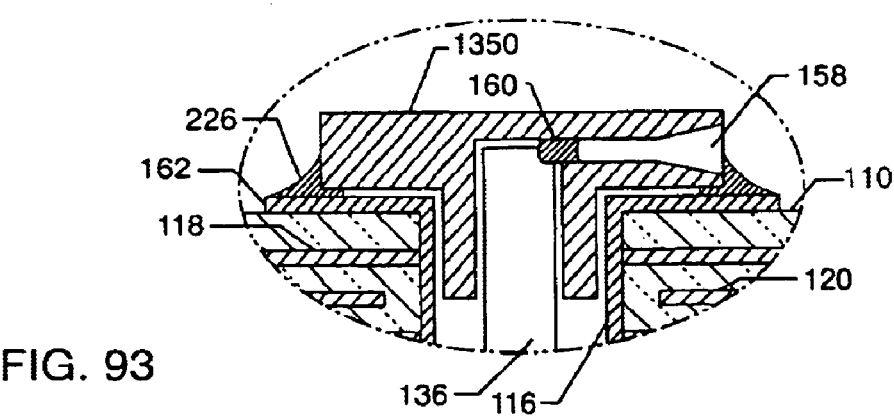
FIG. 93 is an enlarged sectional view of an alternative structure taken along the line 93—93 in FIG. 92.

In the case where additional surface area would be required, a preferable wire bond pad 1350 is as described in FIG. 93. FIG. 93 illustrates an alternative wire bond cap 1350 that can be used in conjunction with a unipolar capacitor previously described in FIG. 92. The wire bond pad 1350 as illustrated in FIG. 93 has a previously described aperture 158 for convenient laser welding 160 of the wire bond cap to lead wire 136.

Figure 94:
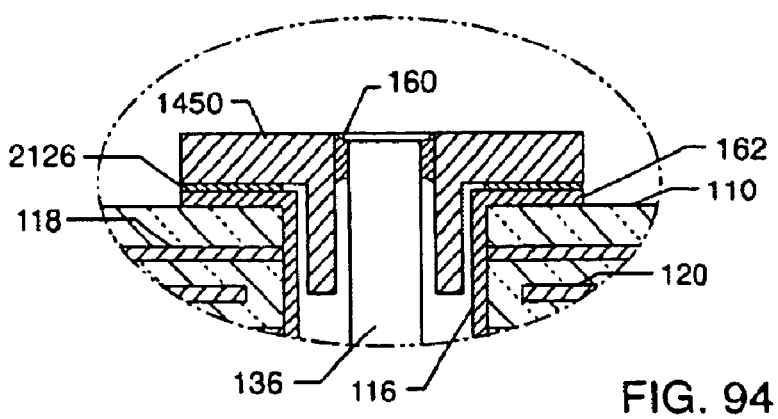
FIG. 94 is an enlarged sectional view of an alternative structure taken along the line 94—94 in FIG. 92.

FIG. 94 illustrates an alternative method of making the electrical connection 2126 between wire bond pad 1450 and the top metallization 162 of the feedthrough capacitor 110 of FIG. 92. Referring back to FIG. 92, the electrical connection 2126 was formed around the outside diameter of wire bond pad 1250 to the capacitor top metallization 162. In FIG. 94 one can see that the electrical connection material 2126 has been placed in sandwich type construction between the bottom of the flange of the wire bond pad 1450 and the top metallization of the capacitor 162. This material can be a thermosetting conductive adhesive, solder or the like.

The wire bond pads as described herein can also be used without a capacitor interposed between the alumina substrate and the body of the hermetic terminal. The wire bond substrate can be separated or bonded directly to the ferrule or insulator of the hermetically sealed terminal assembly using a nonconductive adhesively coated material as described herein. Other embodiments can include modifications of the alumina insulator of the hermetic terminal such that it incorporates wire bond pads.

Wire bond pads can also be put on the opposite or body fluid side of the hermetic terminal insulator. This can be done by co-bonding the alumina substrate with wire bond pads of the present invention or as mentioned, the alumina insulator itself can be modified to incorporate an embedded wire bond pad or even embedded circuit traces.

With reference now to FIGS. 95–100, it is also possible for the substrate to be of the group of nonconductive polyimides. Polyimide is an ideal molecule for the present invention in that it forms a ring molecule. This is in contrast to epoxies that form long string molecules. A ring molecule tends to be very stress absorbing and can expand and contract during application of external forces, such as when the lead wire 186 is attached to the assembly. Thus, the polyimide will act to absorb and dissipate stresses before they can reach the surface of the ceramic capacitor 110. Accordingly, the nonconductive polyimide type of substrate forms an ideal buffer between the wire bonding forces and the relatively fragile ceramic capacitor.

Figure 95:
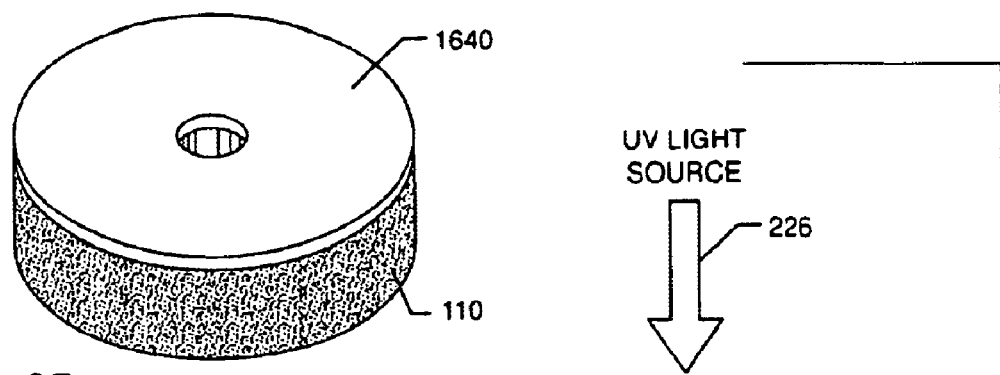
FIG. 95 is a perspective view of a capacitor having a substrate applied thereto.

With reference now to FIG. 95, a perspective view of a feedthrough capacitor 110 is shown with a layer of uncured polyimide 1640. The polyimide 1640 can comprise a washer substantially matching the configuration of the capacitor 110, or more preferably a top coating of liquid polyimide material 1640. The polyimide 1640 can be flooded over the entire surface of the capacitor 110 as a liquid, or by a spin application wherein droplets of material 1640 are placed while the entire structure 110 is spun at a low RPM. This flings off excess material 1640 and leaves a very uniform coating. In any event, the polyimide coating 1640 is curable, such as by heat or ultraviolet light or the like.

Figure 96:
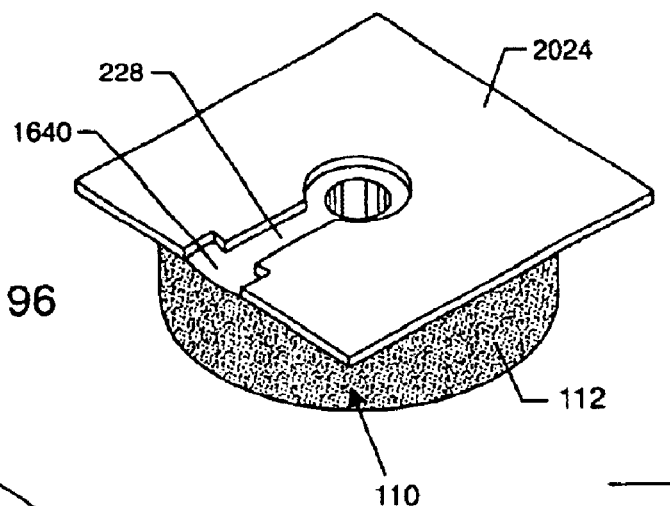
FIG. 96 is a perspective view of a mask overlying the substrate and being exposed to a radiation source.

One such manufacturer of a UV curing polyimide is HD Microsystems, material #PI-2730. In using such material, the nonconductive polyimide material 1640 is applied in a liquid or viscous state. The next step, illustrated in FIG. 96, is to bring a mask 2024 in close proximity to the top of the feedthrough capacitor 110. A UV light source 226 is then directed down on top of this mask 2024, which exposes the area in the cut out 228 of the mask 2024 to cure the exposed area of the polyimide 1640. Once the curing operation is completed, the mask 2024 is removed to be used again and again. A cleaning/rinsing step is then performed, such as with acetone or other suitable stripper with a polyimide developer and rinse (these are specific to the type of polyimide used. Acetone is for photoresist). The developer and rinse for PI2730 series polyimide is DE9040 and RI9180, which washes away all of the uncured polyimide, leaving any shape or structure as desired by the designer which is determined by the shape of cut out 228 of the mask 2024. As one can see from other features and embodiments of the present invention, described above, any number of shapes of the polyimide substrate 1640 can be fastened in this manner.

Figure 97:
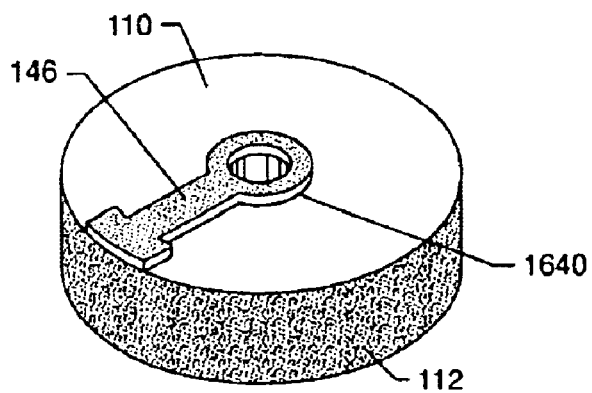
FIG. 97 is a perspective view of the capacitor of FIG. 95, with the cured area having a conductive coating and the uncured portion of the substrate removed.
Figure 98:
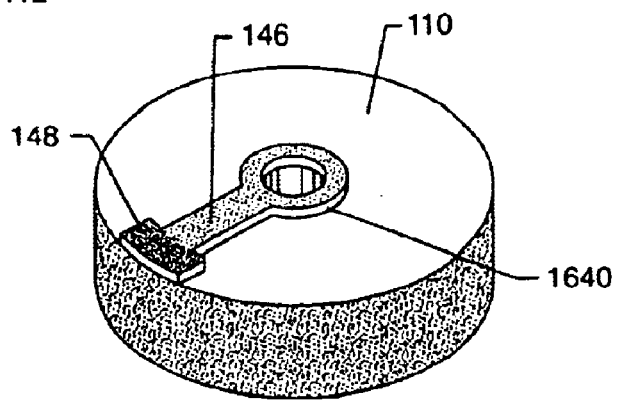
FIG. 98 is a perspective view similar to FIG. 97, illustrating the creation of a wire bonding area of the substrate.

With reference now to FIGS. 97 and 98, a metallic circuit trace 146 is formed over the cured polyimide substrate 1640. There are a number of methods for the application of the conductive circuit trace 146. Photoresist techniques can be used along with conventional circuit trace application techniques, including cladding, electroplating, PVD, CVD and the like. A particularly preferred method of application of the circuit trace 146 is through a metal evaporator using electron beam technology. A layer of titanium can be laid down and then a layer of gold in two steps. Typically, 500 angstroms of titanium would be applied and then 1000 to 2000 angstroms of gold. In order to improve the adhesion and wettability of the conductive material to the polyimide substrate 1640, one can first put down an insulating layer of a bonding activator, such as silicone nitrite oxide, silicon nitride or silicon dioxide, which bonds very well to the polyimide 1640 and also makes a very receptive surface for conductive materials to be formed by metal evaporators and the like.

With reference to FIG. 98, once the conductive circuit trace 146 is formed, a wire bond pad area 148 is built up which is suitable for wire bonding. This is typically done by electroplating multiple layers of ultrapure or soft gold. Selective area plating is well-known in the art and can be done by photoresist techniques in combination with bulk barrel plating or selective electroplating processes. If selective plating is not required, the wire bond material 148 could be plated over the entire top of the circuit trace 146, although when using gold this would be more expensive. Of course, any Kovar bond pad in accordance with the present invention could also be applied to this area for attachment of the lead wire.

Figure 99:
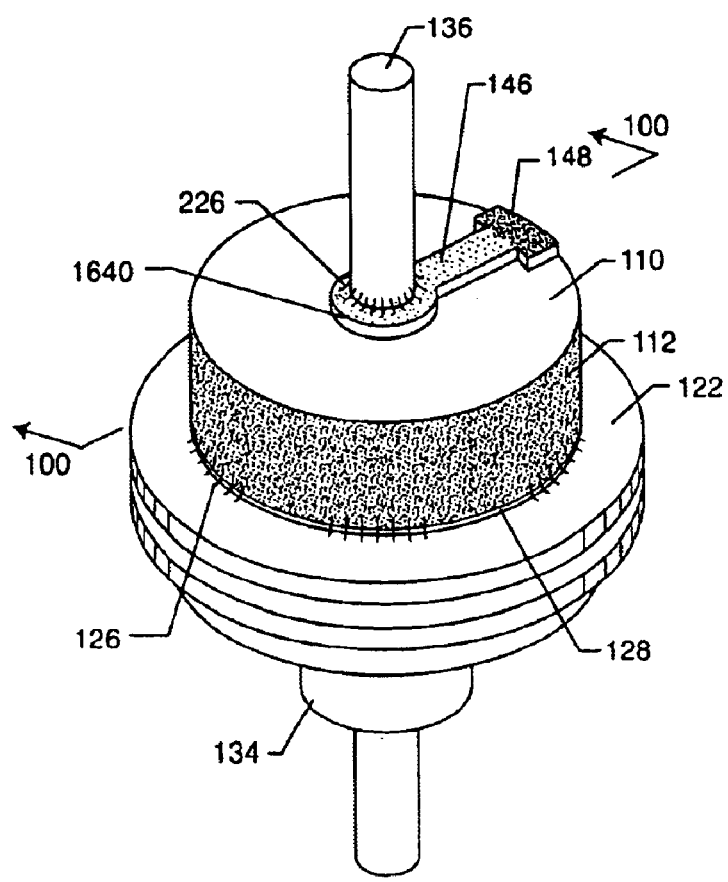
FIG. 99 is a perspective view of an EMI terminal assembly manufactured utilizing a curable substrate in accordance with the present invention.
Figure 100:
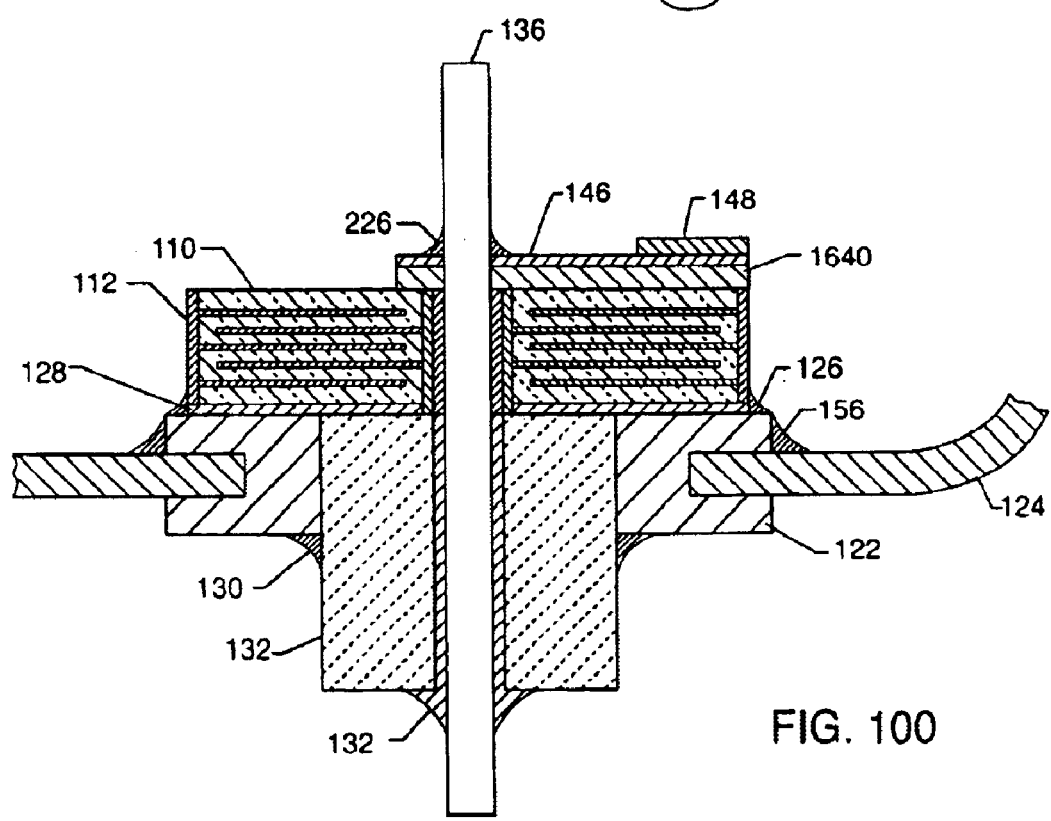
FIG. 100 is a cross-sectional view taken generally along line 98—98 of FIG.

With reference now to FIGS. 99 and 100, the assembly of FIG. 98 is slipped over the terminal pin 136 on top of the ferrule 122. A conductive attachment 126 is made between the capacitor outside diameter metallization 112 and the ferrule 122 using conductive material 126. An additional step is to form the electrical connection 226 between the lead wire 136 and the circuit trace 146, such as by using thermal setting conductive material or solder. This makes a reliable connection between the lead wire 136 and the conductive circuit trace 146. The build-up of the ultrapure gold wire bond pad area 148 is illustrated in FIG. 100. As previously mentioned, feedthrough capacitors 110 are typically made of dielectric materials, including a group of barium titanate and strontium titanate. It is well-known in the art that as one increases the dielectric constant, K, of such materials, they become structurally quite weak. Accordingly, it is undesirable to have the wire bond pad area 148 placed directly on top of the capacitor 110. This is because the forces generated during attachment of the lead wire 186 (not shown) can fracture the ceramic capacitor 110, as previously described. The forces that are generated during ultrasonic wire bonding are quite significant. As discussed above, the polyimide substrate 1640 absorbs and shields these forces from the capacitor 110.

Although the embodiment illustrated in FIGS. 95–100 has been described as using a UV curable polyimide, it will be understood by those skilled in the art that other means for curing such polyimides can be used in accordance with the present invention. Such other means include other photo definable polyimides, polyimides cured by elevated temperature curing processes, etc. The important aspect of the present invention is that the polyimide 1640 can be cured across its entirety, or across only a selected area.

Figure 101:
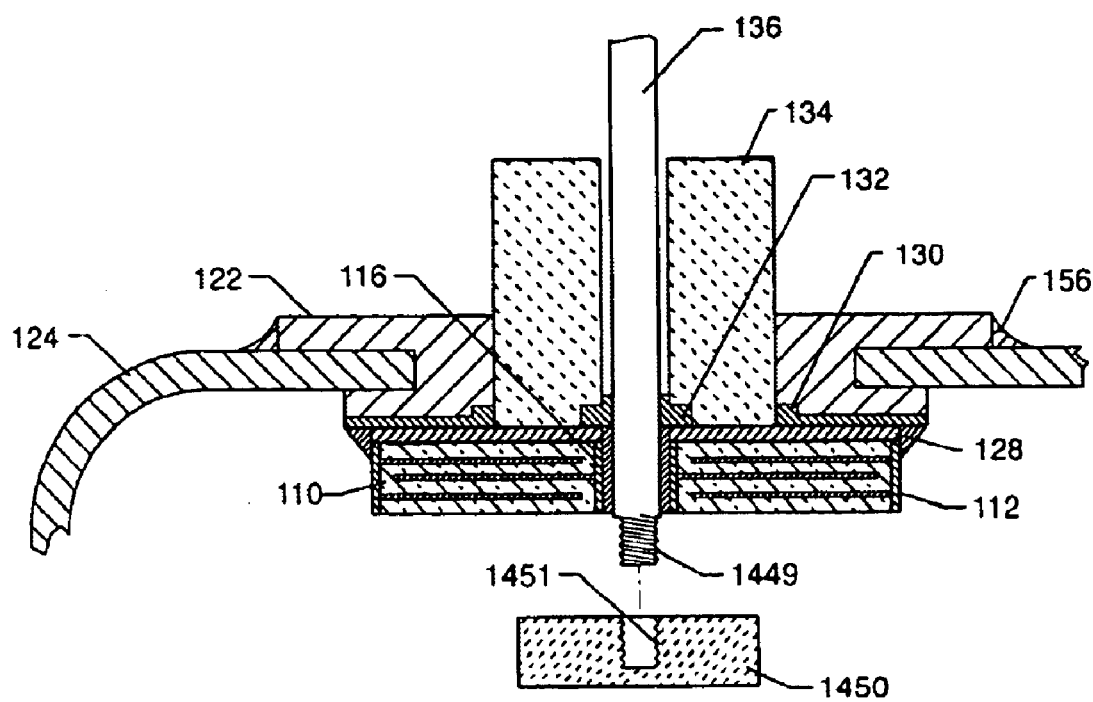
FIG. 101 is a sectional view of yet another embodiment of the invention similar to that shown in FIG. 9, wherein the wire bond cap has been drilled and threaded.

In FIG. 101, an alternative method of attaching wire bond cap 1450 is illustrated. FIG. 101 is similar to FIG. 9. The novel wire bond cap 1450 has been drilled and threaded 1451 as shown. This is designed to mate up with a threaded portion 1449 of lead wire 136. Such threads can typically be formed using screw machines and the like. The threaded-on wire bond cap 1450 is typically constructed of Kovar or Alloy 42 which is then nickel plated and then over plated with pure gold suitable for wire bonding. The shape of the wire bond cap of 1450 can be circular, rectangular, hexagonal or any other shape to fit a convenient tool for screwing the device into place. Additionally, a bonding washer (not shown) could be used sandwiched between the threaded wire bond cap 1450 and the top surface of the ceramic capacitor 110. After threading the wire bond cap 1450 into place, this washer could be cured which would firmly seat the threaded cap into position so that it would be able to withstand shock and vibration forces. Of course, there are a number of other methods of securing the threaded portion 1450 and 1499 using resistance welding, laser welding, solders, thermal setting conductive adhesives on the threads and the like. Additionally, many of the wire bond embodiments shown throughout the Figures in this application could be adapted to threading as illustrated in FIG. 101.

Figure 102:
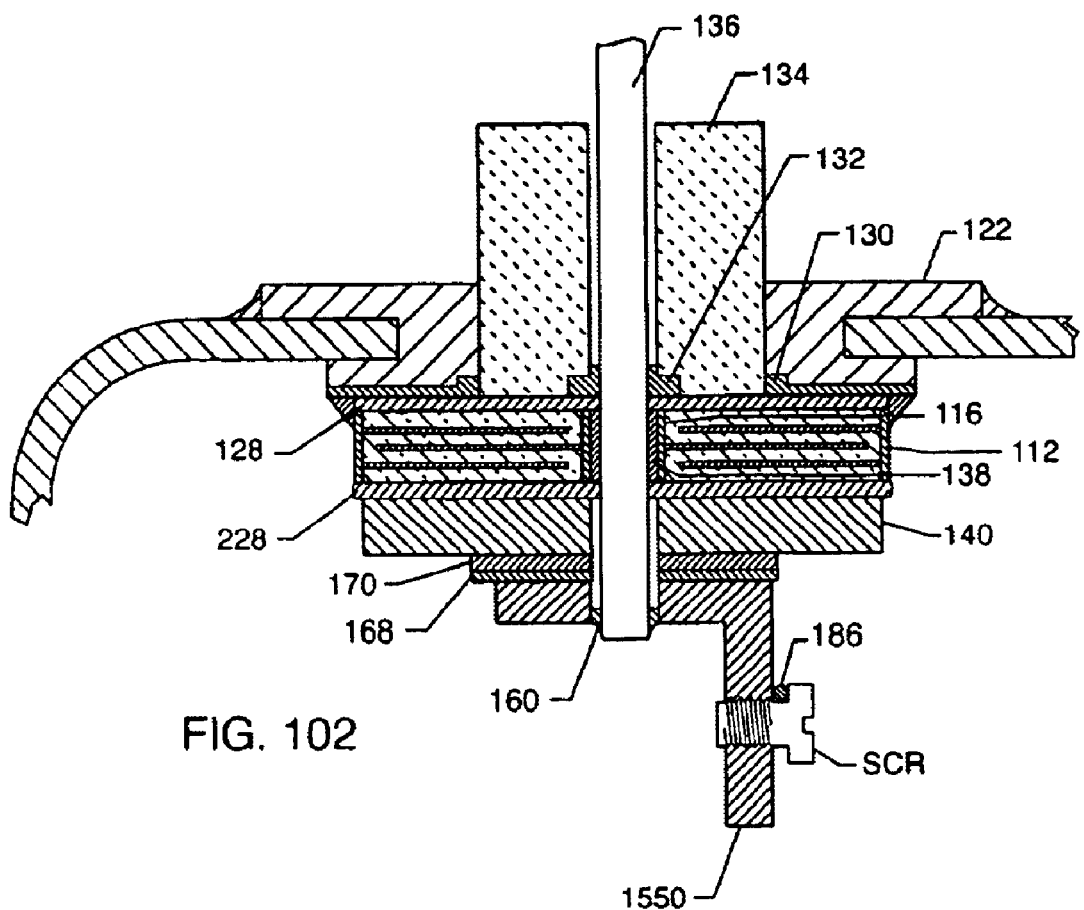
FIG. 102 is yet another embodiment that is a sectional view of yet another embodiment of the invention similar to that illustrated in FIG. 8, wherein the wire bond cap has been modified to include a threaded hole.

FIG. 102 is similar to FIG. 8 except that the L-shaped wire bond cap 1550 has been modified to include a threaded hole. This threaded hole is designed to receive a screw or other fastening device shown as SCR. A wire from pacemaker circuitry 186 is shown compressed between the screw SCR and the wire bond cap 1550. In this case, since a mechanical attachment is being made, it is not necessary that the wire bond cap 1550 be of Alloy 42 or Kovar. In fact, wire bond cap 1550 could be from a variety of metals, including something inexpensive like tin-coated copper. The fastener shown as SCR could be a slotted screw, a hex-head screw, an allen-set screw, a rivet, or a variety of other fasteners.

Figure 103:
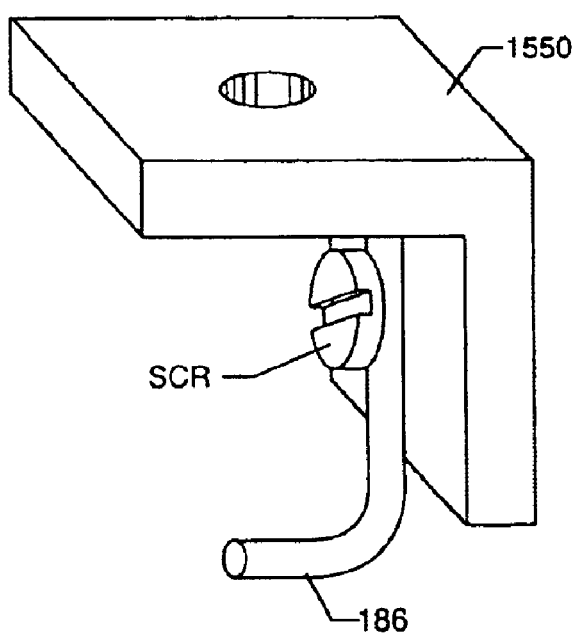
FIG. 103 is an enlarged perspective view of an L-shaped bond pad similar to that shown in FIG. 102, illustrating a screw placed on the opposite side for compressing a wire therebetween.

FIG. 103 illustrates the screw SCR being placed on the opposite side compressing over wire 186. Such are well known in the art.

Although several embodiments of the present invention have been described in detail for purposes of illustration, various modifications of each may be made without departing from the spirit and scope of the invention. Accordingly, the invention is not to be limited, except as by the appended claims.

What is claimed is:

1. An electromagnetic interference filter terminal assembly, comprising:
   a capacitor having first and second sets of electrode plates, the second set of electrode plates being conductively coupled to a ground;
   a structural pad disposed adjacent to the capacitor and including a wire bond pad conductively coupled to the first set of electrode plates; and
   a lead wire conductively coupled to the structural pad;
   wherein the structural pad is configured to at least partially protect the capacitor from forces incident to conductive coupling of the lead wire to the first set of electrode plates.

2. The assembly of claim 1, wherein the structural pad comprises a substrate disposed adjacent to a planar surface of the capacitor.

3. The assembly of claim 2, wherein the substrate comprises a ceramic-based material.

4. The assembly of claim 2, wherein the substrate is selected from an alumina, ceramic, berrylia, aluminum nitride, Fosterite, polyimide, cyanate ester, barium titanate, epoxy or fiber-reinforced material.

5. The assembly of claim 2, wherein the substrate includes a conductive surface trace having a bonding area.

6. The assembly of claim 5, wherein the lead wire is attached to the bonding area.

7. The assembly of claim 2, including an insulative material disposed between the substrate and the capacitor.

8. The assembly of claim 1, wherein the lead wire is conductively coupled to the wire bond pad.

9. The assembly of claim 8, wherein the wire bond pad is conductively coupled to the first set of electrode plates.

10. The assembly of claim 8, wherein the structural pad includes a substrate disposed adjacent to the capacitor, the wire bond pad being attached to the substrate.

11. The assembly of claim 10, wherein the wire bond pad includes a first portion conductively coupled to the first set of electrode plates, and a second portion conductively coupled to the lead wire.

12. The assembly of claim 11, wherein the first and second portions of the wire bond pad are angularly displaced relative to one another.

13. The assembly of claim 1, wherein the capacitor comprises a feedthrough capacitor having a terminal pin extending therethrough and conductively coupled to the first set of electrode plates.

14. The assembly of claim 13, including a conductive ferrule conductively coupled to the ground and to the second set of electrode plates.

15. The assembly of claim 14, wherein the ferrule is conductively coupled to a housing of an active implantable medical device.

16. The assembly of claim 14, wherein the structural pad comprises a substrate having an aperture into which the terminal pin extends.

17. The assembly of claim 16, wherein the substrate includes a conductive surface trace having a bonding area.

18. The assembly of claim 17, wherein the substrate aperture is substantially lined with a conductive material which couples the first set of electrode plates and the conductive surface trace.

19. The assembly of claim 16, wherein the terminal pin is conductively coupled to the lead wire, and wherein the substrate aperture is substantially lined with conductive material to define an electrical path from the first set of electrode plates to the lead wire independent of the terminal pin.

20. The assembly of claim 19, wherein the structural pad and the capacitor form a subassembly independent of the ferrule and the terminal pin prior to assembly therewith.

21. The assembly of claim 19, including a conductive insert disposed within a substrate recess for conductively coupling the substrate with the capacitor.

22. The assembly of claim 16, wherein the substrate includes an aperture, hole or slot for facilitating laser welding of the substrate to the terminal pin.

23. The assembly of claim 22, wherein the conductive wire bond pad has a socket for receiving an end of the terminal pin therein.

24. The assembly of claim 23, wherein the wire bond pad and the capacitor form a subassembly independent of the ferrule and the terminal pin prior to assembly therewith.

25. The assembly of claim 23, wherein the aperture, hole or slot extends at least partially through the wire bond pad.

26. The assembly of claim 25, wherein the wire bond pad is attached to the capacitor.

27. The assembly of claim 23, wherein the wire bond pad is spaced apart from the capacitor and supported solely on the terminal pin.

28. The assembly of claim 16, wherein the structural pad comprises a conductive insert ring disposed within a recess in the substrate, the insert ring being conductively coupled to the terminal pin and the substrate.

29. The assembly of claim 28, wherein the substrate includes a conductive trace conductively coupled to the insert ring, and defining a lead wire bonding area on a surface of the substrate.

30. The assembly of claim 29, wherein the wire bond pad is conductively coupled to the bonding area.

31. The assembly of claim 16, wherein the wire bond pad is conductively coupled to the first set of electrode plates through the substrate.

32. The assembly of claim 31, wherein the wire bond pad is disposed over an end of the terminal pin.

33. The assembly of claim 31, wherein the wire bond pad includes a through-hole or slot to facilitate laser melting of a tip of the terminal pin.

34. The assembly of claim 33, wherein the terminal pin is conductively coupled to the first set of electrode plates through the wire bond pad.

35. The assembly of claim 31, wherein the wire bond pad includes a head configured to lie adjacent to a surface of the capacitor, and a neck extending from the head into the capacitor about an end of the terminal pin.

36. The assembly of claim 35, wherein the terminal pin is conductively coupled to the first set of electrode plates through the wire bond pad.

37. The assembly of claim 31, wherein the lead wire is mechanically attached to the wire bond pad.

38. The assembly of claim 27, including a screw to mechanically attach the lead wire to the wire bond pad.

39. The assembly of claim 16, wherein the capacitor is internally grounded and comprises a plurality of terminal pins, including a ground terminal pin, and the substrate includes a corresponding number of conductive traces each defining a respective bonding area.

40. The assembly of claim 39, wherein the wire bond pad is conductively bonded at least to one of the bonding areas.

41. The assembly of claim 40, wherein the wire bond pad includes an aperture through which the terminal pin extends.

42. The assembly of claim 41, wherein the terminal pin and the structural pad are electrically connected to one another.

43. The assembly of claim 39, wherein a lead wire is attached to one of the wire bonding areas.

44. The assembly of claim 39, wherein the substrate includes recesses configured for receiving corresponding conductive wire bond pads therein.

45. The assembly of claim 44, wherein the wire bond pads each include an aperture for receiving a respective terminal pin therethrough, each respective terminal pin and wire bond pad being conductively attached to one another.

46. The assembly of claim 45, wherein the terminal pins and the wire bond pads are welded to one another.

47. The assembly of claim 16, wherein the substrate includes a tapered edge.

48. The assembly of claim 47, wherein the capacitor comprises an internally grounded capacitor having multiple apertures therethrough for passage of multiple terminal pins, including a ground pin, and wherein the substrate includes corresponding aligned apertures and wire bond pads conductively coupled to each terminal pin.

49. The assembly of claim 14, wherein the wire bond pad is attached to a surface of the capacitor and conductively coupled to the terminal pin.

50. The assembly of claim 49, wherein the terminal pin and wire bond pad are laser welded to one another.

51. The assembly of claim 49, wherein the wire bond pad includes an extension to which the lead wire is attached.

52. The assembly of claim 14, wherein the wire bond pad is attached to a surface of the capacitor so as to be in conductive relation to the first set of electrode plates, and wherein the wire bond pad is disposed over an end of the terminal pin.

53. The assembly of claim 14, wherein the ferrule comprises a capture flange into which the capacitor is at least partially disposed.

54. The assembly of claim 14, wherein the capacitor is embedded within the ferrule.

55. The assembly of claim 54, including an inductor closely associated with the capacitor.

56. The assembly of claim 14, wherein the structural pad is mechanically attached to the terminal pin.

57. The assembly of claim 56, wherein the structural pad is threaded onto an end of the terminal pin.

58. The assembly of claim 13, wherein the wire bond pad is disposed adjacent to the capacitor and is conductively coupled to the terminal pin.

59. The assembly of claim 58, wherein the wire bond pad is comprised of Kovar or Alloy 42.

60. The assembly of claim 58, including an electrically insulative material disposed between the wire bond pad and the capacitor.

61. The assembly of claim 58, wherein the wire bond pad includes a socket for receiving an end of the terminal pin therein.

62. The assembly of claim 61, wherein the end of the terminal pin and the wire bond pad are conductively attached to one another.

63. The assembly of claim 58, wherein a portion of the terminal pin extending from the substrate is bent, and the wire bond pad is configured for placement over the bent portion of the terminal pin.

64. The assembly of claim 13, wherein the wire bond pad is attached to the structural pad through which the terminal pin at least partially extends, the wire bond pad being conductively coupled to the terminal pin, and having an extension to which the lead wire is attached.

65. The assembly of claim 64, wherein the wire bond pad is laser welded to the terminal pin.

66. The assembly of claim 13, wherein the capacitor is internally grounded.

67. The assembly of claim 13, wherein the structural pad and the capacitor have aligned leak detection vents.

68. The assembly of claim 13, including an inductor closely associated with the capacitor.

69. The assembly of claim 13, wherein the wire bond pad is attached to the capacitor perpendicular to and conductively with the first set of electrode plates.

70. The assembly of claim 69, wherein the structural pad comprises a conductive insert ring disposed within a recess of the capacitor, the insert ring being conductively coupled to the terminal pin and the first set of electrode plates.

71. The assembly of claim 70, wherein the structural pad comprises a rectilinear multilayer substrate which is bonded to a circular feedthrough capacitor.

72. The assembly of claim 13, wherein the structural pad includes embedded conductive circuit traces extending from the terminal pin to a conductive wire bonding area on a surface of the structural pad.

73. The assembly of claim 72, wherein the wire bond pad is conductively coupled to the wire bonding area.

74. The assembly of claim 72, including a conductive insert disposed within a recess in the structural pad to facilitate secure conductive contact with the terminal pin.

75. The assembly of claim 74, wherein the insert and the terminal pin are attached to one another.

76. The assembly of claim 1, wherein the capacitor comprises a chip capacitor, and wherein the wire bond pad is attached to a conductive surface of the capacitor.

77. The assembly of claim 76, wherein the wire bond pad has an angled configuration.

78. The assembly of claim 77, wherein a first portion of the wire bond pad is attached to an upper surface of the capacitor and a second portion of the wire bond pad is conductively attached to the conductive surface of the capacitor.

79. The assembly of claim 77, wherein the structural pad includes a substrate disposed between the wire bond pad and the capacitor.

80. The assembly of claim 1, wherein the capacitor comprises a chip capacitor having an aperture extending at least partially therethrough, and a conductive pin disposed within the aperture and conductively coupled to one of the first and second sets of electrode plates.

81. The assembly of claim 80, wherein the structural pad comprises a substrate attached to the capacitor and conductively coupled to the pin.

82. The assembly of claim 81, wherein the wire bond pad has an extension for attachment of the lead wire thereto.

83. The assembly of claim 13, wherein the terminal pin has an enlarged end adjacent to the structural pad adapted to be connected to the lead wire.

84. The assembly of claim 13, wherein the structural pad comprises an ultraviolet cured material.

85. The assembly of claim 84, wherein the structural pad is formed in a process comprising the steps of:
applying a curable substrate to a surface of the capacitor;
curing a portion of the substrate;
removing the non-cured portion of the substrate; and
attaching conductive material onto the remaining cured portion of the substrate adapted for connection of the lead wire thereto.

86. The assembly of claim 85, wherein the substrate comprises a nonconductive polyimide.

87. The assembly of claim 85, wherein the curing step comprises exposing a portion of the polyimide to a radiation source.

88. The assembly of claim 87, wherein the radiation source comprises ultraviolet light.

89. The assembly of claim 87, including the step of placing a mask having a cut-out over the substrate and directing the radiation through the cut-out.

90. The assembly of claim 85, wherein the applying step comprises the step of spin coating the substrate onto a top surface of the capacitor.

91. The assembly of claim 85, wherein the removing step comprises exposing the substrate to a chemical wash.

92. The assembly of claim 85, wherein the attaching step comprises the step of electroplating the substrate with the conductive material.

93. The assembly of claim 85, wherein the attaching step comprises the step of vaporizing conductive material onto the substrate.

94. The assembly of claim 1, wherein the wire bond pad is integrally formed with the structural pad.

95. An electromagnetic interference filter terminal assembly for an active implantable medical device, comprising:
a conductive ferrule conductively coupled to a housing of the active implantable medical device;
a feedthrough capacitor having first and second sets of electrode plates, the second set of electrode plates being conductively coupled to the ferrule;
a conductive terminal pin extending through the capacitor and conductively coupled to the first set of electrode plates;
a structural pad including a wire bond pad disposed adjacent to the capacitor; and
a lead wire conductively coupled to the first set of electrode plates by means of the structural pad;
wherein the structural pad is configured to at least partially protect the capacitor from forces incident to conductive coupling of the lead wire to the first set of electrode plates.

96. The assembly of claim 95, wherein the structural pad comprises a substrate disposed adjacent to a planar surface of the capacitor.

97. The assembly of claim 96, wherein the substrate comprises a ceramic-based material.

98. The assembly of claim 96, wherein the substrate is selected from an alumina, ceramic, berrylia, aluminum nitride, Fosterite, polyimide, cyanate ester, barium titanate, epoxy or fiber-reinforced material.

99. The assembly of claim 96, wherein the substrate includes a conductive surface trace having a bonding area.

100. The assembly of claim 99, wherein the lead wire is attached to the bonding area.

101. The assembly of claim 96, including an insulative material disposed between the substrate and the capacitor.

102. The assembly of claim 95, wherein the wire bond pad is attached to the substrate, and the lead wire is conductively coupled to the wire bond pad.

103. The assembly of claim 102, wherein the wire bond pad is conductively coupled to the first set of electrode plates.

104. The assembly of claim 102, wherein the structural pad includes a substrate disposed adjacent to the capacitor, the wire bond pad being attached to the substrate.

105. The assembly of claim 104, wherein the wire bond pad includes a first portion conductively coupled to the first set of electrode plates, and a second portion conductively coupled to the lead wire.

106. The assembly of claim 105, wherein the first and second portions of the wire bond pad are angularly displaced relative to one another.

107. The assembly of claim 95, wherein the structural pad comprises a substrate having an aperture into which the terminal pin extends.

108. The assembly of claim 107, wherein the terminal pin is conductively coupled to the lead wire, and wherein the substrate aperture is substantially lined with conductive material to define an electrical path from the first set of electrode plates to the lead wire independent of the terminal pin.

109. The assembly of claim 108, wherein the structural pad and the capacitor form a subassembly independent of the ferrule and the terminal pin prior to assembly therewith.

110. The assembly of claim 108, including a conductive insert disposed within a substrate recess for conductively coupling the substrate with the capacitor.

111. The assembly of claim 107, wherein the substrate includes an aperture, hold or slot for facilitating laser welding of the substrate to the terminal pin.

112. The assembly of claim 111, wherein the wire bond pad has a socket for receiving an end of the terminal pin therein.

113. The assembly of claim 112, wherein the wire bond pad and the capacitor form a subassembly independent of the ferrule and the terminal pin prior to assembly therewith.

114. The assembly of claim 112, wherein the aperture, hole or slot extends at least partially through the wire bond pad.

115. The assembly of claim 114, wherein the wire bond pad is attached to the capacitor.

116. The assembly of claim 112, wherein the wire bond pad is spaced apart from the capacitor and supported solely on the terminal pin.

117. The assembly of claim 107, wherein the structural pad comprises a conductive insert ring disposed within a recess in the substrate, the insert ring being conductively coupled to the terminal pin and the substrate.

118. The assembly of claim 117, wherein the substrate includes a conductive trace conductively coupled to the insert ring, and defining a lead wire bonding area on a surface of the substrate.

119. The assembly of claim 118, wherein the wire bond pad is conductively coupled to the bonding area.

120. The assembly of claim 107, wherein the wire bond pad is conductively coupled to the first set of electrode plates through the substrate.

121. The assembly of claim 120, wherein the wire bond pad is disposed over an end of the terminal pin.

122. The assembly of claim 120, wherein the wire bond pad includes a through-hole or slot to facilitate laser melting of a tip of the terminal pin.

123. The assembly of claim 122, wherein the terminal pin is conductively coupled to the first set of electrode plates through the wire bond pad.

124. The assembly of claim 120, wherein the wire bond pad includes a head configured to lie adjacent to a surface of the capacitor, and a neck extending from the head into the capacitor about an end of the terminal pin.

125. The assembly of claim 124, wherein the terminal pin is conductively coupled to the first set of electrode plates through the wire bond pad.

126. The assembly of claim 120, wherein the lead wire is mechanically attached to the wire bond pad.

127. The assembly of claim 126, including a screw to mechanically attach the lead wire to the wire bond pad.

128. The assembly of claim 107, wherein the capacitor is internally grounded and comprises a plurality of terminal pins, including a ground terminal pin, and the substrate includes a corresponding number of conductive traces each defining a respective bonding area.

129. The assembly of claim 128, wherein the wire bond pad is conductively bonded to at least one of the bonding areas.

130. The assembly of claim 129, wherein the wire bond pad includes an aperture through which the terminal pin extends.

131. The assembly of claim 130, wherein the terminal pin and the structural pad are electrically connected to one another.

132. The assembly of claim 128, wherein a lead wire is attached to one of the wire bonding areas.

133. The assembly of claim 128, wherein the substrate includes recesses configured for receiving corresponding conductive wire bond pads therein.

134. The assembly of claim 133, wherein the wire bond pads each include an aperture for receiving a respective terminal pin therethrough, each respective terminal pin and wire bond pad being conductively attached to one another.

135. The assembly of claim 134, wherein the terminal pins and the wire bond pads are welded to one another.

136. The assembly of claim 107, wherein the substrate includes a tapered edge.

137. The assembly of claim 136, wherein the capacitor comprises an internally grounded capacitor having multiple apertures therethrough for passage of multiple terminal pins, including a ground pin, and wherein the substrate includes corresponding aligned apertures and wire bond pads conductively coupled to each terminal pin.

138. The assembly of claim 95, wherein the wire bond pad is disposed adjacent to the capacitor and conductively coupled to the terminal pin.

139. The assembly of claim 138, wherein the wire bond pad is comprised of Kovar or Alloy 42.

140. The assembly of claim 138, including an electrically insulative material disposed between the wire bond pad and the capacitor.

141. The assembly of claim 138, wherein the wire bond pad includes a socket for receiving an end of the terminal pin therein.

142. The assembly of claim 141, wherein the end of the terminal pin and the wire bond pad are conductively attached to one another.

143. The assembly of claim 138, wherein a portion of the terminal pin extending from the substrate is bent, and the wire bond pad is configured for placement over the bent portion of the terminal pin.

144. The assembly of claim 95, wherein the wire bond pad is attached to the structural pad through which the terminal pin at least partially extends, the wire bond pad being conductively coupled to the terminal pin, and having an extension to which the lead wire is attached.

145. The assembly of claim 144, wherein the wire bond pad is laser welded to the terminal pin.

146. The assembly of claim 95, wherein the wire bond pad is attached to a surface of the capacitor and is conductively coupled to the terminal pin.

147. The assembly of claim 146, wherein the terminal pin and wire bond pad are laser welded to one another.

148. The assembly of claim 146, wherein the wire bond pad includes an extension to which the lead wire is attached.

149. The assembly of claim 95, wherein the wire bond pad is attached to a surface of the capacitor so as to be in conductive relation to the first set of electrode plates, and wherein the wire bond pad is disposed over an end of the terminal pin.

150. The assembly of claim 95, wherein the capacitor is internally grounded.

151. The assembly of claim 95, wherein the structural pad and the capacitor have aligned leak detection vents.

152. The assembly of claim 95, wherein the ferrule comprises a capture flange into which the capacitor is at least partially disposed.

153. The assembly of claim 95, including an inductor closely associated with the capacitor.

154. The assembly of claim 95, wherein the capacitor is embedded within the ferrule.

155. The assembly of claim 154, including an inductor closely associated with the capacitor.

156. The assembly of claim 95, wherein the wire bond pad is attached to the capacitor perpendicular to and conductively with the first set of electrode plates.

157. The assembly of claim 156, wherein the structural pad comprises a conductive insert ring disposed within a recess of the capacitor, the insert ring being conductively coupled to the terminal pin and the first set of electrode plates.

158. The assembly of claim 95, wherein the structural pad includes embedded conductive circuit traces extending from the terminal pin to a conductive wire bonding area on a surface of the structural pad.

159. The assembly of claim 158, wherein the wire bond pad is conductively coupled to the wire bonding area.

160. The assembly of claim 158, wherein the structural pad comprises a rectilinear multilayer substrate which is bonded to a circular feedthrough capacitor.

161. The assembly of claim 158, including a conductive insert disposed within a recess in the structural pad to facilitate secure conductive contact with the terminal pin.

162. The assembly of claim 161, wherein the insert and the terminal pin are attached to one another.

163. The assembly of claim 95, wherein the terminal pin has an enlarged end adjacent to the structural pad adapted to be connected to the lead wire.

164. The assembly of claim 95, wherein the structural pad comprises an ultraviolet cured material.

165. The assembly of claim 164, wherein the structural pad is formed in a process comprising the steps of:

applying a curable substrate to a surface of the capacitor;
curing a portion of the substrate;
removing the non-cured portion of the substrate; and
attaching conductive material onto the remaining cured portion of the substrate adapted for connection of the lead wire thereto.

166. The assembly of claim 165, wherein the substrate comprises a nonconductive polyimide.

167. The assembly of claim 165, wherein the curing step comprises exposing a portion of the polyimide to a radiation source.

168. The assembly of claim 167, wherein the radiation source comprises ultraviolet light.

169. The assembly of claim 167, including the step of placing a mask having a cut-out over the substrate and directing the radiation through the cut-out.

170. The assembly of claim 165, wherein the applying step comprises the step of spin coating the substrate onto a top surface of the capacitor.

171. The assembly of claim 165, wherein the removing step comprises exposing the substrate to a chemical wash.

172. The assembly of claim 165, wherein the attaching step comprises the step of electroplating the substrate with the conductive material.

173. The assembly of claim 165, wherein the attaching step comprises the step of vaporizing conductive material onto the substrate.

174. The assembly of claim 95, wherein the structural pad is mechanically attached to the terminal pin.

175. The assembly of claim 174, wherein the structural pad is threaded onto an end of the terminal pin.

176. The assembly of claim 95, wherein the wire bond is integrally formed with the structural pad.

* * * * *

UNITED STATES PATENT AND TRADEMARK OFFICE
CERTIFICATE OF CORRECTION

PATENT NO. : 7,038,900 B2
APPLICATION NO. : 10/842967
DATED : May 2, 2006
INVENTOR(S) : Robert A. Stevenson et al.

It is certified that error appears in the above-identified patent and that said Letters Patent is hereby corrected as shown below:

In Claim 38, col. 39 line 53, replace "27" with --37--.

Signed and Sealed this

Fifteenth Day of May, 2007

JON W. DUDAS
*Director of the United States Patent and Trademark Office*